(12) United States Patent
Morishita et al.

(10) Patent No.: US 7,714,099 B2
(45) Date of Patent: May 11, 2010

(54) LUMINESCENT COMPOSITIONS AND THEIR USES

(75) Inventors: Yoshii Morishita, Tsukuba (JP); Satoyuki Nomura, Tsukuba (JP); Yoshihiro Tsuda, Tsukuba (JP); Seiji Tai, Tokyo (JP); Matthew L. Marrocco, III, Fontana, CA (US); Farshad J. Motamedi, Claremont, CA (US); Li-Sheng Wang, Arcadia, CA (US); Yongchao Liang, Irvine, CA (US)

(73) Assignees: Hitachi Chemical Co., Ltd., Tokyo (JP); Sumation Co., Ltd., Tokyo (JP)

( * ) Notice: Subject to any disclaimer, the term of this patent is extended or adjusted under 35 U.S.C. 154(b) by 1083 days.

(21) Appl. No.: 10/966,370

(22) Filed: Oct. 15, 2004

(65) Prior Publication Data

US 2006/0083945 A1    Apr. 20, 2006

(51) Int. Cl.
| | | |
|---|---|---|
| C08G 73/06 | (2006.01) | |
| C08G 73/08 | (2006.01) | |
| H01L 51/42 | (2006.01) | |
| H01L 51/46 | (2006.01) | |
| H01L 51/50 | (2006.01) | |
| H01L 51/54 | (2006.01) | |

(52) U.S. Cl. .................. 528/423; 528/377; 528/380; 428/690; 428/917; 313/504; 313/506

(58) Field of Classification Search .............. 528/423, 528/377, 380; 428/690, 917; 313/504, 506
See application file for complete search history.

(56) References Cited

FOREIGN PATENT DOCUMENTS

| JP | 09-073009 A | 3/1997 |
|---|---|---|
| JP | 09-183846 | 7/1997 |
| JP | 2001-097949 | 4/2001 |
| JP | 2001-97949 A | 4/2001 |
| WO | WO 02/059121 A1 | 8/2002 |
| WO | WO 2004/092246 A1 | 10/2004 |

OTHER PUBLICATIONS

Doroshenko, et al, Excited state intramolecular proton transfer reaction and luminescent properties of the ortho-hydroxy derivatives of 2,5-diphenyl-1,3,4-oxadiazole, Journal of Physical Organic Chemistry, 2000, 253-265, 13, John Wiley & Sons.

Stein, et al, Influence of Polymer Matrixes on the Photophysical Properties of UV Absorbers, Journal of Physical Chemistry A, 2001, 2055-2066, 106, ACS.

Maliakal, et al, Twisted Intramolecular Charge Transfer States in 2-Arylbenzotriazoles: Fluorescence Deactivation via Intramolecular Electron Transfer Rather Than Proton Transfer, Journal of Physical Chemistry A, 2002, 7680-7689, 106, ACS.

International Search Report dated Jan. 17, 2006 of PCT/JP2005/019352.

Korean Office Action issued on Feb. 18, 2009 for corresponding Korean Patent Application No. 7010893/2007.

Office Action issued on Jul. 14, 2009 for corresponding Japanese Patent Application No. 2005-505479.

*Primary Examiner*—Duc Truong
(74) *Attorney, Agent, or Firm*—Westerman, Hattori, Daniels & Adrian, LLP

(57) ABSTRACT

High quantum yield luminescent monomers, oligomers, and polymers, comprising benzotriazole repeating units and derivatives thereof have been discovered and utilized in optical devices and components therefor, including electroluminescent devices, light emitting devices, photoluminescent devices, organic light emitting diodes (OLEDs), OLED displays, sensors, and the like.

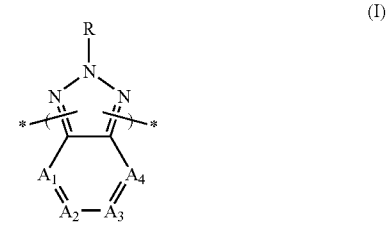

(I)

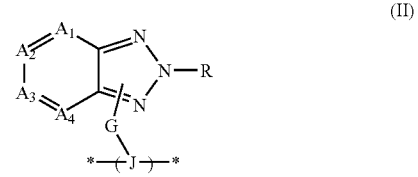

(II)

84 Claims, No Drawings

LUMINESCENT COMPOSITIONS AND THEIR USES

STATEMENT REGARDING FEDERALLY SPONSORED RESEARCH AND DEVELOPMENT

This invention was made with U.S. Government support under Contract No. N00014-02-C-0461 awarded by the Department of the United States Navy. The government may have certain rights in this invention.

CROSS-REFERENCE TO RELATED APPLICATIONS

Not Applicable

BACKGROUND OF THE INVENTION

1. Field of the Invention

The present invention relates generally to organic/polymer chemistry, and more particularly to novel luminescent compounds (polymers, oligomers, and monomers) which emit strong light when excited optically, electrically, and/or chemically; to processes for preparing said novel luminescent compounds; and to the use of said compounds in applications involving luminescence, e.g., as components of organic light emitting diodes (OLEDs), OLED displays, lights, as sensors, UV stabilizers, and the like.

2. Description of Related Art

Organic luminescence devices utilizing organic substances (either small organic molecules or polymers) have favorable prospects for the use in low-priced large-size full color displays, lasers, optoelectronic devices, photovoltaic devices, sensors, biotags, lights, and the like, and the demands therefor have been steadily growing. Such devices can emit light (e.g., organic light-emitting diodes, OLEDs, that make up displays) or respond to radiant energy (e.g., photodetectors). Compared with other tools for use in similar applications, organic luminescence devices offer many distinguishing advantages, such as their light weight, thinness, flexibility, wide range of colors, high contrast, fast response rate, low power consumption, high brightness, and no need for backlighting.

Organic luminescence devices may be classified depending on the molecular weight of their organic components and manufacturing processes: devices manufactured from low molecular weight compounds (small organic molecules) and devices manufactured using large molecular weight compounds (polymers). Low molecular weight compounds may be layered by vacuum deposition and may be easily purified to a high degree. In addition, color pixels may be easily obtained in a low molecular weight device. High molecular weight devices are more easily layered by casting, printing, dipping, spraying, lithography, and the like.

In organic luminescence devices, an organic active layer is generally sandwiched between two electrical contact layers (electrodes). At least one of the electrical contact layers is light-transmitting so that light can pass through it. The organic active layer may generate an electrical signal in response to light passing through the light-transmitting electrical contact layer, or it may emit light through the light-transmitting electrical contact layer upon application of electricity across the electrical contact layers.

Organic luminescence devices work through a double charge injection from two electrodes, i.e., holes are injected from the anode into the highest occupied molecular orbital (HOMO) of the emissive layer molecules (or first to the hole transport layer molecules if there is a hole transport layer, and then to the emissive layer molecules), and electrons from the cathode into the lowest unoccupied molecular orbital (LUMO) of the emissive layer molecules (or first to the electron transport layer molecules if there is an electron transport layer, and then to the emissive layer molecules), the hole and electron recombining in the emissive layer, thereby liberating energy as light.

Multiple layers between the two electrodes can make the light production more efficient (Tang et al. (1987) Applied Physics Letters 51: 913-915, and Burroughs et al. (1990) Nature 347: 539). The multiple layers may include one or more electron transport layers, and one or more hole transport layers. See Adachi et al. (1988) Japanese Journal of Applied Physics 27: L269-L271, and Mitschke and Bauerle (2000) J. Mater. Chem. 10: 1471-1507.

OLED displays may employ active matrix addressing or passive matrix addressing. In passive matrix displays there is an array of electrode lines for addressing individual pixels arranged in rows and columns; applying a voltage between a particular row and column energizes the pixel with that corresponding address. By analogy with active matrix liquid crystal displays, the polymer electronic device (display) can be addressed at individual pixels using, for example, a thin film transistor (TFT) device which switches that pixel on and off.

The use of organic electroluminescent materials as active materials in light emitting diodes is well known. Simple organic molecules such as anthracene, thiadiazole derivatives, and coumarin derivatives are known to show electroluminescence. Semiconductive conjugated polymers have also been used as electroluminescent materials, as has been disclosed in, for example, Friend et al, U.S. Pat. No. 5,247,190, and Heeger et al., U.S. Pat. No. 5,408,109. The organic materials can be tailored to provide emission at various wavelengths. Theoretically, it is possible to emit light of any color including red through blue by use of various organic compounds.

However, organic luminescence devices are frequently degraded by atmospheric gases, particularly oxygen and water vapor, and this instability can severely limit the working lifetime of the devices. In addition, when organic luminescence devices comprising conventional organic materials are continuously driven, the luminescence output reduces within a short time and the drive voltage has to be increased. Accordingly, there is an urgent need in the industry to improve the chemical stability/durability of layers in organic electronic devices that are sensitive to environmental elements. There is also a need to improve the durability as well as the life time of such devices. Additionally, it would also be beneficial to increase the initial luminous intensity/efficiency and color purity.

We have now discovered novel compounds, processes, and devices possessing high quantum yields which are easily prepared and modified generally by employing commercially available precursors, which help to address some of the above-mentioned deficiencies present in this area of technology.

BRIEF DESCRIPTION OF THE DRAWINGS

Not applicable

BRIEF SUMMARY OF THE INVENTION

High quantum yield luminescent polymers, oligomers, and monomers comprising benzotriazole repeating units and derivatives thereof have been discovered and are easily prepared by various processes.

Further, optical devices and components therefor are provided comprising said polymers, oligomers, and monomers. These devices include electroluminescent devices, light emitting devices, photoluminescent devices, organic light emitting diodes (OLEDs), OLED displays, sensors, and the like.

Additional objects will be evident from the following detailed description.

DETAILED DESCRIPTION OF THE INVENTION

In one embodiment of the invention described herein, the novel polymers and oligomers are composed of at least one type of constitutional repeating unit of the general formula selected from the group consisting of Formula I and Formula II, represented below:

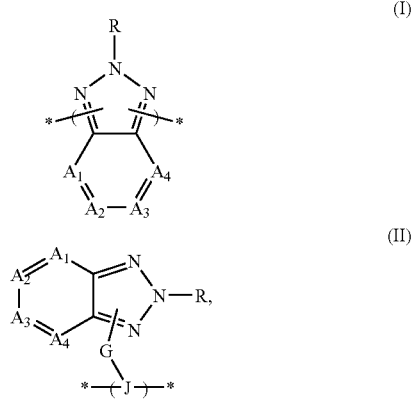

and optionally at least one type of a constitutional repeating unit of the general formula represented below by Formula III:

wherein R is H, D, alkyl, alkaryl, heteroalkyl, aryl, aralkyl, heteroaryl, alkyl ketone, aryl ketone, alkylester, arylester, amide, carboxylic acid, phenol, 2-hydroxyphenyl, 2-alkoxyphenyl, 2-aryloxyphenyl, substituted 2-hydroxyphenyl, substituted 2-alkoxyphenyl, substituted 2-aryloxyphenyl, fluoroalkyl, or fluoroaryl; $A_1$ is C, when said benzotriazole type group is linked at $A_1$, or $A_1$ is CH, $CR_1$, or N, when said benzotriazole type group is not linked at $A_1$; $A_2$ is C, when said benzotriazole type group is linked at $A_2$, or $A_2$ is CH, $CR_2$, or N, when said benzotriazole type group is not linked at $A_2$; $A_3$ is C, when said benzotriazole type group is linked at $A_3$, or $A_3$ is CH, $CR_3$, or N, when said benzotriazole type group is not linked at $A_3$; $A_4$ is CH, $CR_4$, or N, when said benzotriazole type group is not linked at $A_4$, or $A_4$ is C, when said benzotriazole type group is linked at $A_4$; J is a trivalent moiety selected from the group consisting of 1,2,4-phenylenetriyl and $>CR_6CR_7R_8$—; G is nil or is selected from the group consisting of —Ar—, —O—, —S—, —$NR_1$—, $CR_2R_3$—, —$CR_1R_2CR_3R_4$—, N=$CR_1$—, $CR_1$=$CR_2$—, —N=N—, —(CO)—, $C_3$ to $C_{30}$ alkyldiyl, and $C_3$ to $C_{30}$ heteroalkyldiyl; Q is selected from the group consisting of —Ar—, —O—, —S—, —$NR_1$—, —$OCR_1R_2$—, —$CR_1R_2$—, —$OCR_1R_2CR_3R_4$—, —$CR_1R_2CR_3R_4$—, —N=$CR_1$—, —$CR_1$=N—, —$CR_1$=$CR_2$—, —N=N—, and —(CO)—, —$BR_1$—, $SiR_1R_2$—, —(CO)—O—, —O—(CO)—, —$NR_1$—(CO)—, and —(CO)—$NR_1$—, $C_3$ to $C_{30}$ alkyldiyl, and $C_3$ to $C_{30}$ heteroalkyldiyl; $R_1$, $R_2$, $R_3$, $R_4$ are each independently selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and any two of adjacent (geminal, vicinal, or ortho) $R_1$, $R_2$, $R_3$ or $R_4$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; $R_6$, $R_7$, and $R_8$ are each independently substituted or unsubstituted alkyl or aryl; and any two of adjacent (geminal, vicinal, or ortho) $R_6$, $R_7$, $R_8$, are optionally bridging; and Ar is unsubstituted or substituted, single or multiple ring, fused or non-fused aromatic or heteroaromatic. The benzotriazole type moiety may be linked at any atom, valence and stability permitting, including at $A_1$, $A_2$, $A_3$, $A_4$, any N, and R. When the benzotriazole type moiety is linked through N at position 2, the linkage would replace the R group. When the benzotriazole type moiety is linked through R, the linkage would replace one of the hydrogen atoms of the R group.

In a class of this embodiment are the novel polymers and oligomers composed of at least one type of constitutional repeating unit of the general formula selected from the group consisting of Formula IV, Formula V, and Formula VI, represented below:

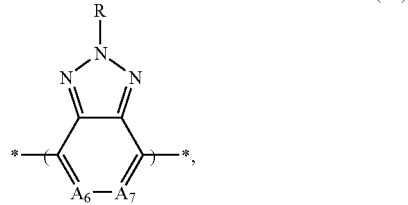

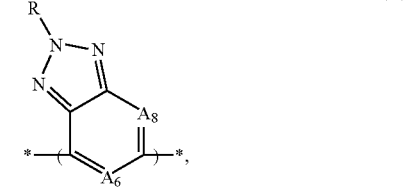

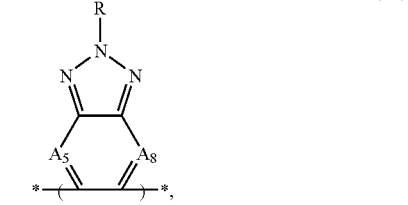

wherein R is H, D, alkyl, alkaryl, heteroalkyl, aryl, aralkyl, heteroaryl, alkyl ketone, aryl ketone, alkylester, arylester, amide, carboxylic acid, phenol, 2-hydroxyphenyl, 2-alkoxyphenyl, 2-aryloxyphenyl, substituted 2-hydroxyphenyl, substituted 2-alkoxyphenyl, substituted 2-aryloxyphenyl, fluoroalkyl, or fluoroaryl; $A_5$ is CH, $CR_1$, or N; $A_6$ is CH, $CR_2$, or N; $A_7$ is CH, $CR_3$, or N; $A_8$ is CH, $CR_4$, or N; $R_1$, $R_2$, $R_3$, $R_4$ are each independently selected from the group consisting of H, D, —NR$_6$R$_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and any two of adjacent (geminal, vicinal, or ortho) R$_1$, R$_2$, R$_3$ or R$_4$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; and R$_6$ and R$_7$ are each independently substituted or unsubstituted alkyl or aryl and are optionally bridging.

In a subclass of this embodiment of the present invention are those polymers and oligomers comprising at least one type of constitutional repeating unit of Formula VII represented below:

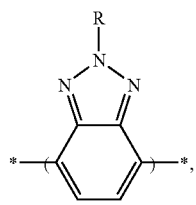

(VII)

wherein R is H, D, alkyl, aryl, alkaryl, heteroalkyl, aryl, aralkyl, heteroaryl, alkyl ketone, aryl ketone, alkylester, arylester, amide, carboxylic acid, phenol, 2-hydroxyphenyl, 2-alkoxyphenyl, 2-aryloxyphenyl, substituted 2-hydroxyphenyl, substituted 2-alkoxyphenyl, substituted 2-aryloxyphenyl, fluoroalkyl, or fluoroaryl.

In another subclass of this embodiment are those polymers and oligomers wherein R is

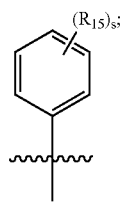

s is 0-5; R$_{15}$ is selected from the group consisting of H, D, —NR$_6$R$_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and when s is 2-5, any two of adjacent (geminal, vicinal, or ortho) R$_{15}$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; and R$_6$ and R$_7$ are each independently substituted or unsubstituted alkyl or aryl and are optionally bridging.

In another subclass of this embodiment are those polymers and oligomers wherein R is selected from the group consisting of:

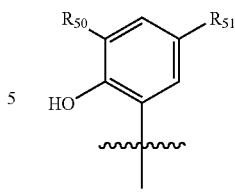 and 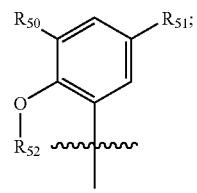

R$_{50}$ and R$_{51}$ are each independently selected from the group consisting of H, D, F, alkyl, alkaryl, heteroalkyl, aryl, aralkyl, heteroaryl, fluoroalkyl, fluoroaryl, amide, and ester; and R$_{52}$ is selected from the group consisting of alkyl, aryl, heteroaryl, fluoroalkyl, and fluoroaryl. Particularly, R is selected from the group consisting of:

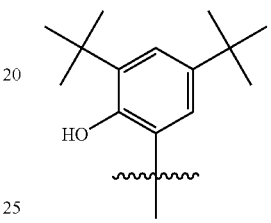 and 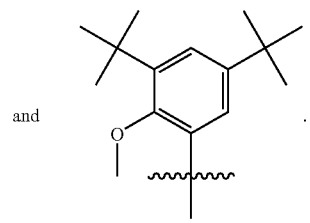.

In another subclass of this embodiment are those polymers and oligomers wherein R is alkyl. In a subclass of this class are those polymers and oligomers wherein R is n-hexyl.

In one instance are those polymers and oligomers comprising (in addition to at least one type of constitutional repeating unit of Formulas IV, V, VI and VII) at least one additional type of constitutional repeating unit of Formula III represented below:

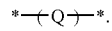

(III)

In this instance, Q is particularly

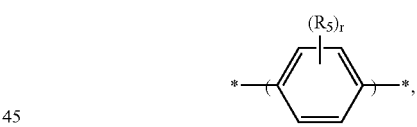

wherein: R$_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent (geminal, vicinal, or ortho) R$_5$ groups are optionally bridging; and r is 0-4. And more particularly, Q is

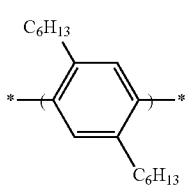 or 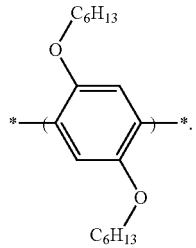.

In another instance Q is particularly

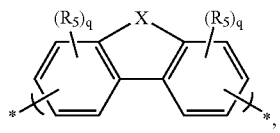

wherein: $R_5$ is each independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, and any two of adjacent (geminal, vicinal, or ortho) $R_5$ groups are optionally bridging; q is 0-3; X is selected from the group consisting of —O—, —S—, —$NR_6$—, and —$CR_6R_7$—, —$CR_6R_7CR_8R_9$—, —N=$CR_6$—, $CR_6$=$CR_7$—, —N=N—, and —(CO)—; and $R_6$, $R_7$, $R_8$, and $R_9$ are each independently selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic, and any two adjacent (geminal, vicinal, or ortho) $R_6$, $R_7$, $R_8$, and $R_9$ are optionally bridging. And more particularly Q is

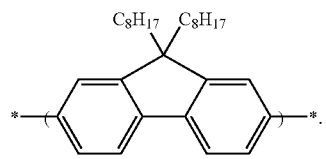

In another instance Q is particularly

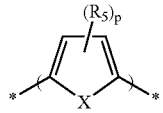

wherein: $R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent (geminal, vicinal, or ortho) $R_5$ groups are optionally bridging; p is 0-2; X is selected from the group consisting of —O—, —S—, —$NR_6$—, and $CR_6R_7$—, —$CR_6R_7CR_8R_9$—, —N=$CR_6$—, —$CR_6$=$CR_7$—, —N=N—, and —(CO)—; and $R_6$, $R_7$, $R_8$, and $R_9$ are independently selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic, and any two of adjacent (geminal, vicinal, or ortho) $R_6$, $R_7$, $R_8$, and $R_9$ are optionally bridging.

In another instance Q is particularly

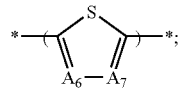

wherein $A_6$ is CH, $CR_2$, or N; $A_7$ is CH, $CR_3$, or N; $R_2$ and $R_3$ are each independently selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and $R_2$ and $R_3$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzo furan; and $R_6$ and $R_7$ are each independently substituted or unsubstituted alkyl or aryl and are optionally bridging. More particularly Q is

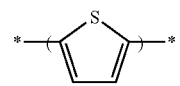

In another instance Q is particularly

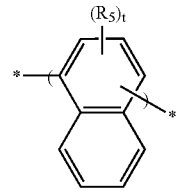

wherein: $R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, and any two of the adjacent (geminal, vicinal, or ortho) $R_5$ groups are optionally bridging, and t is 0-6; and more particularly Q is

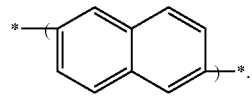

In another instance Q is particularly

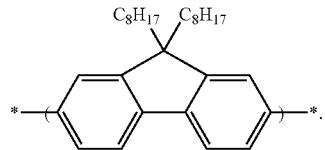

In another instance Q is particularly

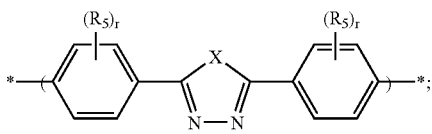

wherein R₅ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent (geminal, vicinal, or ortho) R₅ groups are optionally bridging; r is 0-4; X is selected from the group consisting of —O—, —S—, —NR₆—, and —CR₆R₇—, —CR₆R₇CR₈R₉—, —N=CR₆—, CR₆=CR₇—, —N=N—, and —(CO)—; and R₆, R₇, R₈, and R₉ are each independently selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic, and any two adjacent (geminal, vicinal, or ortho) R₆, R₇, R₈, and R₉ are optionally bridging. More particularly Q is

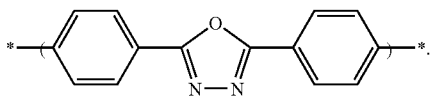

In another instance Q is particularly

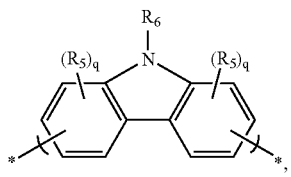

wherein: R₅ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, and any two of adjacent (geminal, vicinal, or ortho) R₅ groups are optionally bridging; q is 0-3, and R₆ is selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic; and more particularly, Q is

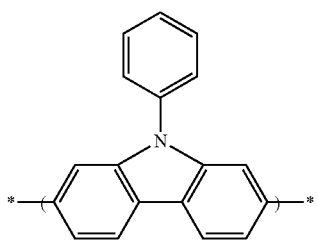

or

-continued

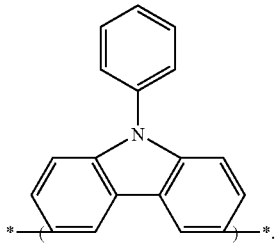

In another instance Q is particularly

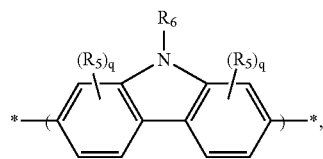

wherein: R₅ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, and any two of adjacent (geminal, vicinal, or ortho) R₅ groups are optionally bridging; q is 0-3, and R₆ is selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic.

In another instance Q is particularly

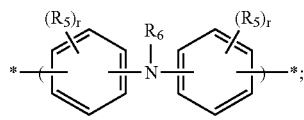

wherein R₅ is each independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent (geminal, vicinal, or ortho) R₅ groups are optionally bridging; R₆ is selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic; and r is 0-4; and more particularly, Q is

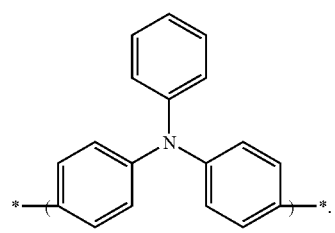

In another instance are those polymers and oligomers comprising (in addition at least one type of constitutional repeating unit selected from the group consisting of those represented by Formula IV, V, VI and VII) at least two additional and different types of constitutional repeating unit of Formula III represented below:

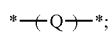
(III)

wherein at least one Q is selected from the group consisting of

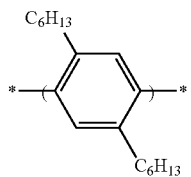 and 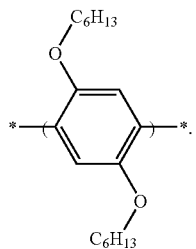

In another instance are those polymers and oligomers comprising (in addition at least one type of constitutional repeating unit selected from the group consisting of those represented by Formula IV, V, VI and VII) at least two additional and different types of constitutional repeating unit of Formula III represented below:

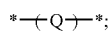
(III)

wherein at least one Q is selected from the group consisting of

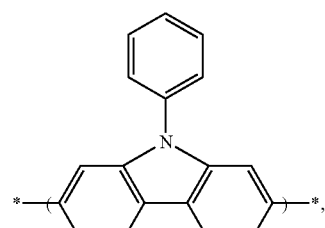,

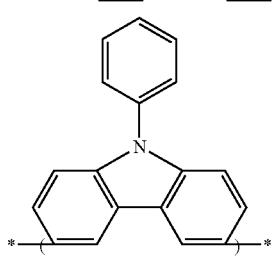 and

-continued

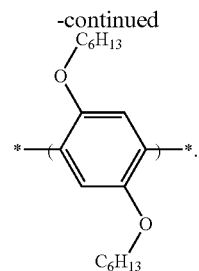.

In another instance are those polymers and oligomers comprising (in addition at least one type of constitutional repeating unit selected from the group consisting of those represented by Formula IV, V, VI and VII) at least two additional and different types of constitutional repeating unit of Formula III represented below:

*—(Q)—*;   (III)

wherein at least one Q is selected from the group consisting of and

In another instance are those polymers and oligomers comprising (in addition at least one type of constitutional repeating unit of IV, V, VI and VII) at least two types of constitutional repeating unit of Formula III represented below:

*—(Q)—*;   (III)

wherein at least one Q is selected from the group consisting of and

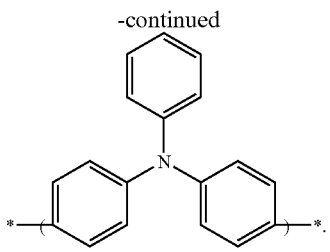

In another instance are those polymers and oligomers comprising (in addition at least one type of constitutional repeating unit selected from the group consisting of those represented by Formula IV, V, VI and VII) at least two types of constitutional repeating unit of Formula III represented below:

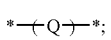

wherein at least one Q is selected from the group consisting of

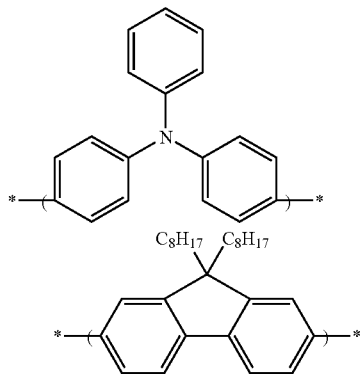

In another instance are those polymers and oligomers comprising (in addition at least one type of constitutional repeating unit selected from the group consisting of those represented by Formula IV, V, VI and VII) at least three additional and different types of constitutional repeating unit of Formula III represented below:

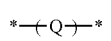

wherein at least one Q is selected from the group consisting of

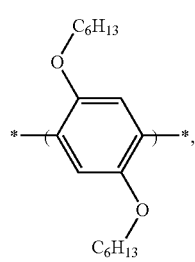

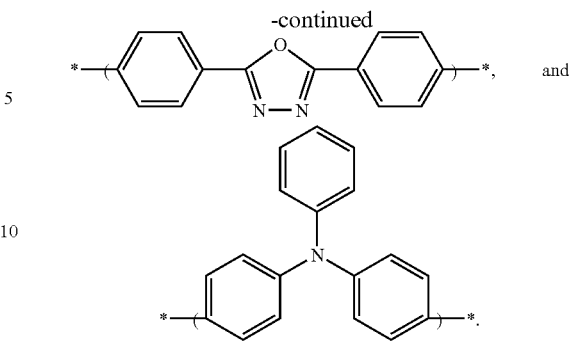

In another class of the first embodiment, the polymers and oligomers may be joined by nonconjugated spacers having, e.g., an ether group, ester group, amide group, imide group, etc. Particularly, the non-conjugated polymers of the present invention include polymers comprising aliphatic polyester, polyether, polythioether, polyolefins, polyurethane, polyimide, polyamide, polyetherketone, polycarbonate, polysulfide, polyethersulfide, a silicon-containing polymer, polycarbamate, polyepoxy, polyurea, polyurethane, polythiourethane, polysiloxane, polyacrylonitrile, polysulfone, polyanhydride, polyisocyanate, and/or copolymers thereof.

In another class of the first embodiment, the polymers and oligomers (as well as the corresponding monomers) optionally include a nonconjugated constitutional repeating unit. Exemplary nonconjugated constitutional repeating unit are those independently selected from the group consisting of —O—, —S—, —C(O)—, —OC(O)—, —C(O)O—, —C(O)NH—, —NHC(O)NH—, —OC(O)NH—, —C(S)—, —CH$_2$—, —CH$_2$CH$_2$—, —CH$_2$CH$_2$CH$_2$—, —CH$_2$CH$_2$CH$_2$CH$_2$—, —OCH$_2$—, —CH$_2$O—, —OCH$_2$CH$_2$—, —CH$_2$CH$_2$O—, —OCH$_2$CH$_2$CH$_2$—, —CH$_2$OCH$_2$CH$_2$—, —CH$_2$CH$_2$OCH$_2$—, —CH$_2$CH$_2$O—, —OCH$_2$CH$_2$CH$_2$CH$_2$—, —CH$_2$OCH$_2$CH$_2$CH$_2$—, —CH$_2$CH$_2$OCH$_2$CH$_2$—, —CH$_2$CH$_2$CH$_2$OCH$_2$—, —CH$_2$CH$_2$CH$_2$CH$_2$O—, —C(O)NHCH$_2$—, —C(O)NHCH$_2$CH$_2$—, —CH$_2$C(O)NHCH$_2$—, —CH$_2$CH$_2$C(O)NH—, —C(O)NHCH$_2$CH$_2$CH$_2$—, —CH$_2$C(O)NHCH$_2$CH$_2$—, —CH$_2$CH$_2$C(O)NHCH$_2$—, —CH$_2$CH$_2$CH$_2$C(O)NH—, —C(O)NHCH$_2$CH$_2$CH$_2$CH$_2$—, —CH$_2$C(O)NHCH$_2$CH$_2$CH$_2$—, —CH$_2$CH$_2$C(O)NHCH$_2$CH$_2$—, —CH$_2$CH$_2$CH$_2$C(O)NHCH$_2$—, —CH$_2$CH$_2$CH$_2$CH$_2$C(O)NH—, —C(O)OCH$_2$—, —CH$_2$C(O)OCH$_2$—, —CH$_2$CH$_2$C(O)OCH$_2$—, —C(O)OCH$_2$CH$_2$—, —NHC(O)CH$_2$—, —CH$_2$NHC(O)CH$_2$—, —CH$_2$CH$_2$NHC(O)CH$_2$—, —NHC(O)CH$_2$CH$_2$—, —CH$_2$NHC(O)CH$_2$CH$_2$—, —CH$_2$CH$_2$NHC(O)CH$_2$CH$_2$—, —C(O)NHCH$_2$—, —C(O)NHCH$_2$CH$_2$—, —OC(O)NHCH$_2$—, —OC(O)NHCH$_2$CH$_2$—, —OC(O)NHCH$_2$CH$_2$CH$_2$—, —NHCH$_2$—, —NHCH$_2$CH$_2$—, —CH$_2$NHCH$_2$—, —CH$_2$CH$_2$NHCH$_2$—, —C(O)CH$_2$—, —C(O)CH$_2$—CH$_2$—, —CH$_2$C(O)CH$_2$—, —CH$_2$CH$_2$C(O)CH$_2$—, —CH$_2$CH$_2$C(O)CH$_2$CH$_2$—, —CH$_2$CH$_2$C(O)—, —CH$_2$CH$_2$CH$_2$C(O)NHCH$_2$CH$_2$NH—, —CH$_2$CH$_2$CH$_2$C(O)NHCH$_2$CH$_2$NHC(O)—, —CH$_2$CH$_2$CH$_2$C(O)NHCH$_2$CH$_2$NHC(O)CH$_2$—, —CH$_2$CH$_2$CH$_2$C(O)NHCH$_2$CH$_2$NHC(O)CH$_2$CH$_2$—, —OC(O)NH(CH$_2$)$_{0-6}$(OCH2CH2)$_{0-2}$—, —C(O)NH(CH$_2$)$_{1-6}$NHC(O)—, —NHC(O)NH(CH$_2$)$_{1-6}$—NH—C(O)—, —OC(O)CH$_2$—, —O—C(O)CH$_2$CH$_2$—, and —OC(O)CH$_2$CH$_2$CH$_2$—. In any of the above, a simple cycloalkylene group, e.g., 1,3- or 1,4-cyclohexylene, may replace any two, three, or four carbon alkylene group.

In another class of the first embodiment are those polymers and oligomers wherein Q is selected from the group consisting of:

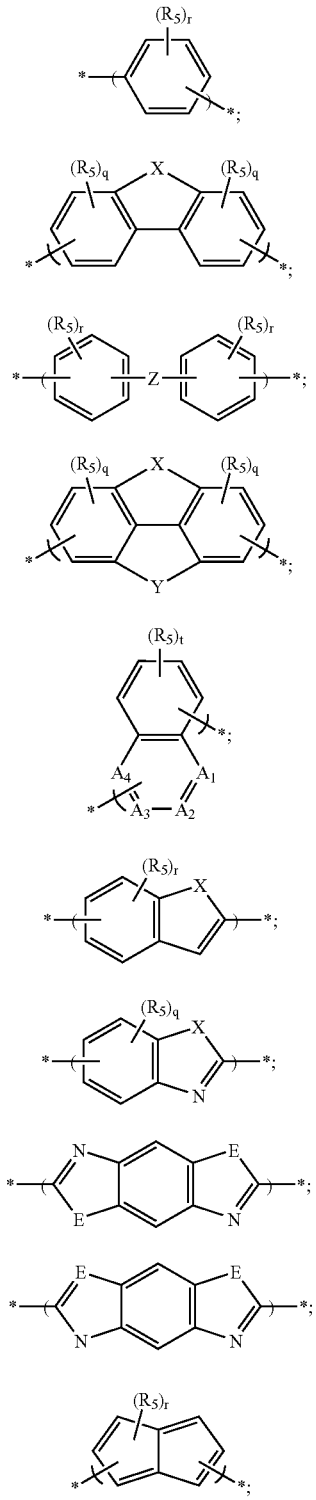

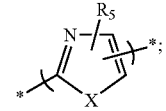

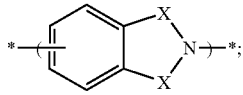

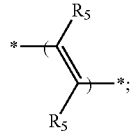

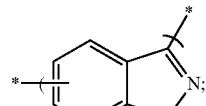

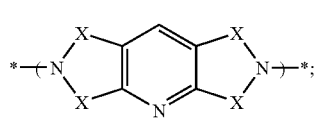

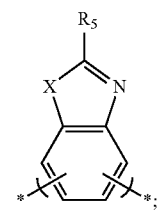

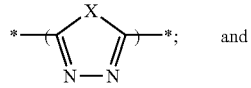

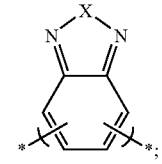

$R_5$ is independently selected from the group consisting of H, D, F, alkoxy, aryloxy, alkyl, alkaryl, heteroalkyl, aryl, aralkyl, heteroaryl, aryl, alkyl ketone, aryl ketone, alkylester, arylester, amide, carboxylic acid, fluoroalkyl, fluoroaryl, polyalkalene oxy, linear, dendrimeric or hyperbranched polymeric, and any two of adjacent (geminal, vicinal, or ortho) $R_5$ groups are optionally bridging; p is 0-2; q is 0-3; r is 0-4; s is 0-5; t is 0-6; X and Y are each independently selected from the group consisting of —O—, —S—, —NR$_6$—, and —CR$_6$R$_7$—, —CR$_6$R$_7$CR$_8$R$_9$—, —N=CR$_6$—, —CR$_6$=CR$_7$—, —N=N—, and —(CO)—; Z is selected from the group consisting of —O—, —S—, —NR$_6$—, aryl, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, oxazole, oxadiazole, thiazole, thiadiazole, substituted triazole, tetrazole, tetrazine, triazine, substituted triazine, linear, dendrimeric or hyperbranched polymeric, and —$CR_6R_7$—, —$CR_6R_7CR_8R_9$—, —N=$CR_6$—, $CR_6$=$CR_7$—, —N=N—, and —(CO)—; $R_6$, $R_7$, $R_8$, and $R_9$ are independently selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic, and any two of adjacent (geminal, vicinal, or ortho) $R_6$, $R_7$, $R_8$, and $R_9$ are optionally bridging; E is selected from the group consisting of O, NH, and S; $A_1$ is C, when group is linked at $A_1$, or $A_1$ is CH, $CR_1$, or N, when group is not linked at $A_1$; $A_2$ is C, when group is linked at $A_2$, or $A_2$ is CH, $CR_2$, or N, when group is not linked at $A_2$; $A_3$ is C, when group is linked at $A_3$, or $A_3$ is CH, $CR_3$, or N, when group is not linked at $A_3$; and $A_4$ is C, when group is linked at $A_4$, or $A_4$ is CH, $CR_4$, or N, when group is not linked at $A_4$.

In a subclass of this class are those polymers and oligomers wherein Q is

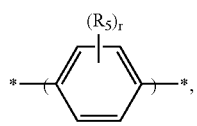

$R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent (geminal, vicinal, or ortho) $R_5$ groups are optionally bridging; and r is 0-4. In one instance of this subclass, Q is

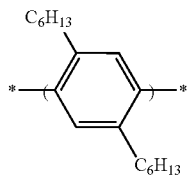 or 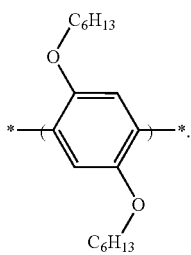

In another subclass of this class, are those polymers and oligomers wherein Q is

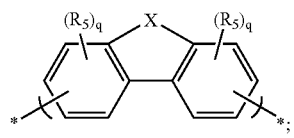

$R_5$ is each independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, and any two of adjacent (geminal, vicinal, or ortho) $R_5$ groups are optionally bridging; q is 0-3; X is selected from the group consisting of —O—, —S—, —$NR_6$—, and —$CR_6R_7$—, —$CR_6R_7CR_8R_9$—, —N=$CR_6$—, $CR_6$=$CR_7$—, —N=N—, and —(CO)—; and $R_6$, $R_7$, $R_8$, and $R_9$ are each independently selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic, and any two adjacent (geminal, vicinal, or ortho) $R_6$, $R_7$, $R_8$, and $R_9$ are optionally bridging.

In one instance of this subclass, Q is particularly

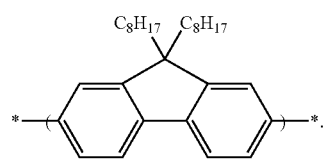

In another instance of this subclass Q is particularly

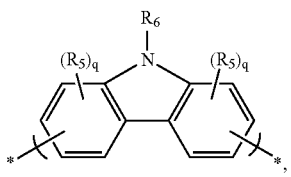

wherein: $R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, and any two of adjacent (geminal, vicinal, or ortho) $R_5$ groups are optionally bridging; q is 0-3, and $R_6$ is selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic; and more particularly, Q is

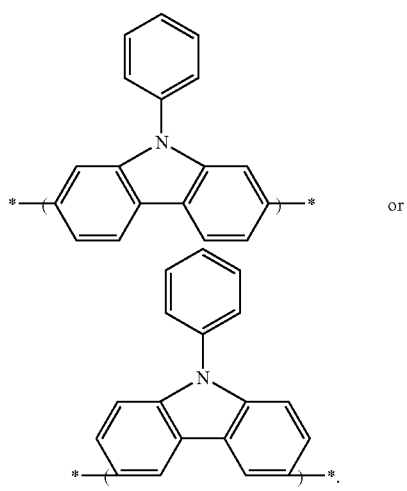 or

In another instance of this subclass Q is particularly

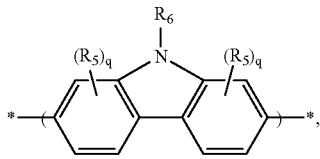

wherein: $R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, and any two of adjacent (geminal, vicinal, or ortho) $R_5$ groups are optionally bridging; q is 0-3, and $R_6$ is selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic.

In another subclass of this class, are those polymers and oligomers wherein Q is

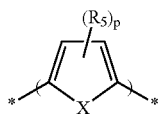

$R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent (geminal, vicinal, or ortho) $R_5$ groups are optionally bridging; p is 0-2; X is selected from the group consisting of —O—, —S—, —$NR_6$—, and $CR_6R_7$—, —$CR_6R_7CR_8R_9$—, —N═$CR_6$—, —$CR_6$═$CR_7$—, —N═N—, and —(CO)—; and $R_6$, $R_7$, $R_8$, and $R_9$ are independently selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic, and any two adjacent (geminal, vicinal, or ortho) of $R_6$, $R_7$, $R_8$, and $R_9$ are optionally bridging.

In another subclass of this class, are those polymers and oligomers wherein Q is

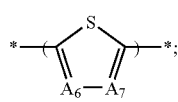

$A_6$ is CH, $CR_2$, or N; $A_7$ is CH, $CR_3$, or N; $R_2$ and $R_3$ are each independently selected from the group consisting of H, D, —$N_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and $R_2$ and $R_3$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzo furan; and $R_6$ and $R_7$ are each independently substituted or unsubstituted alkyl or aryl and are optionally bridging.

Within this subclass, Q is particularly

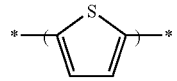

In another subclass of this class, are those polymers and oligomers wherein Q is

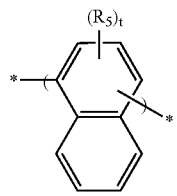

$R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, and any two of adjacent (geminal, vicinal, or ortho) $R_5$ groups are optionally bridging, and t is 0-6. Within this subclass, Q is particularly

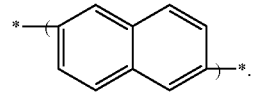

In another subclass of this class, are those polymers and oligomers wherein Q is

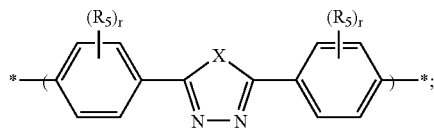

$R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent (geminal, vicinal, or ortho) $R_5$ groups are optionally bridging; r is 0-4; X is selected from the group consisting of —O—, —S—, —$NR_6$—, and —$CR_6R_7$—, —$CR_6R_7CR_8R_9$—, —N═$CR_6$—, $CR_6$═$CR_7$—, —N═N—, and —(CO)—; and $R_6$, $R_7$, $R_8$, and $R_9$ are each independently selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic, and any two of adjacent (geminal, vicinal, or ortho) $R_6$, $R_7$, $R_8$, and $R_9$ are optionally bridging. Within this subclass, Q is particularly

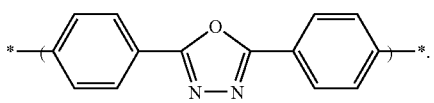

In another subclass of this class, are those polymers and oligomers wherein Q is

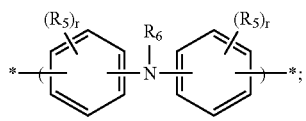

wherein $R_5$ is each independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent (geminal, vicinal, or ortho) $R_5$ groups are optionally bridging; $R_6$ is selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic; and r is 0-4. Within this subclass, Q is particularly

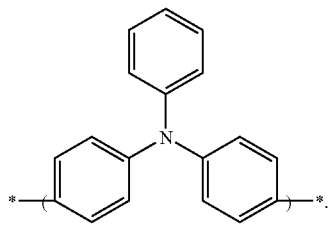

In another subclass of this class are those polymers and oligomers comprising (in addition at least one type of constitutional repeating unit selected from the group consisting of those represented by Formula IV, V, VI and VII) at least two additional and different types of constitutional repeating unit of Formula III represented below:

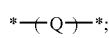 (III)

wherein at least one Q is selected from the group consisting of

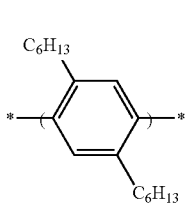 and 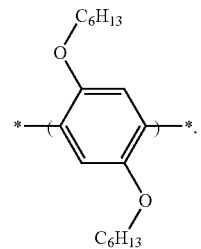.

In another instance are those polymers and oligomers comprising (in addition at least one type of constitutional repeating unit selected from the group consisting of those represented by Formula IV, V, VI and VII) at least two additional and different types of constitutional repeating unit of Formula III represented below:

 (III)

wherein at least one Q is selected from the group consisting of

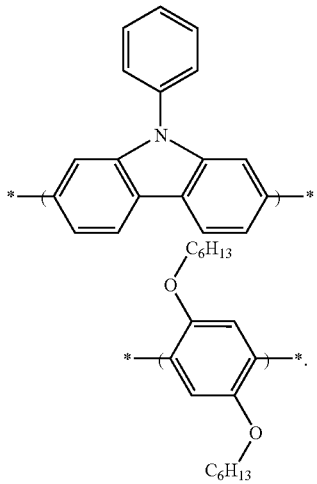 and

In another subclass of this class are those polymers and oligomers comprising (in addition at least one type of constitutional repeating unit selected from the group consisting of those represented by Formula IV, V, VI and VII) at least two additional and different types of constitutional repeating unit of Formula III represented below:

 (III)

wherein at least one Q is selected from the group consisting of

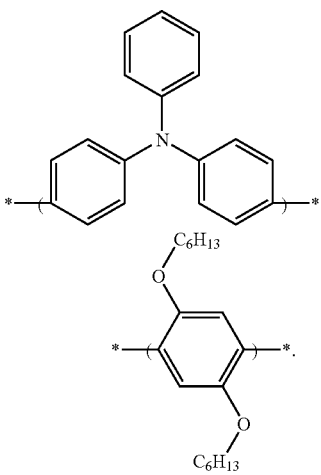 and

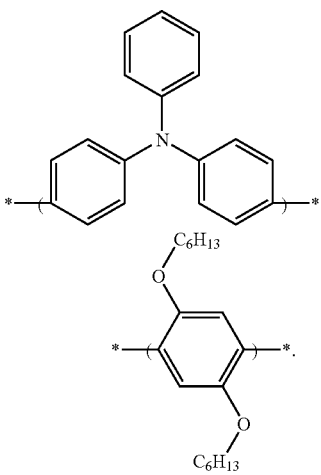.

In another subclass of this class are those polymers and oligomers comprising (in addition at least one type of constitutional repeating unit selected from the group consisting of those represented by Formula IV, V, VI and VII) at least two types of constitutional repeating unit of Formula III represented below:

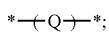 (III)

wherein at least one Q is selected from the group consisting of

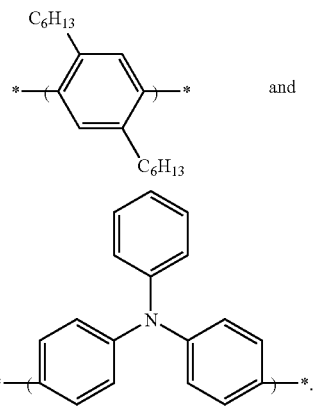

In another subclass of this class are those polymers and oligomers comprising (in addition at least one type of constitutional repeating unit selected from the group consisting of those represented by Formula IV, V, VI and VII) at least two types of constitutional repeating unit of Formula III represented below:

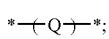 (III)

wherein at least one Q is selected from the group consisting of

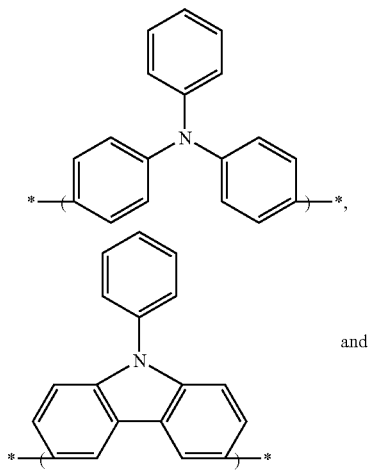

-continued

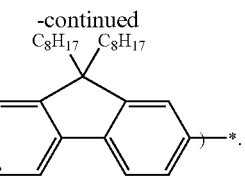

In another subclass of this class are those polymers and oligomers comprising (in addition at least one type of constitutional repeating unit selected from the group consisting of those represented by Formula IV, V, VI and VII) at least three additional and different types of constitutional repeating unit of Formula III represented below:

*—(Q)—* (III)

wherein at least one Q is selected from the group consisting of

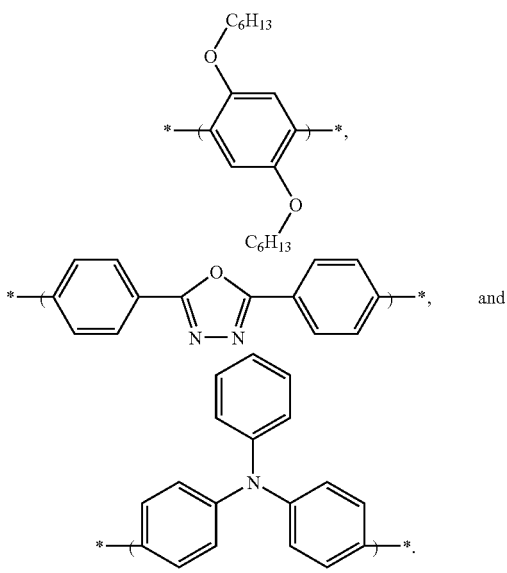

In another class of the first embodiment are those polymers and oligomers comprising a constitutional repeating unit selected from the group consisting of

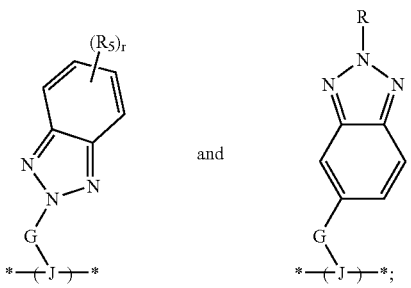

wherein $R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent (geminal, vicinal, or ortho) $R_5$ groups are optionally bridging; J is a trivalent moiety selected from the group consisting of 1,2,4-phenylenetriyl and >$CR_6CR_7R_8$—; G is nil or is selected from the group consisting of —Ar—, —O—, —S—, —$NR_1$—, $CR_2R_3$—, —$CR_1R_2CR_3R_4$—, N=$CR_1$—, $CR_1$=$CR_2$—, —N=N—, —(CO)—, $C_3$ to $C_{30}$ alkyldiyl, and $C_3$ to $C_{30}$ heteroalkyldiyl; $R_1$, $R_2$, $R_3$, $R_4$ are each independently selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and any two of adjacent (geminal, vicinal, or ortho) $R_1$, $R_2$, $R_3$ or $R_4$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; $R_6$, $R_7$, and $R_8$ are each independently substituted or unsubstituted alkyl or aryl; and any two adjacent (geminal, vicinal, or ortho) $R_6$, $R_7$, $R_8$, are optionally bridging; Ar is unsubstituted or substituted, single or multiple ring, fused or non-fused aromatic or heteroaromatic; and r is 0-4. In a subclass of this class J is particularly >$CHCH_2$—.

In another class of the first embodiment are those polymers and oligomers comprising a constitutional repeating unit selected from the group consisting of

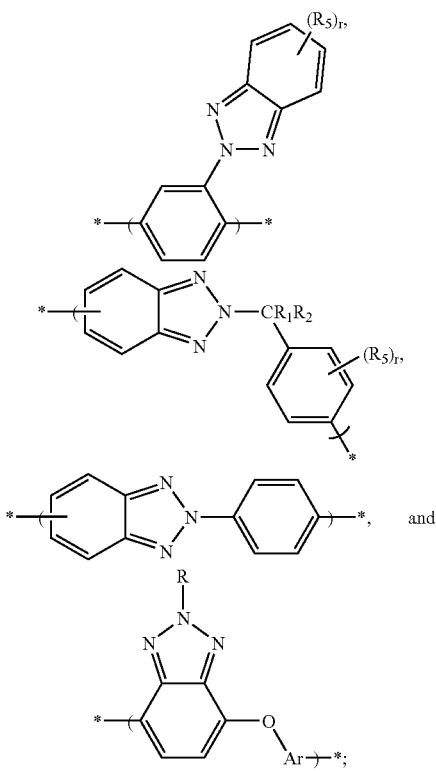

wherein R is H, D, alkyl, alkaryl, heteroalkyl, aryl, aralkyl, heteroaryl, alkyl ketone, aryl ketone, alkylester, arylester, amide, carboxylic acid, phenol, 2-hydroxyphenyl, 2-alkoxyphenyl, 2-aryloxyphenyl, substituted 2-hydroxyphenyl, substituted 2-alkoxyphenyl, substituted 2-aryloxyphenyl, fluoroalkyl, or fluoroaryl; $R_1$ and $R_2$ are each independently selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; $R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two adjacent (geminal, vicinal, or ortho) $R_5$ groups are optionally bridging; $R_6$ and $R_7$ are each independently substituted or unsubstituted alkyl or aryl, and are optionally bridging; Ar is unsubstituted or substituted, single or multiple ring, fused or non-fused aromatic or heteroaromatic; and r is 0-4.

In another class of the first embodiment are those polymers and oligomers comprising a constitutional repeating unit selected from the group consisting of

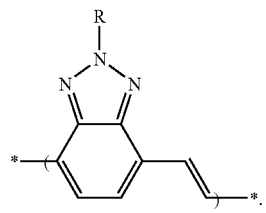

In another class of the first embodiment of the present invention are those polymers and oligomers comprising (a) from about 0.001 to about 100 mol % of at least one constitutional repeating unit of the general formula selected from the group consisting of Formula I and Formula II, and (b) from about 0 to about 99.999 mol % of at least one constitutional repeating unit of the general formula represented by Formula III.

In another class of the first embodiment of the present invention are those polymers and oligomers comprising (a) from about 1 to about 100 mol % of at least one constitutional repeating unit of the general formula selected from the group consisting of Formula I and Formula II, and (b) from about 0 to about 99 mol % of at least one constitutional repeating unit of the general formula represented by Formula III.

In another class of the first embodiment of the present invention are those polymers and oligomers comprising (a) from about 25 mol % of at least one constitutional repeating unit of the general formula selected from the group consisting of Formula I and Formula II, and (b) about 75 mol % of at least one constitutional repeating unit of the general formula represented by Formula III.

In another class of the first embodiment of the present invention are those polymers and oligomers comprising (a) from about 20 mol % of at least one constitutional repeating unit of the general formula selected from the group consisting of Formula I and Formula II, and (b) about 80 mol % of at least one constitutional repeating unit of the general formula represented by Formula III.

In another class of the first embodiment of the present invention are those polymers and oligomers comprising (a) from about 40 mol % of at least one constitutional repeating unit of the general formula selected from the group consisting of Formula I and Formula II, and (b) about 60 mol % of at least one constitutional repeating unit of the general formula represented by Formula III.

In another class of the first embodiment of the present invention are those polymers and oligomers comprising (a) from about 50 mol % of at least one constitutional repeating unit of the general formula selected from the group consisting of Formula I and Formula II, and (b) about 50 mol % of at least one constitutional repeating unit of the general formula represented by Formula III.

In another class of the first embodiment of the present invention are those polymers having a weight average molecular weight $M_W$ of at least about 15,000 Daltons, and more particularly of at least about 20,000 Daltons, at least about 40,000 Daltons, at least about 60,000 Daltons, at least about 80,000 Daltons, or at least about 100,000 Daltons.

In another class of the first embodiment of the present invention are those oligomers having a weight average molecular weight $M_W$ of from about 200 to about 15000 Daltons.

In another class of the first embodiment of the present invention are those polymers and oligomers which are copolymers or cooligomers, block co-polymers or cooligomers, random co-polymers or cooligomers, crosslinked polymers or cooligomers, hyperbranched co-polymers or cooligomers, dendritic co-polymers or cooligomers, or star co-polymers or cooligomers.

In another class of the first embodiment of the present invention are those polymers and oligomers which are photoluminescent and/or electroluminescent.

In another class of the first embodiment of the present invention are those polymers and oligomers suitable for excitation in the UV, visible, or infrared region.

In another class of the first embodiment of the present invention are those polymers and oligomers capable of emitting light having a wavelength in the range 350-750 nanometers, more particularly 450-700 nm, even more particularly 500-650 nm.

In a second embodiment the present invention provides a process of preparing a polymer or oligomer comprising (a) admixing (i) at least one compound selected from the group consisting of Formula VIII, Formula IX, and Formula X, represented below

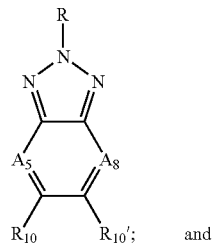

(VIII)

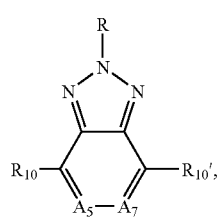

(IX)

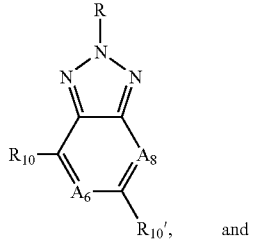

and

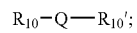

-continued (X)

and (ii) optionally, at least one compound of the general formula represented below by Formula XI:

$$R_{10}-Q-R_{10}';$$ (XI)

wherein R is H, D, alkyl, alkaryl, heteroalkyl, aryl, aralkyl, heteroaryl, alkyl ketone, aryl ketone, alkylester, arylester, amide, carboxylic acid, phenol, 2-hydroxyphenyl, 2-alkoxyphenyl, 2-aryloxyphenyl, substituted 2-hydroxyphenyl, substituted 2-alkoxyphenyl, substituted 2-aryloxyphenyl, fluoroalkyl, or fluoroaryl; $A_5$ is CH, $CR_1$, or N; $A_6$ is CH, $CR_2$, or N; $A_7$ is CH, $CR_3$, or N; $A_8$ is CH, $CR_4$, or N; $R_1, R_2, R_3, R_4$ are each independently selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and any two of adjacent (geminal, vicinal, or ortho) $R_1, R_2, R_3$ or $R_4$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; Q is selected from the group consisting of —Ar—, —O—, —S—, —$NR_1$—, —$OCR_1R_2$—, —$CR_1R_2$—, —$OCR_1R_2CR_3R_4$—, —$CR_1R_2CR_3R_4$—, —N=$CR_1$—, —$CR_1$=N—, —$CR_1$=$CR_2$—, —N=N—, and —(CO)—, —$BR_1$—, $SiR_1R_2$—, —(CO)—O—, —O—(CO)—, —$NR_1$—(CO)—, and —(CO)—$NR_1$—, $C_3$ to $C_{30}$ alkyldiyl, and $C_3$ to $C_{30}$ heteroalkyldiyl; $R_6$ and $R_7$ are each independently substituted or unsubstituted alkyl or aryl, and $R_6$ and $R_7$ are optionally bridging; Ar is unsubstituted or substituted, single or multiple ring, fused or non-fused aromatic or heteroaromatic; and $R_{10}$ and $R_{10}'$ are each independently a group or groups capable of participating in aryl to aryl and/or aryl to alkyl coupling reaction; and (b) adding a polymerization catalyst and optional co-reactants into the mixture to cause: (i) polymerization to form a carbon to carbon bond linking at least one compound selected from the group consisting of Formula VIII, Formula IX, and Formula X with at least one other compound selected from the group consisting of Formula VIII, Formula IX, and Formula X; and/or (ii) polymerization to form a carbon to carbon bond linking at least one compound selected from the group consisting of Formula VIII, Formula IX, and Formula X with at least one compound of Formula XI.

In a class of the second embodiment are those processes wherein $R_{10}$ and $R_{10}'$ are each independently a group or groups selected from the group consisting of H, D, halide, —Si(R$_{11}$)$_3$, —Sn(R$_{11}$)$_3$, —Cu, —Cu(CN)Li, —Li, —MgBr, —ZnCl, —ZnBr, —ZnI, —MnBr, —MnCl, —MnI, —HgCl, —OTf, —SH, —SO$_3$CH$_3$, —B(OR$_{12}$)$_2$; R$_{11}$ is each independently selected from the group consisting of halide, hydroxyl, alkyl, and alkyloxy; and R$_{12}$ is each independently selected from the group consisting of H, D, alkyl, and aryl or the two R$_{12}$ taken together with the oxygen atoms to which they are connected form cyclic boronic acid esters.

In another class of the second embodiment are those processes employing aryl to aryl coupling reaction selected from the group consisting of Suzuki, Colon, Stille, Yamamoto (stoichiometric and catalytic).

In another class of the second embodiment of the present invention are those processes comprising admixing (i) at least one compound of Formula XII represented below:

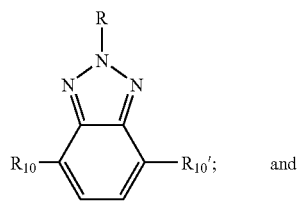

(XII)

and (ii) at least one compound of the general formula represented below by Formula XI:

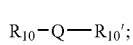

(XI)

wherein: R is H, D, alkyl, alkaryl, heteroalkyl, aryl, aralkyl, heteroaryl, alkyl ketone, aryl ketone, alkylester, arylester, amide, carboxylic acid, phenol, 2-hydroxyphenyl, 2-alkoxyphenyl, 2-aryloxyphenyl, substituted 2-hydroxyphenyl, substituted 2-alkoxyphenyl, substituted 2-aryloxyphenyl, fluoroalkyl, or fluoroaryl; R$_{10}$ and R$_{10}$' are each independently a group or groups capable of participating in aryl to aryl and/or aryl to alkyl coupling reaction; and Q is selected from the group consisting of —Ar—, —O—, —S—, —NR$_1$—, —OCR$_1$R$_2$—, —CR$_1$R$_2$—, —OCR$_1$R$_2$CR$_3$R$_4$—, —CR$_1$R$_2$CR$_3$R$_4$—, —N═CR$_1$—, —CR$_1$═N—, —CR$_1$═CR$_2$—, —N═N—, and —(CO)—, —BR$_1$—, SiR$_1$R$_2$—, —(CO)—O—, —O—(CO)—, —NR$_1$—(CO)—, and —(CO)—NR$_1$—, C$_3$ to C$_{30}$ alkyldiyl, and C$_3$ to C$_{30}$ heteroalkyldiyl; R$_1$, R$_2$, R$_3$, R$_4$ are each independently selected from the group consisting of H, D, —NR$_6$R$_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and any two of adjacent (geminal, vicinal, or ortho) R$_1$, R$_2$, R$_3$ or R$_4$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; and Ar is unsubstituted or substituted, single or multiple ring, fused or non-fused aromatic or heteroaromatic.

In a subclass of this class are those polymers and oligomers wherein R is

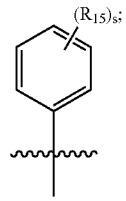

s is 0-5; R$_{15}$ is selected from the group consisting of H, D, —NR$_6$R$_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and when s is 2-5, any two of adjacent (geminal, vicinal, or ortho) R$_{15}$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; and R$_6$ and R$_7$ are each independently substituted or unsubstituted alkyl or aryl and are optionally bridging.

In another subclass of this class are those polymers and oligomers wherein R is selected from the group consisting of:

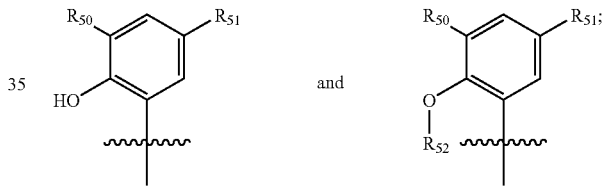

and

R$_{50}$ and R$_{51}$ are each independently selected from the group consisting of H, D, F, alkyl, alkaryl, heteroalkyl, aryl, aralkyl, heteroaryl, fluoroalkyl, fluoroaryl, amide, and ester; and R$_{52}$ is selected from the group consisting of alkyl, aryl, heteroaryl, fluoroalkyl, and fluoroaryl. Particularly, R is selected from the group consisting of:

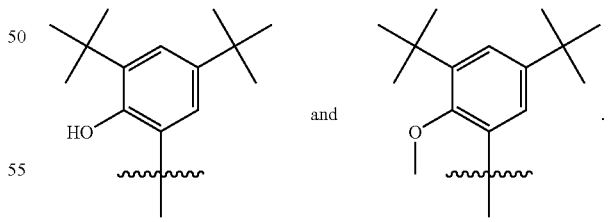

and

In another subclass of this class are those polymers and oligomers wherein R is alkyl. In a subclass of this class are those polymers and oligomers wherein R is n-hexyl.

In one instance are those processes wherein R$_{10}$ and R$_{10}$' in Formula X are each independently a halide, and particularly wherein R$_{10}$ and R$_{10}$' in Formula X are each a bromide.

In another class of the second embodiment of the present invention are those processes wherein R$_{10}$ and R$_{10}$' in formula X are each independently

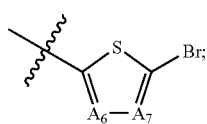

$A_6$ is CH, $CR_2$, or N; $A_7$ is CH, $CR_3$, or N; $R_2$ and $R_3$ are each independently selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and $R_2$ and $R_3$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; and $R_6$ and $R_7$ are each independently substituted or unsubstituted alkyl or aryl and are optionally bridging.

In a subclass of this class are those processes wherein $R_{10}$ and $R_{10}'$ in formula X are each

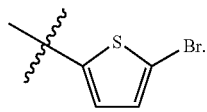

In another class of the second embodiment of the present invention are those processes comprising admixing (in addition to at least one compound selected from the group consisting of those represented by Formula VIII, IX, X or XII) (i) at least one compound of Formula XI wherein Q in Formula XI is

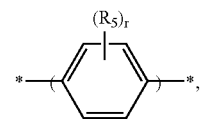

$R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent (geminal, vicinal, or ortho) $R_5$ groups are optionally bridging; r is 0-4; $R_{10}$ and $R_{10}'$ in Formula XI are each independently —$B(OR_{12})_2$; $R_{12}$ is each independently selected from the group consisting of H, D, alkyl, and aryl, or the two $R_{12}$ taken together with the oxygen atoms to which they are connected form cyclic boronic acid esters; and/or (ii) at least one (different from that in (i)) compound of Formula XI wherein Q in Formula XI is selected from the group consisting of

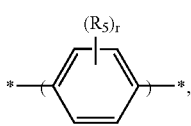

(a)

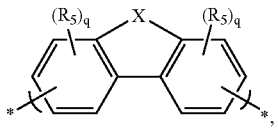

(b)

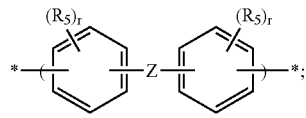

(c)

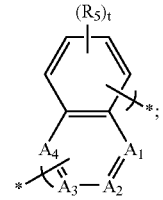

(d)

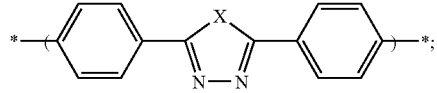

(e)

wherein $R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent (geminal, vicinal, or ortho) $R_5$ groups are optionally bridging; q is 0-3; r is 0-4; t is 0-6; X is selected from the group consisting of —O—, —S—, —$NR_6$—, and —$CR_6R_7$—, —$CR_6R_7CR_8R_9$—, —N=$CR_6$—, —$CR_6$=$CR_7$—, —N=N—, and —(CO)—; Z is selected from the group consisting of —O—, —S—, —$NR_6$—, aryl, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, oxazole, oxadiazole, thiazole, thiadiazole, substituted triazole, tetrazole, tetrazine, triazine, substituted triazine, linear, dendrimeric or hyperbranched polymeric, and —$CR_6R_7$—, —$CR_6R_7CR_8R_9$—, N=$CR_6$—, $CR_6$=$CR_7$—, —N=N—, and —(CO)—; $R_6$, $R_7$, $R_8$, and $R_9$ are independently selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic, and any two of adjacent (geminal, vicinal, or ortho) $R_6$, $R_7$, $R_8$, and $R_9$ are optionally bridging; and $R_{10}$ and $R_{10}'$ in Formula XI are each independently a halide.

In a subclass of this class are those processes comprising admixing (i) at least one compound of Formula XI wherein Q in Formula XI is selected from the group consisting of

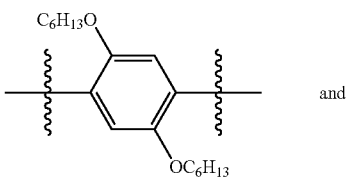 and

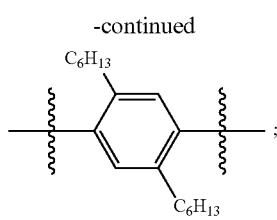

$R_{10}$ and $R_{10}'$ in Formula XI are each independently —B(OR$_{12}$)$_2$; R$_{12}$ is each independently selected from the group consisting of H, D, alkyl, and aryl, or the two R$_{12}$ taken together with the oxygen atoms to which they are connected form cyclic boronic acid esters; and (ii) at least one compound (different from that provided in (i)) of Formula XI wherein Q in Formula XI is selected from the group consisting of

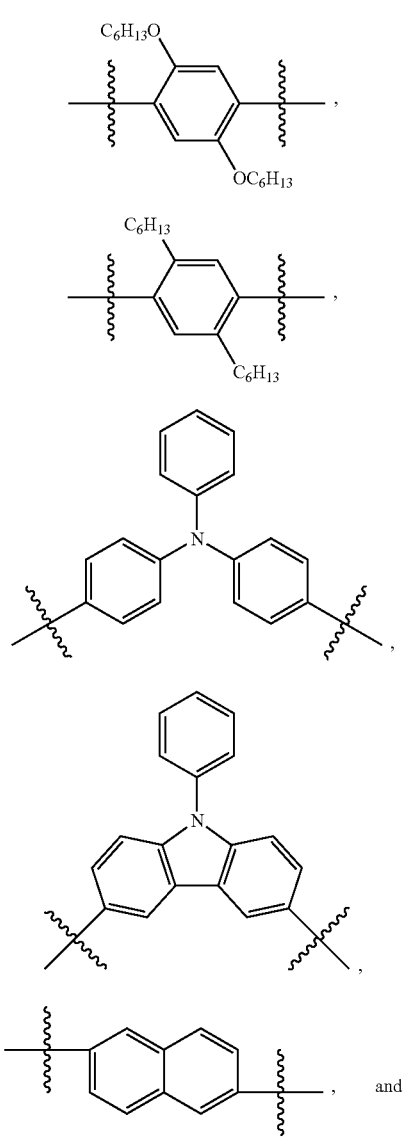

$R_{10}$ and $R_{10}'$ in Formula XI are each independently a bromide.

In one instance of this subclass are those processes comprising admixing (i) at least one compound of Formula XI wherein Q in Formula XI is

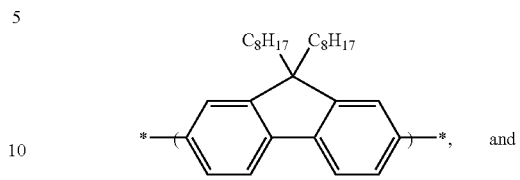

$R_{10}$ and $R_{10}'$ in Formula XI are each independently —B(OR$_{12}$)$_2$; R$_{12}$ is each independently selected from the group consisting of H, D, alkyl, and aryl, or the two R$_{12}$ taken together with the oxygen atoms to which they are connected form cyclic boronic acid esters.

Within this instance are particularly those processes comprising admixing (i) at least one compound of Formula XI wherein Q in Formula XI is

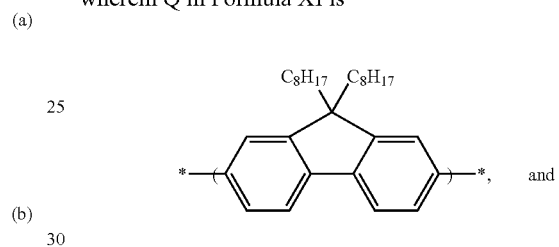

$R_{10}$ and $R_{10}'$ are each a bromide.

In a class of this embodiment of the present invention are those processes comprising as polymerization initiator a palladium catalyst selected from the group consisting of Pd(PPh$_3$)$_4$, Pd(OAc)$_2$, PdCl$_2$(dppb), and Pd(dba)$_2$/PPh$_3$, in combination with a base.

In a subclass of this class, the base is selected from the group consisting of Na$_2$CO$_3$ and K$_2$CO$_3$, NaHCO$_3$, KHCO$_3$, CsOH, CsHCO$_3$, Cs$_2$CO$_3$, Ba(OH)$_2$, KOH, and NaOH.

The third embodiment provides for an electronic device or a component therefor comprising: (a) an anode; (b) a cathode; and (c) a light-emissive layer for accepting and combining positive and negative charge carriers from adjacent layers to generate light; and optionally: (d) a hole injection layer; (e) one or more hole transport layers; (f) one or more electron transport layers; (g) an electron injection layer; and (h) a buffer layer; wherein said light-emissive layer and/or one or more of said hole and/or electron transport layers comprises a polymer or oligomer described herein.

In a class of the third embodiment of the present invention are those electronic devices which comprise an electroluminescent device.

The fourth embodiment of the present invention provides a light emitting device or a component therefor comprising a polymer or oligomer described herein.

In one class of the fourth embodiment are electroluminescent devices. In another class of the fourth embodiment are photoluminescent devices. In another class of the fourth embodiment is an organic light emitting diode (OLED). In a subclass of this class the OLED has a turn on voltage of less than about 5 Volts and more particularly of about 3 Volts. In another subclass of this class the OLED has a light emission efficiency of at least 2.5 lm/W at 7V and 1000 cd/m$^2$, or of at least 4.0 lm/W at 4V and 1000 cd/m$^2$, or of at least 0.2 lm/W at 10 V and 100 cd/m$^2$.

In another class of the fourth embodiment is an organic light emitting diode (OLED) display. In yet another class of the fourth embodiment is a sensor. In yet another class of the fourth embodiment the device exhibits photoluminescence with a quantum efficiency that is greater than 10 percent.

The fifth embodiment provides an electronic device or a component therefor comprising: (a) an anode; (b) a cathode; and (c) a light-emissive layer for accepting and combining positive and negative charge carriers from adjacent layers to generate light; and optionally: (d) a hole injection layer; (e) one or more hole transport layers; (f) one or more electron transport layers; (g) an electron injection layer; and (h) a buffer layer; wherein said light-emissive layer and/or one or more of said hole and/or electron transport layers comprises a compound of formula:

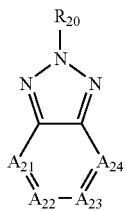

wherein $R_{20}$ is H, D, alkyl, alkaryl, heteroalkyl, aryl, aralkyl, heteroaryl, alkyl ketone, aryl ketone, alkylester, arylester, amide, carboxylic acid, phenol, 2-hydroxyphenyl, 2-alkoxyphenyl, 2-aryloxyphenyl, substituted 2-hydroxyphenyl, substituted 2-alkoxyphenyl, substituted 2-aryloxyphenyl, fluoroalkyl, or fluoroaryl; $A_{21}$ is CH, $CR_{21}$, or N; $A_{22}$ is CH, $CR_{22}$, or N; $A_{23}$ is CH, $CR_{23}$, or N; $A_{24}$ is CH, $CR_{24}$, or N; and $R_{21}$, $R_{22}$, $R_{23}$, $R_{24}$ are each independently selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, or $R_1$ and $R_2$, and/or $R_2$ and $R_3$, and/or $R_3$ and $R_4$ taken together with the two carbons to which each is respectively attached form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran.

In the first class of the fifth embodiment are those electronic devices and components therefor wherein $R_{20}$ is

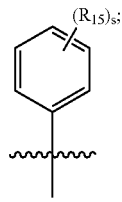

s is 0-5; $R_{15}$ is selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and when s is 2-5, any two of adjacent (geminal, vicinal, or ortho) $R_{15}$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; and $R_6$ and $R_7$ are each independently substituted or unsubstituted alkyl or aryl and are optionally bridging.

In a subclass of this class are those electronic devices or components therefor wherein $R_{20}$ is selected from the group consisting of:

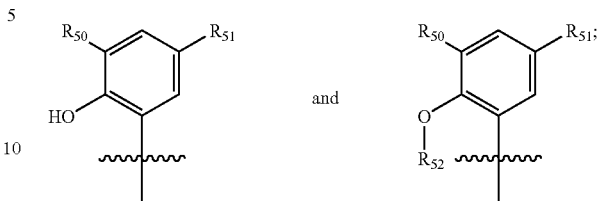

$R_{50}$ and $R_{51}$ are each independently selected from the group consisting of H, D, F, alkyl, alkaryl, heteroalkyl, aryl, aralkyl, heteroaryl, fluoroalkyl, fluoroaryl, amide, and ester; and $R_{52}$ is selected from the group consisting of alkyl, aryl, heteroaryl, fluoroalkyl, and fluoroaryl.

In one instance of this subclass are those electronic devices wherein $R_{20}$ is selected from the group consisting of:

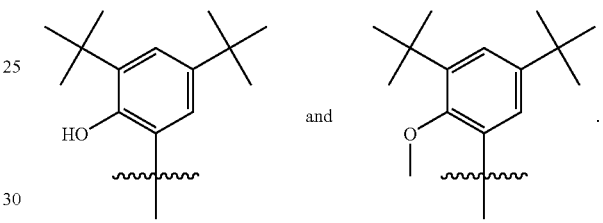

In the second class of the fifth embodiment are those electronic devices wherein $R_{20}$ is alkyl. In a subclass of this class are those electronic devices wherein $R_{20}$ is n-hexyl.

In another class of the fifth embodiment are those electronic devices or components therefor wherein $R_{21}$, $R_{22}$, $R_{23}$, $R_{24}$ are each independently selected from the group consisting of:

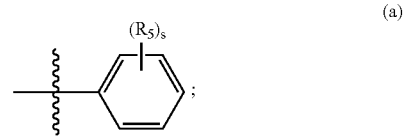

(a)

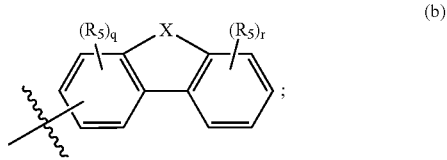

(b)

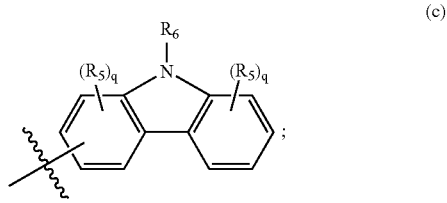

(c)

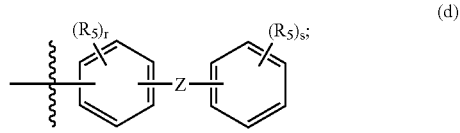

(d)

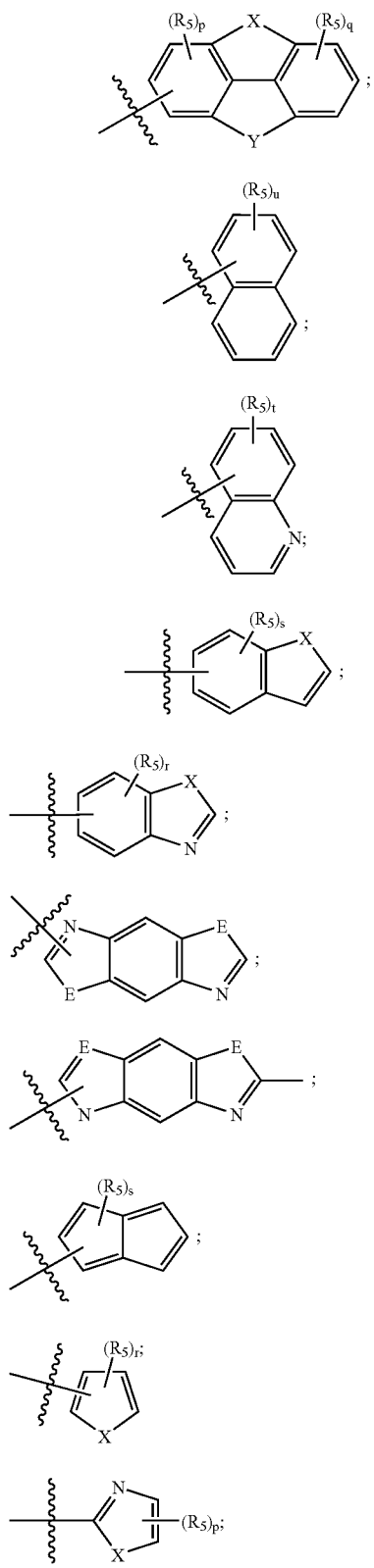
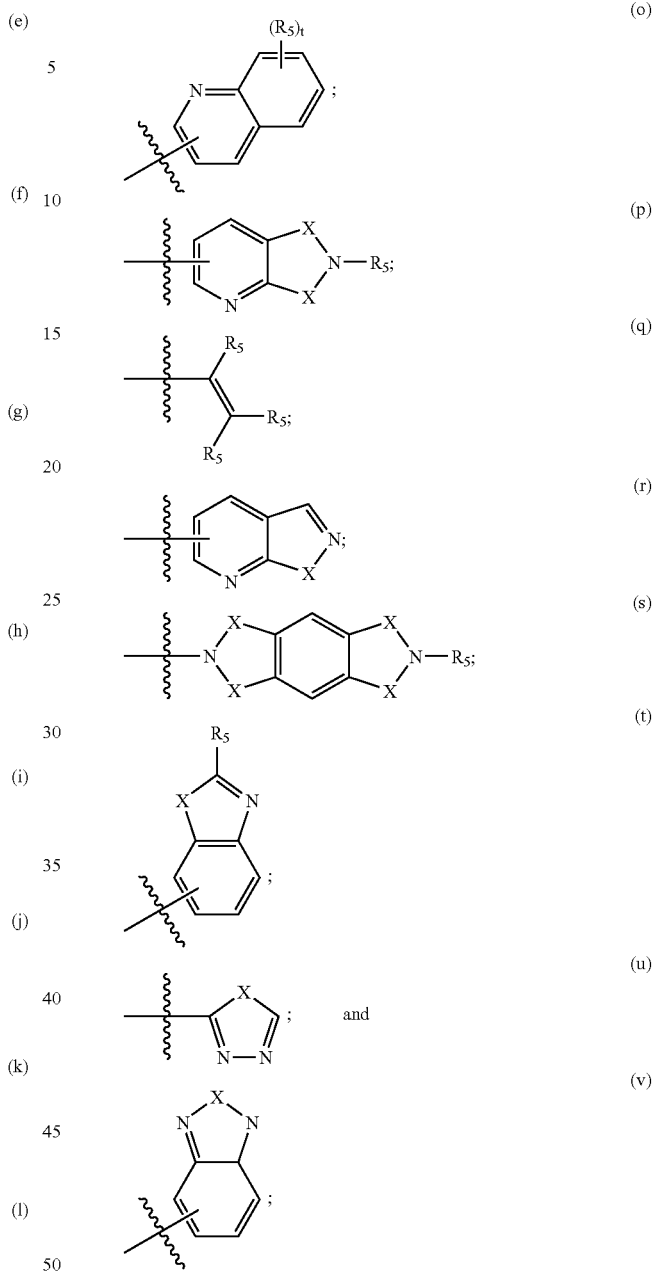

wherein: $R_5$ is independently selected from the group consisting of H, D, F, alkoxy, aryloxy, alkyl, alkaryl, heteroalkyl, aryl, aralkyl, heteroaryl, aryl, alkyl ketone, aryl ketone, alkylester, arylester, amide, carboxylic acid, fluoroalkyl, fluoroaryl, polyalkalene oxy, linear, dendrimeric or hyperbranched polymeric, and any two of adjacent (geminal, vicinal, or ortho) $R_5$ groups are optionally bridging; p is 0-2; q is 0-3; r is 0-4; s is 0-5; t is 0-6; X and Y are each independently selected from the group consisting of —O—, —S—, —$NR_6$—, and —$CR_6R_7$—, —$CR_6R_7CR_8R_9$—, —N=$CR_6$—, —$CR_6$=$CR_7$—, —N=N—, and —(CO)—; Z is selected from the group consisting of —O—, —S—, —$NR_6$—, aryl, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, oxazole, oxadiazole, thiazole, thiadiazole, substituted triazole, tetrazole, tetrazine, triazine, substituted triazine, linear, dendrimeric or hyperbranched polymeric, and —$CR_6R_7$—, —$CR_6R_7CR_8R_9$—, $N{=}CR_6$—, $CR_6{=}CR_7$—, —$N{=}N$—, and —(CO)—; $R_6$, $R_7$, $R_8$, and $R_9$ are independently selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic, and any two of adjacent (geminal, vicinal, or ortho) $R_6$, $R_7$, $R_8$, and $R_9$ are optionally bridging; and E is selected from the group consisting of O, NH, and S.

In a subclass of this class are those electronic devices or components therefor wherein $R_{21}$, $R_{22}$, $R_{23}$, $R_{24}$ are each independently selected from the group consisting of: 4-(dimethylamino)phenyl, thiophen-2-yl, and 9,9-dihexyl-9H-fluoren-7-yl.

In another subclass of this class the those electronic devices which comprise an electroluminescent device.

The sixth embodiment of the present invention provides a sensor comprising a compound of formula:

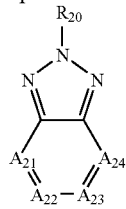

wherein: $R_{20}$ is H, D, alkyl, alkaryl, heteroalkyl, aryl, aralkyl, heteroaryl, alkyl ketone, aryl ketone, alkylester, arylester, amide, carboxylic acid, phenol, 2-hydroxyphenyl, 2-alkoxyphenyl, 2-aryloxyphenyl, substituted 2-hydroxyphenyl, substituted 2-alkoxyphenyl, substituted 2-aryloxyphenyl, fluoroalkyl, or fluoroaryl; $A_{21}$ is CH, $CR_{21}$, or N; $A_{22}$ is CH, $CR_{22}$, or N; $A_{23}$ is CH, $CR_{23}$, or N; $A_{24}$ is CH, $CR_{24}$, or N; and $R_{21}$, $R_{22}$, $R_{23}$, $R_{24}$ are each independently selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, or $R_{21}$ and $R_{22}$, and/or $R_{22}$ and $R_{23}$, and/or $R_{23}$ and $R_{24}$ taken together with the two carbons to which each is respectively attached form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran.

In one class of the sixth embodiment are those sensors comprising a compound of formula:

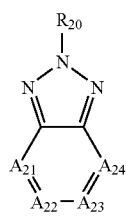

wherein $R_{20}$ is

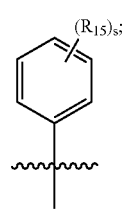

s is 0-5; $R_{15}$ is selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and when s is 2-5, any two of adjacent (geminal, vicinal, or ortho) $R_{15}$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; and $R_6$ and $R_7$ are each independently substituted or unsubstituted alkyl or aryl and are optionally bridging.

In a subclass of this class are those sensors are those sensors comprising a compound of formula:

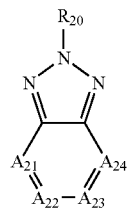

wherein $R_{20}$ is selected from the group consisting of:

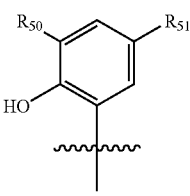 and 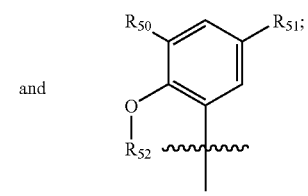

$R_{50}$ and $R_{51}$ are each independently selected from the group consisting of H, D, F, alkyl, alkaryl, heteroalkyl, aryl, aralkyl, heteroaryl, fluoroalkyl, fluoroaryl, amide, and ester; and $R_{52}$ is selected from the group consisting of alkyl, aryl, heteroaryl, fluoroalkyl, and fluoroaryl.

In one instance of this subclass are those sensors comprising a compound of formula:

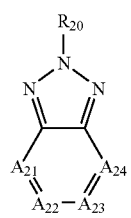

wherein $R_{20}$ is

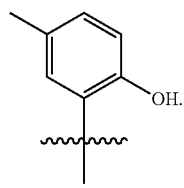

The seventh embodiment provides compounds of the general formula:

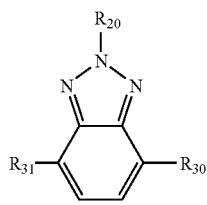

wherein: $R_{20}$ is selected from the group consisting of H, D, alkyl, alkaryl, heteroalkyl, aryl, aralkyl, heteroaryl, alkyl ketone, aryl ketone, alkylester, arylester, amide, carboxylic acid, phenol, 2-hydroxyphenyl, 2-alkoxyphenyl, 2-aryloxyphenyl, substituted 2-hydroxyphenyl, substituted 2-alkoxyphenyl, substituted 2-aryloxyphenyl, fluoroalkyl, or fluoroaryl; except that $R_{20}$ is not methyl; and $R_{30}$ and $R_{31}$ are each independently a halide.

In a class of the seventh embodiment are those compounds, wherein $R_{20}$ is

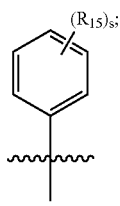

s is 0-5; $R_{15}$ is selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and when s is 2-5, any two of adjacent (geminal, vicinal, or ortho) $R_{15}$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; and $R_6$ and $R_7$ are each independently substituted or unsubstituted alkyl or aryl and are optionally bridging.

In a subclass of this class are those compounds, wherein $R_{20}$ is selected from the group consisting of:

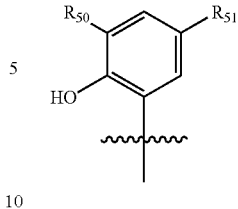 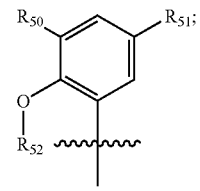

$R_{50}$ and $R_{51}$ are each independently selected from the group consisting of H, D, F, alkyl, alkaryl, heteroalkyl, aryl, aralkyl, heteroaryl, fluoroalkyl, fluoroaryl, amide, and ester; and $R_{52}$ is selected from the group consisting of alkyl, aryl, heteroaryl, fluoroalkyl, and fluoroaryl.

In one instance of this subclass are those compounds wherein $R_{20}$ is selected from the group consisting of:

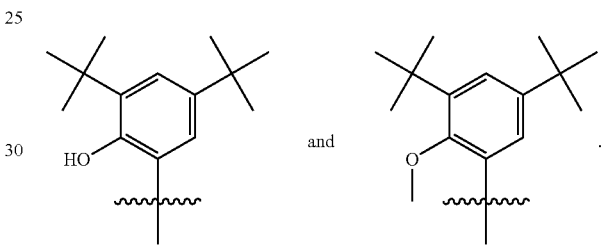

In the second class of the seventh embodiment are those compounds wherein $R_{20}$ is alkyl. In a subclass of this class are those compounds wherein $R_{20}$ is n-hexyl.

In a class of the seventh embodiment are those compounds, wherein $R_{10}$ and $R_{10}'$ are each independently a bromide, and more particularly wherein $R_{10}$ and $R_{10}'$ are each a bromide.

In the third class are those compounds selected from the group consisting of: (a) 4,7-dibromo-2-hexyl-2H-benzo[d][1,2,3]triazole, (b) 4,6-dibromo-2-hexyl-2H-benzo[d][1,2,3]triazole, (c) 5,6-dibromo-2-hexyl-2H-benzo[d][1,2,3]triazole, (d) 2,4-di-tert-butyl-6-(4,7-dibromo-2H-benzo[d][1,2,3]triazol-2-yl)phenol, (e) 2,4-di-tert-butyl-6-(4,6-dibromo-2H-benzo[d][1,2,3]triazol-2-yl)phenol, (f) 2,4-di-tert-butyl-6-(5,6-dibromo-2H-benzo[d][1,2,3]triazol-2-yl)phenol, (g) 2-(3,5-di-tert-butyl-2-methoxyphenyl)-4,7-dibromo-2H-benzo[d][1,2,3]triazole, (h) 2-(3,5-di-tert-butyl-2-methoxyphenyl)-4,6-dibromo-2H-benzo[d][1,2,3]triazole, and (i) 2-(3,5-di-tert-butyl-2-methoxyphenyl)-5,6-dibromo-2H-benzo[d][1,2,3]triazole.

The discovery of the embodiments described herein is based in part on the observation that although the known heretofor examples of 2-hydroxyphenylbenzotriazoles do not fluoresce after absorption of light because they revert from an excited energy state back to the ground state via a fast chemical reaction (proton hopping), if appropriate substituents for the 2-hydroxyphenylbenzotriazoles are used, the first excited state energy level is lowered to the point where the proton hopping cannot be sustained, and as a result good fluorescence is observed. Additionally, the proton hopping may also be prevented by eliminating the proton, for example by substituting it with an alkyl moiety or by eliminating the 2-hydroxy group of the phenol altogether. In all these cases, the novel materials created are both photoluminescent and electroluminescent.

This is to say that small molecule benzotriazoles are either emissive or non-emissive depending on the choice of the group directly attached to the benzotriazole unit. For example, when two unsubstituted or alkyl substituted phenyl groups are attached at positions 4 and 7 of a benzotriazole unit (e.g., as in 2,4-di-tert-butyl-6-(4,7-diphenyl-2H-benzo[d][1, 2,3]triazol-2-yl)phenol), no photo- or electroluminescence is observed. However, when groups such as aromatic amines or alkoxy substituted phenyls are attached (e.g., as in 2-(4,7-bis (4-(dimethylamino)phenyl)-2H-benzo[d][1,2,3]triazol-2-yl)-4,6-di-tert-butylphenol), strong green, yellow, or even red emission is observed, depending on the planarity and energy levels of the attached units.

Similarly, while polymers comprising a 2,4-di-tert-butyl-6-(2H-benzo[d][1,2,3]triazol-2-yl)phenol repeat unit wherein two unsubstituted or alkyl substituted phenyl groups are attached at positions 4 and 7 of the benzotriazole (e.g., as in 2,4-di-tert-butyl-6-(4,7-diphenyl-2H-benzo[d][1,2,3]triazol-2-yl)phenol) are non fluorescent

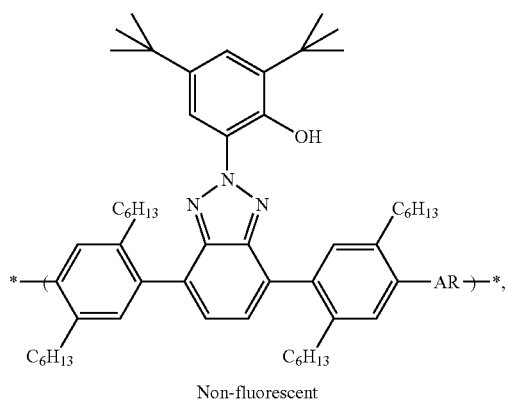

Non-fluorescent polymers comprising: (a) a 2,4-di-tert-butyl-6-(2H-benzo[d][1,2,3]triazol-2-yl)phenol repeat unit, wherein two alkoxy substituted phenyl groups are attached at positions 4 and 7 of the benzotriazole,

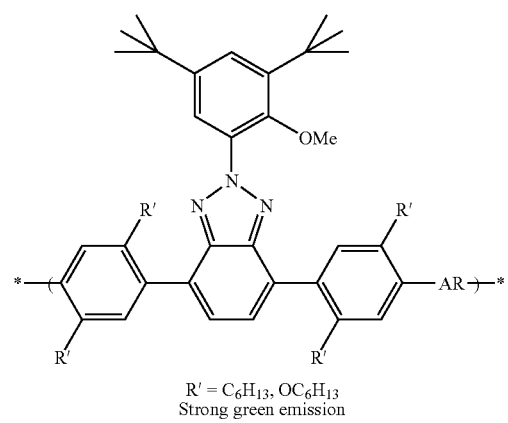

Strong green emission (b) a 2-(3,5-di-tert-butyl-2-methoxyphenyl)-2H-benzo[d][1,2,3]triazole repeat unit, R' = $C_6H_{13}$, $OC_6H_{13}$
Strong green emission and (c) a 2-(4,7-bis(9,9-dioctyl-9H-fluoren-2-yl)-2H-benzo[d][1,2,3]triazol-2-yl)-4,6-di-tert-butylphenol repeat unit (wherein a:b:c:d is about 25 mol %: 25 mol %: 25 mol %: 25 mol %),

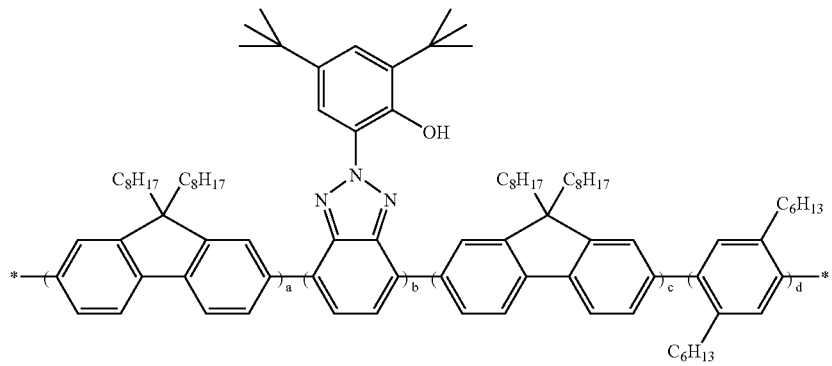

Strong green emission all exhibit strong green emission at about 500 nm. Thus, depending on what the adjacent group to the substituted phenol benzotriazole is, the polymer molecule is either optically active, i.e., bright, or inactive, i.e., dark.

This indicates that the excited state energy level for the chromophore as defined by the general formula:

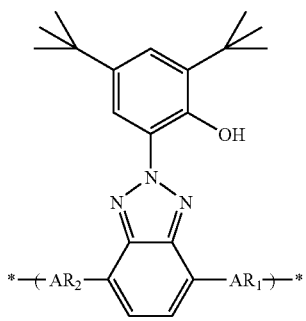

has a determining influence on whether the excited state decays radiatively or is quenched by isomerization of the phenol. Therefore, the identity of the groups $AR_1$ and $AR_2$ (which can be the same or different), can determine the ON or OFF state of the chromophore.

In certain embodiments of the present invention, it is desirable to electronically alter the energy level of the chromophore for it to be useful in optical switch, memory, or other application. This can be achieved by selection of the $AR_1$ and $AR_2$ groups that change their degree of conjugation when exposed to the appropriate photo, electrical, or thermal excitation.

This is to say that in certain embodiments this invention relates to molecules or polymers that contain the 2-(2H-benzo[d][1,2,3]triazol-2-yl)phenol subunit as part of their structure together with other groups attached to this subunit at the benzo moiety, the attached groups being capable of changing their interaction with the 2-(2H-benzo[d][1,2,3]triazol-2-yl) phenol either through changes of energy level or though changes of interaction between the attached groups and the hydroxyl group of 2-(2H-benzo[d][1,2,3]triazol-2-yl)phenol, such that the molecules change from an OFF state to an ON state upon exposure to a particular wavelength of light, the ON or OFF states being stable and reversible upon exposure to another wavelength of light. This feature of the novel materials of the present invention makes them extremely useful in read-write type of applications.

Because of the ability of the molecules to both electroluminesce and photoluminesce, the molecule or polymer can be switched optically between the ON-OFF states and electrically excited to emit (or not) depending on the state it is in. Therefore both an optical and an electrical read-write element or a switch is created. Applications for these type of materials include memory devices, sensors, tags, switches, etc.

DEFINITIONS

For convenience, certain terms employed in the specification, examples, and appended claims are collected here.

It is to be understood that this invention is not limited to the particular methodology, systems, protocols, constructs, and reagents described, as such may vary. It is also to be understood that the terminology used herein is for the purpose of describing particular embodiments only, and is not intended to limit the scope of the present invention which will be limited only by the appended claims.

Chemical Moieties

Herein, the term "aliphatic group" refers to a straight-chain, branched-chain, or cyclic aliphatic hydrocarbon group and includes saturated and unsaturated aliphatic groups, such as an alkyl group, an alkenyl group, and an alkynyl group.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In particular embodiments, a straight chain or branched chain alkyl has 30 or fewer carbon atoms in its backbone (e.g., $C_1$-$C_{30}$ for straight chain, $C_3$-$C_{30}$ for branched chain), and more preferably 20 or fewer carbon atoms. Likewise, particular cycloalkyls have from 3-10 carbon atoms in their ring structure, and more particularly have 5, 6 or 7 carbons in the ring structure.

Moreover, the term "alkyl" (or "lower alkyl") as used throughout the specification, examples, and claims is intended to include both "unsubstituted alkyls" and "substituted alkyls," the latter of which refers to alkyl moieties having substituents replacing a hydrogen on one or more carbons of the hydrocarbon backbone. Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkys, carbonyl-substituted alkyls, —$CF_3$, —CN, and the like.

The term "heteroalkyl" refers to an alkyl as described above in which one or more hydrogen atoms to any carbon of the alkyl or one or more carbon atoms are replaced by a heteroatom selected from the group consisting of N, O, P, B, S, Si, Sb, Al, Sn, As, Se and Ge. Non-limiting examples of heteroalkyl groups include methoxy, ethoxy propoxy, isopropoxy, methylthio, ethylthio, propylthio, isopropylthio, n-butylthio, methoxymethyl, and cyano group.

The terms "alkenyl" and "alkynyl" refer to unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more particularly from one to six carbon atoms in its backbone structure. Likewise, "lower alkenyl" and "lower alkynyl" have similar chain lengths. Throughout the application, particular alkyl groups are lower alkyls. In more particular embodiments, a substituent designated herein as alkyl is a lower alkyl.

The term "aryl" as used herein includes 5-, 6- and 7-membered single-ring aromatic groups that may include from zero to four heteroatoms, for example, benzene, pyrrole, furan, thiophene, imidazole, oxazole, thiazole, triazole, tetrazole, pyrazole, pyridine, pyrazine, pyridazine and pyrimidine, and the like. Those aryl groups having heteroatoms in the ring structure may also be referred to as "aryl heterocycles" or "heteroaromatics." The aromatic ring can be substituted at one or more ring positions with such substituents as described above, for example, halogen, azide, alkyl, aralkyl, alkenyl, alkynyl, cycloalkyl, hydroxyl, alkoxyl, amino, nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —CF$_3$, —CN, or the like. The term "aryl" also includes polycyclic ring systems having two or more cyclic rings in which two or more carbons are common to two adjoining rings (the rings are "fused rings") wherein at least one of the rings is aromatic, e.g., the other cyclic rings can be cycloalkyls, cycloalkenyls, cycloalkynyls, aryls and/or heterocyclyls.

The term "heteroaryl" refers to aromatic hydrocarbon rings which contain at least one heteroatom, such as O, S, or N, in the ring. Non-limiting examples of heteroaryl groups include quinolinyl, pyridyl, pyrazinyl, indolyl, carbazolyl, furyl, pyrrolyl, thienyl, thiazolyl, pyrazolyl, oxazolyl, imidazolyl, indolyl, benzofuranyl, benzothiazolyl, pyridonal, and the like. Heteroaryl moieties may additionally be substituted or unsubstituted.

The term "aralkyl", as used herein, refers to an alkyl or heteroalkyl group substituted with an aryl or heteroaryl group (e.g. an aromatic or heteroaromatic group). Non-limiting examples of aralkyl groups include benzyl, phenethyl, 2-phenylbutyl, 4-phenylhexan-3-yl, 4-(pyridin-3-yl)hexan-3-yl, and (benzyloxy)methyl.

The term "alkaryl", as used herein, refers to an aryl or heteroaryl group (e.g. an aromatic or heteroaromatic group) substituted with an alkyl or heteroalkyl group. Non-limiting examples of alkaryl groups include o-tolyl, m-tolyl, p-tolyl, 2,3-dimethylphenyl, 3-butylphenyl, 2-(hexan-3-yl)naphthalen-4-yl, and 2-(1-ethoxypropyl)naphthalen-4-yl.

As used herein, the term "aryl coupling" shall mean any appropriate method for coupling two aromatic or heteroaromatic aryls known to the artisan. Such methods may include, but are not limited to Stille, Suzuki, Colon, Yamamoto (stoichiometric and catalytic), Negishi and Heck coupling methods. The Suzuki coupling using Ar—B(OH)$_2$ and Pd catalyst is an especially useful coupling method. The artisan will appreciate that there are a variety of available Pd catalysts which are acceptable for the Suzuki coupling. One such Pd catalyst is Pd(PPh$_3$)$_4$.

The term "aromatic" refers to a cyclic or polycyclic (carbo- or heterocyclic) moiety having a conjugated unsaturated electron system, i.e. (4n+2) delocalized Π electrons per aromatic ring, including, but not limited to, phenyl, biphenyl, benzyl, xylyl, naphthyl, anthryl, phenanthryl, tetrahydronaphthyl, azulenyl, indanyl, indenyl, pyridinyl, pyrrolyl, furanyl, thiophenyl, fluorenyl, fluorenonyl, dibenzofuranyl, dibenzothienyl, furyl, thienyl, pyridyl, oxazolyl, thiazolyl, imidazolyl, pyrazolyl, 2-pyrazolinyl, pyrazolidinyl, isoxazolyl, isothiazolyl, oxadiazolyl, triazolyl, thiadiazolyl, pyridazinyl, pyrimidinyl, pyrazinyl, triazinyl, trithianyl, indolizinyl, indolyl, isoindolyl, 3H-indolyl, indolinyl, benzo[b]furanyl, 2,3-dihydrobenzofuranyl, benzo[b]thiophenyl, 1H-indazolyl, benzimidazolyl, benzthiazolyl, purinyl, 4H-quinolizinyl, isoquinolinyl, cinnolinyl, phthalazinyl, quinazolinyl, quinoxalinyl, 1,8-naphthridinyl, pteridinyl, acridinyl, phenazinyl, phenothiazinyl, phenoxyazinyl, pyrazolo[1,5-c]triazinyl, carbazolyl, benzo[c]cinnolinyl, 9,10-dihydrophenanthrenyl, and the like. Aromatic groups can be unsubstituted or substituted with one, two or three substituents independently selected from alkyl, halogen, haloalkyl, hydroxy, hydroxyalkyl, alkenyl, alkenyloxy, alkoxy, alkoxyalkoxy, alkoxycarbonyl, amino, alkylamino, alkylsulfonyl, dialkylamino, aminocarbonyl, aminocarbonylalkoxy, aryl, arylalkyl, arylalkoxy, aryloxy, cyano, nitro, carboxy, cycloalkyl, cycloalkylalkyl, carboxyalkoxy and phenyl. As used herein the term "aromatic" includes heteroaromatic structures, single and multiple rings, and fused and non-fused rings. The substituents of aromatic groups taken together with the atoms they are connected to can form additional cyclic or polycyclic structures without affecting the aromaticity of the resulting molecule. For example, the two methyl substituents in 1,8-dimethylnaphthalene, an aromatic structure, taken together with the two carbon atoms to which they are connected can form a five-membered ring of 1,2-dihydroacenaphthylene, which is also an aromatic structure. Similarly, the two methyl substituents in o-xylene, an aromatic structure, taken together with the two carbon atoms to which they are connected can form a five-membered ring of 2,3-dihydro-1H-indene, which is also an aromatic structure.

The terms "benzotriazole" and "benzotriazoles" include substituted and unsubstituted benzotriazoles and benzotriazole derivatives. The term "unsubstituted benzotriazole" can be represented by the general formula:

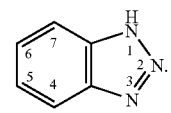

The term "substituted benzotriazoles," as used herein, refers to compounds of the general formula represented above which have been substituted at one or more positions by various substituents independently selected from alkyl, halogen, haloalkyl, hydroxy, hydroxyalkyl, alkenyl, alkenyloxy, alkoxy, alkoxyalkoxy, alkoxycarbonyl, amino, alkylamino, alkylsulfonyl, dialkylamino, aminocarbonyl, aminocarbonylalkoxy, aryl, arylalkyl, arylalkoxy, aryloxy, cyano, nitro, carboxy, cycloalkyl, cycloalkylalkyl, carboxyalkoxy, phenyl, etc. For example, a 4,7-dibromo-2-hexyl-benzotriazole (4,7-dibromo-2-hexyl-2H-benzo[d][1,2,3]triazole) would be represented by the following formula:

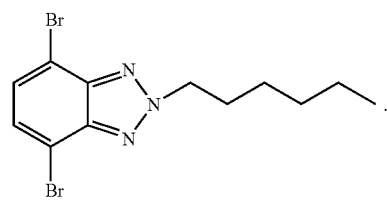

Specifically, a skilled artisan will recognize that the novel monomers, oligomers, and polymers described herein are optionally substituted as desired, either on the phenol or the benzo moieties, to impart solubility or enhance other desired properties.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

The term "heteroatom" as used herein means an atom of any element other than carbon or hydrogen. Particular heteroatoms are boron, nitrogen, oxygen, phosphorus, sulfur and selenium.

The terms "heterocyclyl" or "heterocyclic group" refer to 3- to 10-membered ring structures, more particularly 3- to 7-membered rings, whose ring structures include one to four heteroatoms. Heterocycles can also be polycycles. Heterocyclyl groups include, for example, thiophene, thianthrene, furan, pyran, isobenzofuran, chromene, xanthene, phenoxathiin, pyrrole, imidazole, pyrazole, isothiazole, isoxazole, pyridine, pyrazine, pyrimidine, pyridazine, indolizine, isoindole, indole, indazole, purine, quinolizine, isoquinoline, quinoline, phthalazine, naphthyridine, quinoxaline, quinazoline, cinnoline, pteridine, carbazole, carboline, phenanthridine, acridine, pyrimidine, phenanthroline, phenazine, phenarsazine, phenothiazine, furazan, phenoxazine, pyrrolidine, oxolane, thiolane, oxazole, piperidine, piperazine, morpholine, lactones, lactams such as azetidinones and pyrrolidinones, sultams, sultones, and the like. The heterocyclic ring can be substituted at one or more positions with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety, —$CF_3$, —CN, or the like.

The terms "polycyclyl" or "polycyclic group" refer to two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, ketone, aldehyde, ester, a heterocyclyl, an aromatic or heteroaromatic moiety —$CF_3$, —CN, or the like.

The term "carbocycle", as used herein, refers to an aromatic or non-aromatic ring in which each atom of the ring is carbon.

As used herein, the term "nitro" means —$NO_2$; the term "halogen" designates —F, —Cl, —Br or —I; the term "sulfhydryl" means —SH; the term "hydroxyl" means —OH; and the term "sulfonyl" means —$SO_2$—.

The terms "amine" and "amino" are art-recognized and refer to both unsubstituted and substituted amines, e.g., a moiety that can be represented by the general formula:

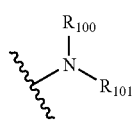 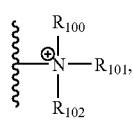

wherein $R_{100}$, $R_{101}$ and $R_{102}$ each independently represent a hydrogen, an alkyl, an alkenyl, —$(CH_2)_m$—$R_{110}$, or $R_{100}$ and $R_{101}$ taken together with the N atom to which they are attached complete a heterocycle having from 4 to 8 atoms in the ring structure; $R_{110}$ represents an aryl, a cycloalkyl, a cycloalkenyl, a heterocycle or a polycycle; and m is zero or an integer in the range of 1 to 8. In preferred embodiments, only one of $R_{100}$ or $R_{101}$, can be a carbonyl, e.g., $R_{100}$, $R_{101}$, and the nitrogen together do not form an imide. In even more preferred embodiments, $R_{100}$ and $R_{101}$ (and optionally $R_{102}$) each independently represent a hydrogen, an alkyl, an alkenyl, or —$(CH_2)_m$—$R_{110}$. Thus, the term "alkylamine" as used herein means an amine group, as defined above, having a substituted or unsubstituted alkyl attached thereto, i.e., at least one of $R_{100}$ and $R_{101}$ is an alkyl group.

The term "acylamino" is art-recognized and refers to a moiety that can be represented by the general formula:

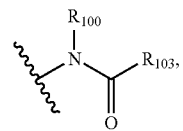

wherein $R_{100}$ as defined above, and $R_{103}$ represents a hydrogen, an alkyl, an alkenyl or $(CH_2)_m R_{110}$, wherein m and $R_{110}$ are as defined above.

The term "amido" is art recognized as an amino-substituted carbonyl and includes a moiety that can be represented by the general formula:

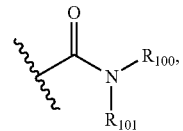

wherein $R_{100}$, $R_{101}$ are as defined above. Preferred embodiments of the amide will not include imides which are optionally unstable.

The term "alkylthio" refers to an alkyl group, as defined above, having a sulfur radical attached thereto. In preferred embodiments, the "alkylthio" moiety is represented by one of Salkyl, Salkenyl, Salkynyl, and —$S(CH_2)_m R_{110}$, wherein m and $R_{110}$ are defined above. Representative alkylthio groups include methylthio, ethyl thio, and the like.

The term "carbonyl" is art recognized and includes such moieties as can be represented by the general formula:

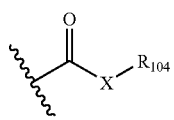 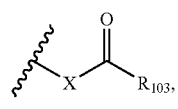

wherein X is a bond or represents an oxygen or a sulfur, and $R_{104}$ represents a hydrogen, an alkyl, an alkenyl, $(CH_2)_m R_{110}$ or a pharmaceutically acceptable salt, $R_{103}$ represents a hydrogen, an alkyl, an alkenyl or $(CH_2)_m R_{110}$, where m and $R_{110}$ are as defined above. Where X is an oxygen and $R_{104}$ or $R_{103}$ is not hydrogen, the formula represents an "ester". Where X is an oxygen, and $R_{104}$ is as defined above, the moiety is referred to herein as a carboxyl group, and particularly when $R_{104}$ is a hydrogen, the formula represents a "carboxylic acid". Where X is an oxygen, and $R_{103}$ is a hydrogen, the formula represents a "formate". In general, where the oxygen atom of the above formula is replaced by sulfur, the formula represents a "thiolcarbonyl" group. Where X is a sulfur and $R_{104}$ or $R_{103}$ is not hydrogen, the formula represents a "thiolester." Where X is a sulfur and $R_{104}$ is hydrogen, the formula represents a "thiolcarboxylic acid." Where X is a sulfur and $R_{103}$ is hydrogen, the formula represents a "thiolformate." On the other hand, where X is a bond, and $R_{104}$ is not hydrogen, the above formula represents a "ketone" group. Where X is a bond, and $R_{104}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —Oalkyl, Oalkenyl, Oalkynyl, $O(CH_2)_m R_{110}$, where m and $R_{110}$ are described above.

The term "sulfonate" is art recognized and includes a moiety that can be represented by the general formula:

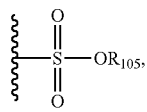

in which $R_{105}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The term "sulfate" is art recognized and includes a moiety that can be represented by the general formula:

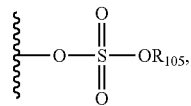

in which $R_{105}$ is as defined above.

The term "sulfonamido" is art recognized and includes a moiety that can be represented by the general formula:

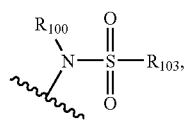

in which $R_{100}$ and $R_{103}$ are as defined above.

The term "sulfamoyl" is art-recognized and includes a moiety that can be represented by the general formula:

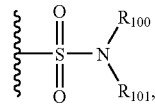

in which $R_{100}$ and $R_{101}$ are as defined above.

The terms "sulfoxido" or "sulfinyl", as used herein, refers to a moiety that can be represented by the general formula:

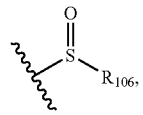

in which $R_{106}$ is selected from the group consisting of hydrogen, alkyl, alkenyl, alkynyl, cycloalkyl, heterocyclyl, aralkyl, or aryl.

A "phosphoryl" can in general be represented by the formula:

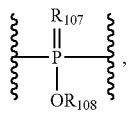

wherein $R_{107}$ represented S or O, and $R_{108}$ represents hydrogen, a lower alkyl or an aryl. When used to substitute, e.g. an alkyl, the phosphoryl group of the phosphorylalkyl can be represented by the general formula:

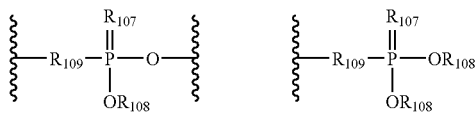

wherein $R_{107}$ represented S or O, and each $R_{108}$ independently represents hydrogen, a lower alkyl or an aryl, $R_{109}$ represents O, S or N. When $R_{107}$ is an S, the phosphoryl moiety is a "phosphorothioate".

A "selenoalkyl" refers to an alkyl group having a substituted seleno group attached thereto. Exemplary "selenoethers" which may be substituted on the alkyl are selected from one of —Se-alkyl, —Se-alkenyl, —Se-alkynyl, and —Se$(CH_2)_m R_{110}$, m and $R_{110}$ being defined above.

Analogous substitutions can be made to alkenyl and alkynyl groups to produce, for example, aminoalkenyls, aminoalkynyls, amidoalkenyls, amidoalkynyls, iminoalkenyls, iminoalkynyls, thioalkenyls, thioalkynyls, carbonyl-substituted alkenyls or alkynyls.

As used herein, the definition of each expression, e.g. alkyl, m, n, etc., when it occurs more than once in any structure, is intended to be independent of its definition elsewhere in the same structure.

Certain compounds of the present invention may exist in particular geometric or stereoisomeric forms. "Stereoisomers" are compounds that have the same sequence of covalent bonds and differ in the relative disposition of their atoms in space. Stereoisomers fall within two broad classes: optical isomers and geometric isomers. The present invention contemplates all such compounds, including cis- and trans-isomers, R- and and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

If, for instance, a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Contemplated equivalents of the compounds described above include compounds which otherwise correspond thereto, and which have the same general properties thereof (e.g. the ability to function as luminescent devices), wherein one or more simple variations of substituents are made which do not adversely affect the properties of the compound. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants which are in themselves known, but are not mentioned here.

It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

Substitution in general chemical formulas is illustrated, for example, as follows:

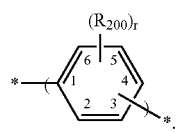

Referring to the structure above, the depicted arylene repeat unit is a bivalent radical, i.e., derived from aryls by removal of hydrogen atoms from each of the two terminal carbon atoms of the chain, e.g., phenylene. The arylene is attached to other repeat units at positions 1 and at one other position (2, 3, 4, 5, or 6). In addition, depending on the definition of r, the arylene repeat unit may be unsubstituted or substituted by one to four substituents $R_{200}$, wherein $R_{200}$ is contemplated to include all permissible substituents of organic compounds. For example, if r is 0, the arylene repeat unit is unsubstituted; if r is 1, the arylene unit is substituted by one substituent $R_{200}$, and that substituent is attached at any position 2, 3, 4, 5, or 6, except that it is not attached at the point of attachment of the arylene repeat unit to other repeat units; if r is 2, the arylene unit is substituted by two substituents $R_{200}$, and these substituent are attached at any position 2, 3, 4, 5, or 6, except that they are not attached at the point of attachment of the arylene repeat unit to other repeat units and that they are not both attached to the same position; if r is 0-1, the arylene repeat unit is either unsubstituted or is substituted by one substituent $R_{200}$, and that substituent is attached at any position 2, 3, 4, 5, or 6, except that it is not attached at the point of attachment of the arylene repeat unit to other repeat units, and so on.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described herein above. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. This invention is not intended to be limited in any manner by the permissible substituents of organic compounds.

For purposes of this invention, the chemical elements are identified in accordance with the Periodic Table of the Elements, CAS version, Handbook of Chemistry and Physics, 67th Ed., 1986-87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. Protective Groups in Organic Synthesis, 2.sup.nd ed.; Wiley: New York, 1991).

A list of many of the abbreviations utilized by organic chemists of ordinary skill in the art appears in the first issue of each volume of the Journal of Organic Chemistry; this list is typically presented in a table entitled Standard List of Abbreviations. The abbreviations contained in said list, and all abbreviations utilized by organic chemists of ordinary skill in the art are hereby incorporated by reference.

Polymers

"Polymer" means a substance composed of macromolecules generally prepared by polymerizing monomers of the same or different type. "Macromolecule" means a molecule of high relative molecular mass, the structure of which essentially comprises the multiple repetition of a number of constitutional units. "Constitutional unit" means an atom or group of atoms in a macromolecule or oligomer molecule, comprising a part of the chain together with its pendant atoms or groups of atoms, if any. "Constitutional repeating unit" means the smallest constitutional unit, the repetition of which constitutes a regular macromolecule (or oligomer molecule or block).

"Polymer" includes homopolymers, copolymers, terpolymers, interpolymers, and so on. As used herein, the term "homopolymer" is used with reference to a polymer derived from one species of (real, implicit, or hypothetical) monomer, i.e., a polymer consisting essentially of a single type of repeating unit. (Many polymers are made by mutual reaction of complementary monomers. These monomers can readily be visualized as reacting to give an "implicit monomer", the homopolymerization of which would give the actual product, which can then be regarded as a homopolymer. Example: poly(ethylene terephthalate). Some polymers are obtained by modification of other polymers such that the structure of the macromolecules that constitute the resulting polymer can be thought of as having been formed by homopolymerization of a "hypothetical monomer". These polymers can be regarded as homopolymers. Example: poly(vinyl alcohol).) The term "interpolymer" means a polymer prepared by the polymerization of at least two types of monomers or comonomers. It includes, but is not limited to, copolymers (which usually refers to polymers prepared from two different types of monomers or comonomers, although it is often used interchangeably with "interpolymer" to refer to polymers made from three or more different types of monomers or comonomers), terpolymers (which usually refers to polymers prepared from three different types of monomers or comonomers), tetrapolymers (which usually refers to polymers prepared from four different types of monomers or comonomers), and the like.

As used throughout this disclosure, the term "linear polymer" refers to a polymer in which the monomer molecules have been linked together in one continuous length to form the polymer molecule, i.e., polymer with no branch points intermediate between the boundary units (i.e. the end-groups or other branch points). The term "chain" refers to the whole part of part of a macromolecule (or oligomer molecule or block) comprising a sequence of constitutional units between two boundary constitutional units, each of which may be either an end-group or a branch point. (Except in linear single-strand macromolecules, the definition of the chain may be somewhat arbitrary. A cyclic macromolecule has no end groups but may nevertheless be regarded as chain. Where appropriate, definitions relating to "macromolecule" may also be applied to "chain".)

The term "branch" refers to an oligomeric or polymeric offshoot from a branched chain. The term "branched chain" refers to a chain with at least one branch point intermediate between the boundary units (i.e. the end-groups or other branch points). The term "branch point" refers to a point on a chain at which a branch is attached. The term "branched polymer" refers to a polymer, the molecules of which are branched chains. "Branched polymer" does not refer to linear polymers containing side groups that are part of the monomer structure. Only those polymers that contain side branches composed of complete monomer units are termed "branched polymers."

The term "substantially linear" refers to a preference for no more than three or four branches on average per polymer chain, particularly one or two, and most particularly zero. The terms "dendritic," "dendrimeric," and "dendrimer" refer to a polymer having branches protruding from other branches, as opposed to protruding from the polymer backbone, that is, when there are branched branches. The term "hyperbranched," as used herein, with respect to branched polymers are intended to designate polymers having a relatively high percentage of branches per number of polymerized monomer units, e.g., at least one branch per every ten monomer units, and more particularly at least one branch per every five monomer units. The term "crosslinked" refers to a polymer network in which polymer molecules that were earlier separate molecules are linked to each other at points other than their ends. In the vast majority of cases, the crosslink is a covalent bond but the term is also used to describe sites of weaker chemical interactions, portions of crystallites, and even physical entanglements.

The term "block" refers to a portion of a macromolecule, comprising many constitutional units, that has at least one feature which is not present in the adjacent portions. The term "block macromolecule" refers to a macromolecule which is composed of blocks in linear sequence. The term "block polymer" refers to a substance composed of block macromolecules. For example, a diblock polymer is composed of two blocks, a triblock polymer is composed of three blocks, etc. The term "block copolymer" refers to a copolymer that is a block polymer. In a block copolymer, adjacent blocks are constitutionally different, i.e., each of these blocks comprises constitutional units derived from different characteristic species of monomer or with different composition or sequence distribution of constitutional units.

As used herein with respect to polymers, the term "random" refers to copolymers, terpolymers, interpolymers, and so on, consisting of macromolecules in which the probability of finding a given monomeric unit at any given site in the chain is independent of the nature of the adjacent units. In a random copolymer, the sequence distribution of monomeric units follows Bernoullian statistics.

The terms "monomer" or "comonomer" are used interchangeably, and they refer to a substance, each of the molecules of which can, on polymerization, contribute one or more constitutional units in the structure of the macromolecule. In those instances in which a polymer is described as comprising one or more monomers, e.g., a polymer comprising propylene and ethylene, the polymer, of course, comprises units derived from the monomers, e.g., $—CH_2—CH_2—$, and not the monomer itself, e.g., $CH_2=CH_2$. The term "oligomer" as used herein refers to a substance composed of oligomer molecules. The term "oligomer molecule" refers a molecule of intermediate relative molecular mass (as compared to a polymer), the structure of which essentially comprises a small plurality of constitutional units, such as a dimer, trimer, tetramer, etc., or their mixtures. The term "constitutional repeating unit" refers to the smallest constitutional unit, the repetition of which constitutes a regular macromolecule (or oligomer molecule or block). The term "constitutional unit" refers to an atom or group of atoms in a macromolecule or oligomer molecule, comprising a part of the chain together with its pendant atoms or groups of atoms, if any.

A skilled artisan will recognize that novel polymers described herein can be in whole or a part of a conjugated or non-conjugated polymer, linear, branched, hyperbranched or dendritic polymer; they can be crosslinkable or crosslinked, and can contain any desired additive, can be homopolymers or copolymers, and can be prepared via any synthetic method.

Chemical Phenomena and Display Technologies

The term "luminescence," as used herein, refers to the detectable electromagnetic radiation, generally, UV, IR or visible electromagnetic radiation from a substance for any reason other than a rise in its temperature. In general, radiation at specific frequencies excites the natural resonant energy levels of the substance involved. When such resonance occurs, energy is absorbed from the incident radiation elevating free electrons into a higher energy state. This energy can then be re-emitted by spontaneous decay of the electrons into their lower energy state ("radiative decay"). The emission of photons of electromagnetic energy (e.g., visible light) by atoms or molecules as then move from an "excited state" to a lower energy state (usually the ground state) is termed "luminescence".

The different forms of luminescence are distinguished by the mechanism that causes the excitation. For example, if the exciting cause is a photon, the luminescence process is referred to as "photoluminescence." If the exciting cause is an electron, the luminescence process is referred to as "electroluminescence." More specifically, electroluminescence results from the direct injection and removal of electrons to form an electron-hole pair, and subsequent recombination of the electron-hole pair to emit a photon. Luminescence which results from a chemical reaction is usually referred to as "chemiluminescence." Luminescence produced by a living organism is usually referred to as "bioluminescence." If photoluminescence is the result of a spin-allowed transition (e.g., a single-singlet transition, triplet-triplet transition), the photoluminescence process is usually referred to as "fluorescence." Fluorescence is luminescence that is maintained only by continuous excitation; that is, emission occurs immediately after excitation and stops when excitation stops. Fluorescence does not have an afterglow. This is to say that fluorescence emissions do not persist after the exciting cause is removed as a result of short-lived excited states which may rapidly relax through such spin-allowed transitions. If photoluminescence is the result of a spin-forbidden transition (e.g., a triplet-singlet transition), the photoluminescence process is usually referred to as "phosphorescence." Phosphorescence is luminescence that persists (afterglow) for some time after the excitation is removed.

This is to say that phosphorescence emissions persist for some time after the exciting cause is removed as a result of long-lived excited states which may relax only through such spin-forbidden transitions.

The term "luminescence" thus refers to, without limitation, electrical (electro) luminescence, chemical luminescence, fluorescence, phosphorescence, bioluminescence, and the like.

The term "phosphor" refers to any material capable of exhibiting luminescence under external energy excitation.

The term "quantum efficiency" is used herein to refer to the efficiency which a device is capable of converting the incoming energy into the outgoing energy. For example, quantum efficiency of a photosensitive device is the efficiency with which a photosensitive optoelectronic device is capable of converting the total incident radiation into electrical energy, i.e., it is the quotient of the electrical energy produced by the device to the electromagnetic energy (light) received by the device. For an electroluminescent device, the term "quantum efficiency" refers to the ratio of the number of photons emitted by a substance to the number of photons absorbed by the substance.

Novel materials and processes described herein may be used as UV stabilizers or in the production of UV stabilizers. The terms "UV stabilizer" and "ultraviolet stabilizer" as used herein refer to a substance capable of absorbing radiant energy in the ultraviolet wavelength range and dissipating the absorbed energy without being deteriorated as a result of absorbing UV radiation. UV stabilizers may be added to, mixed with, or incorporated, by covalent or non-covalent interactions, into other materials (e.g., plastics) for the purpose of UV protection, i.e., to prevent the degradation of the materials to be protected by UV radiation. 2-hydroxyphenyl-benzotriazoles and derivatives thereof are commonly used as UV stabilizers, primarily for incorporation into commercial plastics. See, e.g., U.S. Pat. Nos. 6,774,238 and 6,756,499. 2-hydroxyphenylbenzotriazoles can absorb UV light resulting in an excited energy state. The excited energy state is "degraded" (i.e., reverts to a ground energy state) by driving an internal proton transfer back and forth from the hydroxyl group of the phenol to the nitrogen atoms in the 1 and 3 position. The key to the usefulness of the 2-hydroxyphenyl-benzotriazoles as UV stabilizers is that during the return from excited energy state to the ground energy state via proton hopping, energy is lost as heat and is not available to do damage to the material that the benzotriazole is protecting.

A "light-emitting diode" (LED) is a semiconductor device that emits incoherent monochromatic light when electrically biased in the forward direction. This effect is a form of electroluminescence. (As explained above "electroluminescence" is an optical and electrical phenomenon where a material emits electromagnetic radiation when an electric current is passed through it.) The color of emitted light depends on the semiconducting material used in the LED, and can be near-ultraviolet, visible or infrared. A LED is a special type of semiconductor diode. Like a normal diode, it consists of a chip of semiconducting material impregnated, or doped, with impurities to create a structure called a pn junction. Charge-carriers (electrons and holes) are created by an electric current passing through the junction. When an electron meets a hole, it falls into a lower energy state, and releases energy in the form of a photon as it does so.

The wavelength of the light emitted by a LED, and therefore its color, depends on the bandgap energy of the materials forming the pn junction. A normal diode, typically made of silicon or germanium, emits invisible far-infrared light, but the materials used for a LED have bandgap energies corresponding to near-infrared, visible or near-ultraviolet light.

Unlike incandescent bulbs, which can operate with either AC or DC, LEDs require a DC supply of the correct polarity. When the voltage across the pn junction is in the correct direction, a significant current flows and the device is said to be forward biased. The voltage across the LED in this case is fixed for a given LED and is proportional to the energy of the emitted photons. If the voltage is of the wrong polarity, the device is said to be reverse biased, very little current flows, and no light is emitted.

Because the voltage versus current characteristics of an LED are much like any diode, they can be destroyed by connecting them to a voltage source much higher than their turn on voltage. A good LED driver circuit is either a constant current source or an approximation to a current source made by connecting the LED in series with a current limiting resistor to a voltage source. The voltage drop across a forward biased LED increases as the amount of light emitted increases because of the optical power being radiated. One consequence is that LED's of the same type can be readily operated in parallel. The turn-on voltage of an LED is a function of the color, a higher forward drop is associated with emitting higher energy (bluer) photons. The reverse voltage that most LEDs can sustain without damage is usually only a few volts. Some LEDs packages contain two diodes, one in each direction, and each a different color, typically red and green, which allows two color operation or a range of colors to be created by altering the percentage of time the voltage is in each polarity.

Conventional LEDs are made of inorganic minerals such as: aluminium gallium arsenide (AlGaAs)—red and infrared; gallium arsenide/phosphide (GaAsP)—red, orange and yellow; gallium nitride (GaN)—green; gallium phosphide (GaP)—green; zinc selenide (ZnSe)—blue; indium gallium nitride (InGaN)—blue; silicon carbide (SiC)—blue; and diamond (C)—ultraviolet.

If the emissive layer material of an LED is an organic compound, the LED is known as an Organic Light Emitting Diode (OLED). To function as a semiconductor, the organic emissive material must generally have conjugated pi bonds. The emissive material can be a small organic molecule in a crystalline phase, or a polymer. Polymer materials can be flexible. LEDs containing polymer semiconductor materials are known as Polymer LEDs (PLEDs) or Flexible LEDs (FLEDs). The novel monomers, oligomers, and polymers described herein are particularly useful as emissive layer material for use in OLEDs and OLED displays.

Organic light emitting diodes (OLEDS) are optoelectronic devices based on small molecules or polymers that emit light when an electrical current flows through them. A simple OLED consists of an organic layer sandwiched between two metal electrodes Under application of an electric field, electrons and holes are injected from the two electrodes respectively into the organic layer, where they meet and recombine to produce light. The output efficiency of this process is within the spectrum from blue to infrared. Also, by blending polymers with different emission and charge-transport characteristics, OLEDs can be fabricated in which the emission color varies as a function of the operating voltage.

Compared with regular LEDs, OLEDs are lighter and polymer LEDs can have the added benefit of being flexible. Currently, much research and development focuses on employing OLEDs as graphic displays in consumer products, such as monitors, laptops, cell phones, music players, shavers, and others, and many such devices are either in their prototype stages or have already been brought to market. Some possible future consumer applications of OLEDs include their utility as light sources, wall decorations, luminous cloth, product packaging, etc.

The organic layers of luminescent devices comprising novel compounds disclosed herein have no particular restrictions as to the fabrication method. Various methods, such as a resistance heating-utilized vapor deposition method, an electron-beam heating method, a sputtering method, a molecular lamination method, a coating method and an ink jet method can be adopted. In particular, the resistance heating-utilized vapor deposition method and the coating method are favorable methods from the viewpoints of the characteristics imparted to the device and the efficiency in producing the device.

The present luminescent device is a device having a luminescent layer or two or more thin layers of organic compounds, including a luminescent layer, between a pair of electrodes, an anode and a cathode. The thin layers the device may have in addition to the luminescent layer are, e.g., a hole injection layer, a hole transfer layer, an electron injection layer, an electron transfer layer and a protective layer. The aforementioned layers each may have another function also. For forming each layer, various materials can be employed.

The anode supplies holes to a hole injection layer, a hole transfer layer and a luminescent layer. As a material for the anode, metals, alloys, metal oxides, electrically conductive materials and mixtures thereof, preferably materials having a work function of at least 4 eV, can be used. Examples of such materials include conductive metal oxides, such as tin oxide, zinc oxide, indium oxide and indium tin oxide (ITO), metals such as gold, silver, chromium and nickel, mixtures or laminates of those metals and conductive metal oxides, inorganic conductive materials such as copper iodide and copper sulfide, organic conductive materials such as polyaniline, polythiophene and polypyrrole, and laminates of those materials and ITO. Of the materials recited above, the conductive metal oxides are favored over the others. In particular, ITO is used to advantage from the viewpoint of productivity, conductivity and transparency. The suitable thickness of the anode, though can be selected depending on the anode material, is generally from 5 μm to 10 nm, particularly 1 μm to 50 nm, more particularly 100 nm to 500 nm.

The anode has on a soda lime glass, alkali-free glass or transparent resin substrate an anode material formed into a layer. In a case of using a glass substrate, alkali-free glass is preferred from the viewpoint of reduction in ions eluted from the glass. When soda glass is used as the substrate, it is desirable that the barrier coat, such as silica, be provided on the glass. The thickness of the substrate has no particular limitation as long as the substrate can ensure mechanical strength for the anode. For instance, the suitable thickness of a glass substrate is generally at least 0.2 mm, preferably at least 0.7 mm. The methods suitable for making the anode vary with the material used. In the case of ITO, for example, the film formation can be carried out using an electron-beam heating method, a sputtering method, a resistance heating-utilized vapor deposition method, a chemical reaction method (e.g., sol-gel method) or the method of coating a dispersion of indium tin oxide. Washing and other treatments for the anode enable the device to get a reduction in operating potential and improve in light-emitting efficiency. In the case of an anode using ITO, it is effective for the anode to receive UV-ozone treatment or plasma treatment.

The cathode supplies electrons to an electron injection layer, an electron transfer layer and a luminescent layer. In selecting the cathode, the adhesiveness to the electron injection, electron transfer or luminescent layer adjacent to the cathode, ionization potential and the stability are taken into consideration. As a material for the cathode, metals, alloys, metal halides, metal oxides, electrically conductive materials and mixtures thereof can be employed. Examples of such materials include alkali metals (e.g., Li, Na, K), alkaline earth metals (e.g., Mg, Ca), gold, silver, lead, aluminum, Na—K alloy or the mixture thereof, Li—Al alloy or mixture, Mg—Ag alloy or mixture, and rare earth metals (e.g., In, Yb). Of these materials, the materials having a work function of at most 4 eV are favored over the others. In particular, aluminum, Li—Al alloy or mixture, and Mg—Ag alloy or mixture are used to advantage. The cathode structure may be a single-layer of the compound or mixture as recited above or a laminate of the compounds and/or mixtures as recited above. The suitable thickness of the cathode, though can be selected depending on the cathode material, is generally from 5 μm to 10 nm, particularly 1 μm to 50 nm, and more particularly 1 μm to 100 nm. In forming the cathode, various known methods, such as an electron-beam heating method, a sputtering method, a resistance heating-utilized vapor deposition method and a coating method, can be adopted. The metals as recited above may be evaporated independently, or two or more thereof may be evaporated simultaneously. Further, it is possible to evaporate a plurality of metals at the same time to form an alloy electrode, or to evaporate the previously prepared alloy. It is advantageous to the luminescent device that both anode and cathode have low sheet resistance, specifically several hundreds Ω/sq at the highest.

The present luminescent device may further comprise a metal fluoride layer. Without wishing to be bound by theory, it is believed that the energy barrier for electron transport at the interface between the luminescent layer and the cathode may be lowered by providing a metal fluoride layer between the luminescent layer and the cathode. This improves the electron injection efficiency, thereby also improving the lifetime of the element. The metal fluoride layer can be selected from an alkali fluoride or an alkaline earth fluoride, which include lithium fluoride, sodium fluoride, potassium fluoride, rubidium fluoride, cesium fluoride, magnesium fluoride, calcium fluoride, strontium fluoride, or barium fluoride. The suitable thickness of the metal fluoride layer is generally from about 100 nm to about 0.5 nm, particularly about 50 nm to about 2 nm, more particularly about 10 nm to about 5 nm. It should be noted here that a similar energy barrier lowering effect can be produced by substituting the above-mentioned metal fluoride layer by a layer made of a metal oxide such as $Li_2O$, $MgO$, or $Al_2O_3$.

The material usable for a luminescent layer is a material capable of forming a layer which can function so as to receive both hole injection from the anode, the hole injection layer or the hole transfer layer and electron injection from the cathode, the electron injection layer or the electron transfer layer when the electric field is applied thereto, permit the charges injected therein to move and enable the emission of light by providing a place for recombining the holes and the electrons. As the material as defined above, the present polymer, oligomer, and monomer compounds can be contained in the luminescent layer. In addition, other materials hitherto known to be luminescent, such as benzoxazole derivatives, benzimidazole derivatives, benzothiazole derivatives, benzothiadiazole derivatives, styrylbenzene derivatives, polyphenyl derivatives, diphenylbutadiene derivatives, tetraphenylbutadiene derivatives, naphthalimide derivatives, coumarin derivatives, perylene derivatives, perinone derivatives, oxadiazole derivatives, aldazine derivatives, pyridine derivatives, cyclopentadiene derivatives, bisstyrylanthracene derivatives, quinacridone derivatives, pyrrolopyridine derivatives, thiadiazolopyridine derivatives, styrylamine derivatives, aromatic dimethylidyne derivatives, various metal complexes represented by metal or rare earth complexes of 8-quinolinol derivatives, and polymeric compounds such as polythiophene, polyphenylene and polyphenylene-vinylene, may also be used in the luminescent layer. Although the luminescent layer has no particular restrictions as to the thickness, the suitable thickness thereof is generally from 1 nm to 5 µm, particularly 5 nm to 1 µm, more particularly 10 nm to 500 nm.

As to the method of forming the luminescent layer, there are no particular restrictions, but various methods including resistance heating-utilized vapor deposition methods, electron-beam heating methods, sputtering methods, spraying methods, molecular lamination methods, coating methods (e.g., a spin coating, cast coating or dip coating method), ink jet methods, printing methods (e.g. offset printing, screen printing, flexographic printing), lithography methods and LB methods can be adopted. Of these methods, spin-coating and printing are particularly useful.

The materials for the hole injection layer and the hole transfer layer may be any materials so long as they have any one of the functions as an injector of the holes from the anode, a transfer of holes and a barrier against electrons injected from the cathode. Examples of materials hitherto known to have one of such functions include carbazole derivatives, phenylenediamine derivatives, arylamine derivatives, aromatic tertiary amine compounds, styrylamine compounds, porphyrin compounds, polysilane compounds, and conductive polymers or oligomers, such as poly(N-vinylcarbazole) (PVK) and PVK derivatives, aniline copolymers and thiophene oligomers or polythiophene derivatives. The thickness of the hole injection layer and the hole transfer layer each, though it has no particular limitation, is generally from 1 nm to 5 µm, preferably 5 nm to 1 µm, particularly preferably 10 nm to 500 nm. Each of the hole injection layer and the hole transfer layer may have a single-layer structure constituted of one or more of the materials recited above or a multiple-layer structure made up of at least two layers having the same composition or different compositions.

As a method of forming a hole injection layer and a hole transfer layer, a vacuum evaporation method, an LB method, an ink jet method, a printing method, and a method of coating a compound capable of injecting or transferring holes in the form of a solution or dispersion in an appropriate solvent (using, e.g., a spin coating, cast coating or dip coating method) can be adopted. In the case of a coating method, the compound can be dissolved or dispersed in the presence of a resin component (binder polymer). Examples of such a resin component include polyvinyl chloride, polycarbonate, polystyrene, polymethyl methacrylate, polybutyl methacrylate, polyester, polysulfone, polyphenylene oxide, polybutadiene, poly(N-vinylcarbazole), hydrocarbon resin, ketone resin, phenoxy resin, polyamide, ethyl cellulose, polyvinyl acetate, ABS resin, polyurethane, melamine resin, unsaturated polyester resin, alkyd resin, epoxy resin and silicone resin.

The materials for the electron injection layer and the electron transfer layer may be any materials so long as they have any one of the functions as an injector of the electrons from the cathode, a transfer of electrons and a barrier against holes injected from the anode. Examples of compounds known to have such a function include triazole derivatives, oxazole derivatives, oxadiazole derivatives, fluorenone derivatives, anthraquinodimethane derivatives, anthrone derivatives, diphenylquinone derivatives, thiopyran dioxide derivatives, carbodimide derivatives, fluorenylidenemethane derivatives, distyrylpyrazine derivatives, heterocyclic tetracarboxylic acid anhydrides such as naphthaleneperylene, phthalocyanine derivatives, and various metal complexes represented by metal complexes of 8-quinolinol derivatives, metallophthalocyanine and metal complexes containing benzoxazole or benzothiazole ligands. The thickness of the electron injection layer and the electron transfer layer each, though it has no particular limitation, is generally from 1 nm to 5 µm, preferably 5 nm to 1 µm, particularly preferably 10 nm to 500 µm. Each of the electron injection layer and the electron transfer layer may have a single-layer structure constituted of one or more the compounds as recited above, or a multiple-layer structure made up of at least two layers having the same composition or different compositions.

As a method of forming the electron injection layer and the electron transfer layer, a vacuum evaporation method, an LB method, an ink jet method, a printing method, and a method of coating the compound(s) capable of injecting or transferring electrons in the form of a solution or dispersion in an appropriate solvent (using, e.g., a spin coating, cast coating or dip coating method) can be adopted. In a case of adopting the coating method, the electron-injecting or transferring compounds can be dissolved or dispersed in the presence of a resin component. Examples of a resin component usable therein include the same resins as employed for the hole injection and transfer layers.

The materials for a protective layer may be any substances so long as they have a function capable of inhibiting the invasion of a device deterioration promoter, such as moisture or oxygen, into the device. Examples of such a substance include metals, such as In, Sn, Pb, Au, Cu, Ag, Al, Ti and Ni; metal oxides, such as MgO, SiO, $SiO_2$, $Al_2O_3$, GeO, NiO, CaO, BaO, $Fe_2O_3$, $Y_2O_3$ and $TiO_2$; metal fluorides, such as $MgF_2$, LiF, $AlF_3$ and $CaF_2$; polyethylene, polypropylene, polymethyl methacrylate, polyimide, polyurea, polytetrafluoroethylene, polychlorotrifluoroethylene, polydichlorodifluoroethylene, copolymer of chlorotrifluoroethylene and dichlorodifluoroethylene, copolymers prepared by polymerizing a mixture of tetrafluoroethylene and at least one comonomer, and fluorine-containing copolymers having cyclic structures on the main chain; a water-absorbing substance having a water absorption rate of at least 1%; and a moistureproof substance having a water absorptivity of at most 0.1%.

The protective layer also has no particular restriction as to the formation method, but any of a vacuum evaporation method, a sputtering method, a reactive sputtering method, a molecular beam epitaxy (MBE) method, a cluster ion beam method, an ion plating method, a plasma polymerization method (high frequency excitation ion plating method), a plasma chemical vapor deposition (CVD) method, a laser CVD method, a heat CVD method, a gas source CVD method, a coating method and an ink jet method can be adopted for the formation thereof.

In certain embodiments of the present invention, layers also may be present that are hole transporting and electron blocking, or electron transporting and hole blocking. Such layers that include a blocking function are included in the general terms hole transport layer, electron transport layer, and charge transport layer, as used herein. Additional layers, often termed charge injection layers, or buffer layers, may also be used in the practice of the present invention. An electron injection layer or hole injection layer may be used to provide a better contact to the cathode and anode respectively, particularly to provide an ohmic contact. Injection layers or buffer layers are used to reduce the roughness of the anode or cathode, or to better match the work function of the anode or cathode to the next organic layer. Non-limiting examples of hole injection layers or buffer layers are polythiophene, polyaniline, chemically bound silane coatings, and $(CF)_x$.

Non-limiting particular examples of hole injection or buffer layers are Baytron P® (Bayer) a brand of PEDOT (polyethylenedioxythiophene), Ormecon® (Ormecon) a brand of polyaniline. (PANI). Non-limiting examples of electron injection or buffer layers are aluminum tris(8-hydroxyquinoline), LiF, $BaF_2$ and CsF.

It is expected that the stability of the ON or OFF state will be enhanced within a polymer matrix. Also polymers matrices will allow cost-effective plastic processing of materials. The matrix typically comprises a polymer, but may be an oligomer, or discrete molecules. The matrix will accept electrons and/or holes from the electrodes and transport them toward the center of the device where they recombine to produce an excited electronic state in the matrix. Specifically novel benzotriazole monomers, oligomers, and polymers may be embedded within a fluorescent organic matrix, producing a system wherein the organic matrix may be elevated to an excited state, which then transfers its energy to the benzotriazole compounds which then emit light. Materials that fluoresce well tend to also electroluminesce well, and are thus good candidates for the matrix. The band gap of the matrix (or in other terms the HOMO-LUMO difference) will determine the energy of the excited state, and how much energy is available to excite the luminescent benzotriazole material.

Alternatively, the switchable molecules or polymers of the present invention can be blended with other molecules or polymers for any desired reason including electronic tuning, enhancement of charge mobility, cost, etc.

The terms "OLED display devices," "OLED displays" and "organic light-emitting devices" are used in their art-recognized meaning of a display device comprising organic light-emitting diodes (OLEDs) as pixels formed into two-dimensional arrays. Passive matrix (PM) and active matrix (AM) screens are two fundamental types of OLED display assembly.

In a passive-matrix OLED (PM-OLED) of conventional construction, a plurality of laterally spaced light-transmissive anodes, for example indium-tin-oxide (ITO) anodes, are formed as first electrodes on a light-transmissive substrate such as, for example, a glass substrate. Two or more organic layers are then formed successively, for example, by physical vapor deposition of respective organic materials from respective sources, within a chamber held at reduced pressure, typically less than $10^{-3}$ Torr. A plurality of laterally spaced cathodes is deposited as second electrodes over an uppermost one of the organic layers. The cathodes are oriented at an angle, typically at a right angle, with respect to the anodes. Such conventional passive-matrix OLEDs are operated by applying an electrical potential (also referred to as a drive voltage) between appropriate columns (anodes) and, sequentially, each row (cathode). When a cathode is biased negatively with respect to an anode, light is emitted from a pixel defined by an overlap area of the cathode and the anode, and emitted light reaches an observer through the anode and the substrate.

In an active-matrix OLED (AM-OLED), an array of anodes are provided as first electrodes by thin-film transistors (TFTs) which are connected to a respective light-transmissive portion. Two or more organic layers are formed successively by vapor deposition in a manner substantially equivalent to the construction of the aforementioned passive matrix device. A common cathode is deposited as a second electrode over an uppermost one of the organic layers. The construction and function of an active matrix organic light-emitting device is described, for example, in U.S. Pat. No. 5,550,066, the disclosure of which is herein incorporated by reference.

A "color OLED device" emits light of at least one color. The term "multicolor" is employed to describe a display panel that is capable of emitting light of a different hue in different areas. In particular, it is employed to describe a display panel that is capable of displaying images of different colors. These areas are not necessarily contiguous. The term "full color" is employed to describe multicolor display panels that are capable of producing light in the red, green, and blue regions of the visible spectrum and displaying images in any combination of hues. The red, green, and blue colors constitute the three primary colors from which all other colors can be generated by appropriately mixing these three primaries. The term "hue" refers to the intensity profile of light emission within the visible spectrum, with different hues exhibiting visually discernible differences in color.

The term "display" or "display panel" is employed to designate a screen capable of electronically displaying video images or text. The term "pixel" is employed in its art-recognized usage to designate an area of a display panel that can be stimulated to emit light independently of other areas. The pixel or subpixel is generally used to designate the smallest addressable unit in a display panel. For a monochrome display, there is no distinction between pixel or subpixel. The term "subpixel" is used in multicolor display panels and is employed to designate any portion of a pixel which can be independently addressable to emit a specific color. For example, a blue subpixel is that portion of a pixel which can be addressed to produce blue light. In a full-color display, a pixel generally comprises three primary-color subpixels, namely blue, green, and red. The term "pitch" is used to designate the distance separating two pixels or subpixels in a display panel. Thus, a subpixel pitch means the separation between two subpixels.

Further, it is contemplated that the novel materials and processes described herein will be used in sensors, switches, or components thereof. Luminescent sensors may be used, for example, in applications such as detection of liquid or gaseous material (e.g. nerve gases), measurement of concentration of a liquid or gaseous material (e.g., measurement of the oxygen concentration in a subject's breath, or glucose concentration in a subject's blood), measurement of temperature, and detection of ionizing radiation.

Luminescent sensors used to detect the presence of an analyte operate on the principle of chemical reaction between the reactive sensor material (e.g., those of the present invention) and the analyte. This reaction transforms the reactive sensor material from the OFF to the ON state allowing for rapid detection by fluorescence. Specifically, the switchable hydroxybenzotriazole materials of the present invention can be used to detect any material that will react with the hydroxy group of the hydroxybenzotriazole thereby transforming it from the OFF state to the ON state. For example, a commercial benzotriazole UV absorber (Tinuvin-P, Ciba), which does not emit visible light when excited with a UV source at 365 nm, emits strong blue light when excited with the same UV source after being reacted with diethyl phosphochloridate, an analogue of a nerve agent (See Example 22).

Luminescent sensors used to measure concentration operate on the concept of measuring the luminescent intensity or lifetime of the radiation emitted by the excitation of the analyte-sensitive molecule. The sensor irradiates the indicator molecule with light at a wavelength band corresponding to a region of analyte-dependent absorbance by the indicator molecule. Luminescent emission is measured by the signal-measuring component. The ambient analyte concentration is determined by known techniques as a function of the measured luminescent emission.

Luminescent materials used as temperature sensors, in response to a pulse of radiation that causes them to commence luminescence, exhibit a decay of their luminescence, after termination of the exciting pulse, with a rate which varies with temperature. Determination of the change in the luminescent properties of the sensor material due to radionuclide damage may be effected by illuminating the irradiated sensor material with ultraviolet light of the appropriate frequency to cause the sensor molecule to fluorescence. The fluorescence spectrum is then analyzed to determine the relative proportions of monomer and excimer.

Besides the sensory role, novel materials described herein also have potential for information processing because their emission can be switched between two distinguishable states by environmental stimuli. For a review of the general use of luminescent materials in sensors and switches see, e.g., Chem. Rev., 97, 1515-1566, (1997).

The novel materials and processes described herein will also be used as light sources for lighting applications (e.g., in light fixtures, lamps, etc.) Various electric appliances that employ as light sources the luminescent device of the present invention can be also thin and light-weight and can operate consuming less power. Light sources of liquid crystal display devices, such as back light or front light, or light sources of lighting fixtures are included as applications of the luminescent devices of the present invention. Accordingly, the luminescent device can be thin, light-weight, and consume less power. One embodiment of the present invention is to achieve light sources to make lighting devices able to emit and diffuse light beams suitably directed and directable when excited by a suitable electric, electromagnetic, or chemical impulse.

The novel materials and processes described herein will also be used as lasers and as components in lasers (e.g., as lasers for fiber optical communicators). As used herein the term "laser" refers to any of several devices that emits one or more discrete frequencies of highly amplified and coherent ultraviolet, visible, or infrared radiation, including but not limited to a laser diode or circuit, a light emitting diode (LED), or other optically transmitting devices. Further applications related hereto include optical computers.

The novel materials and processes described herein will also be used in bioseparation, biotagging or biomonitoring applications in vivo and/or in vitro. For example, the novel materials described herein may be introduced as tags into living cells, which can be tracked by applying a pulse of radiation that causes the luminescent biotags to commence luminescence.

As used herein, the term "photovoltaic" refers to a material, such as the novel materials disclosed herein, that is capable of converting radiation (typically solar radiation) into electricity when the material is subjected to the incidence of radiation. See Van Nostrand's Scientific Encyclopedia, D. Considine and G. Considine eds., (7 1h Ed. 1989) at pages 2635-2636, which are hereby incorporated by reference. The photovoltaic material in its simplest form is often referred to as a "cell". In many cases the term "cell" is also used to encompass not only the compound semiconductor, but the substrate and terminals or electrodes as well. In each case the cell will have two regions, e.g. an n-type region and a p-type region, establishing a junction therebetween.

Synthetic Overview

Benzotriazole monomers of the present inventions are prepared relatively straightforwardly, generally in one to two steps utilizing well-known chemical transformations. For example, the monomer T1, 2,4-Di-tert-butyl-6-(4,7-dibromo-benzotriazol-2-yl)-phenol, is prepared by a one step bromination of a low cost commercially available benzotriazole-2-yl-4,6-di-tert-butyl-phenol which is sold under the trade name Tinuvin® 320 by Ciba® Specialty Chemicals (Example 1). This monomer may be further derivatized, for example by alkylation of the phenol moiety with iodomethane to yield monomer T2 (2-(3,5-di-tert-butyl-2-methoxyphenyl)-4,7-dibromo-2H-benzotriazole, Example 2). Similarly, monomer T3 is easily prepared in two steps, first by alkylation of 1H-benzo[d][1,2,3]triazole with 1-bromohexane and then by bromination of the resulting products to yield the desired 4,7-Dibromo-2-hexyl-2H-benzotriazole (Example 3). Non-benzotriazole co-monomers used in embodiments of the present invention are well-known compounds and are either available commercially or can be prepared according to literature procedures.

Benzotriazole monomers of the present invention are readily polymerized, co-polymerized, or oligomerized, by using standard polymerization methods in the art including Yamamoto, Suzuki, Stille, Colon, etc., polymerization techniques. Aryl to aryl coupling reactions are but one example of chemical transformations that can be used to prepare oligomers and polymers described herein. Aryl-aryl bond formation has been known for more than a century and was one of the first reactions carried out using a transition metal. The reaction as applied to the formation of oligomers and polymers has been a subject of several excellent reviews, e.g., see Roncali, *J. Chem. Rev.* 1992, 92, 711, and Hassan, M. et al. *Chem. Rev.,* 2002, 102, (5), 1359-1470, each of which is incorporated herein by reference. Specifically, polymerizations and oligomerization of aromatic substrates can be carried out by employing magnesium, zinc, mercury, tin or boron derivatives with various catalysts.

A. Polymerizations of Aromatic Substrates Involving Magnesium Derivatives

Heteroarene dihalides may be coupled stepwise with heteroaryl Grignard reagents catalyzed by a palladiumphosphine complex (PdCl$_2$-dppb) yielding various mixed heteroarene oligomers. By this method, mixed heteroarene oligomers can be produced with control of the number, kind, and position of linked heteroarenes. See, e.g., Minato, A.; Suzuki, K.; Tamao, K.; Kumada, M. *J. Chem. Soc., Chem. Commun.* 1984, 511; Kauffman, J. M. *Synthesis* 1999, 918; Mikami, S.; Sugiura, K.-I.; Sakata, Y. *Chem. Lett.* 1997, 833; Nakayama, J.; Ting, Y.; Sugihara, Y.; Ishii, A. *Heterocycles* 1997.

B. Polymerizations of Aromatic Substrates Involving Zinc Derivatives

The analogous reaction, involving the use of zinc as an activating metal instead of magnesium, has been reported for the preparation of di(4-pyridyl)thiophene oligomers as models for transmembrane molecular conductors. See, e.g., Albers, W. M.; Canters, G. W.; Reedijk, J. *Tetrahedron* 1995, 51, 3895. In general, palladium-catalyzed cross coupling of zinc derivatives is not efficient for polymerization but it can allow the preparation of various important oligomers. Recently, such syntheses of initial shorter oligomers have been described for cyclic oligophenylene (Iyoda, M.; Kondo, T.; Nakao, K.; Hara, K.; Kuwatani, Y.; Yoshida, M.; Matsuyama, H. *Org. Lett.* 2000, 2, 2081); alkyl end-capped oligoheterocycles (Luo, F. T.; Bajji, A. C. *J. Chin. Chem. Soc.* 2000, 47, 257); and a green electroluminescent conjugated polymer: poly-[2,7-bis(4-hexylthienyl)-9,9-dihexylfluorene] (Pei, J.; Yu, W. L.; Huang, W.; Heeger, A. J. *J. Chem. Soc., Chem. Commun.* 2000, 1631).

C. Polymerizations of Aromatic Substrates Involving Mercury Derivatives

Curtis et al. described the polymerization via the preparation of organomercurials. This synthesis is based on the coupling of 2,5-bis(chloromercurio)-3-alkylthiophenes in the presence of copper and catalytic quantities of $PdCl_2$. (McClain, M. D.; Whittington, D. A.; Mitchell, D. J.; Curtis, M. D. *J. Am. Chem. Soc.* 1995, 117, 3887) Soluble random homopolymers were synthesized in good yield (65-80%) from these difunctional monomers, indicating that this coupling reaction showed very little steric discrimination.

D. Oligo- and Polymerizations of Aromatic Substrates Using Organostannyl Derivatives The Stille cross-coupling reaction has been used for the synthesis of several oligopyridines. Cardenas and Sauvage developed a direct synthesis of 2,6-oligopyridines by cross coupling of pyridyl stannanes with bromopyridines in the presence of $Pd(PPh_3)_2Cl_2$. (Cardenas, D. J.; Sauvage, J.-P. *Synlett* 1996, 916) Although the prepared compounds possessed coordinating ability, the authors did not observe any problems due to lack of compatibility of the substrates and products with the catalyst.

Similar Stille cross-coupling oligo- and polymerizations have been accomplished, for example, by Lehmann, U.; Henze, O.; Schluter, A. D. *Chem. Eur. J.* 1999, 5, 854; Schubert, U. S.; Eschbaumer, C.; Weidl, C. H. *Synlett* 1999, 342; Bates, G. B.; Parker, D. *Tetrahedron Lett.* 1996, 37, 267; Zhu, S. S.; Swager, T. M. *J. Am. Chem. Soc.* 1997, 119, 12568; Zhu, S. S.; Kingsborough, R. P.; Swager, T. M. *J. Mater. Chem.* 1999, 9, 2123; Zotti, G.; Zecchin, S.; Schiavon, G.; Berlin, A.; Penso, M. *Chem. Mater.* 1999, 11, 3342; Dondoni, A.; Fogagnolo, M.; Medici, A.; Negrini, E. *Synthesis* 1987, 185; Hucke, A.; Cava, M. P. *J. Org. Chem.* 1998, 63, 7413; Mitschke, U.; Osteritz, E. M.; Debaerdemaeker, T.; Sokolowski, M.; Bauerle, P. *Chem. Eur. J.* 1998, 4, 2211; Tamao, K.; Ohno, S.; Yamaguchi, S. *J. Chem. Soc, Chem. Commun.* 1996, 1873; Wu, R.; Schumm, J. S.; Pearson, D. L.; Tour, J. M. *J. Org. Chem.* 1996, 61, 6906; Bao, Z.; Chan, W. K.; Yu, L. *J. Am. Chem. Soc.* 1995, 117, 12426; Delnoye, D. A. P.; Sijbesma, R. P.; Vekemans, J. A. J. M.; Meijer, E. W. *J. Am. Chem. Soc.* 1996, 118, 8717; Bonachrine, M.; Le're-Porte, J.-P.; Moreau, J. J. E.; Serein-Spirau, F.; Toreilles, C. *J. Mater. Chem.* 2000, 10, 263; Miller, L. L.; Yu, Y. *J. Org. Chem.* 1995, 60, 6813; and Barbarella, G.; Favaretto, L.; Sotgiu, G.; Zambianchi, M.; Antolini, L.; Pudova, O.; Bongini, A. *J. Org Chem.* 1998, 63, 5497. Many of these researchers have investigating the possibility of performing Stille-coupling reactions in the preparation of functional polymers and found that this reaction can indeed be performed under mild conditions and generally produces high yields.

E. Suzuki Aryl-Aryl Cross Coupling Applied for Oligo- or Polymerization

The Suzuki polycondensation has been intensively developed for the synthesis of aryl oligomers, polyarylenes, and related polymers. Indeed, this procedure allows the preparation of regiospecific polymers with high molecular weights and further shows a high compatibility with various functional groups. The Pd-catalyzed coupling of polyhalo-substituted aromatic compounds with aromatic boronic acids has been widely used for the preparation of functionalized oligomers. For example, Gronowitz described the preparation of various heterocyclic compounds containing thiophene, furan, selenophene, pyridine, and thiazole rings by the $Pd(PPh_3)_4$-catalyzed coupling of dihalo-substituted heterocyclic compounds with heterocyclic boronic acids, using sodium bicarbonate as the base and a 1,2-dimethoxyethane/water mixture as the solvent. (Gronowitz, S. *Chem. Scr.* 1987, 27, 535; Gronowitz, S.; Peters, D. *Heterocycles* 1990, 30, 645).

The repetitive use of the Suzuki coupling was described by Bidan et al. for the stepwise synthesis of a series of head-to-tail alkyl-substituted oligothiophenes (Bidan, G.; De Nicola, A.; Ene'e, V.; Guillerez, S. *Chem. Mater.* 1998, 10, 1052). In their iterative synthesis, the authors chose to introduce a chloride atom as the blocking group to protect one of the two reactive ortho-positions to the sulfur throughout the entire synthesis. Since heteroaryl chlorides were unreactive toward boronic acids, when using $Pd(PPh_3)_4$ as the catalyst, a regioselective synthesis became possible. Oligomers, up to the hexamer, were obtained by this method with yields varying around 80%. The Suzuki-coupling reaction has since been widely used for the preparation of polymers. For example, and following the procedure they described for the preparation of oligomers, Guillerez and Bidan prepared a polymerizable precursor to obtain regioregular poly(3-octylthiophene) (Guillerez, S.; Bidan, G. *Synth. Met.* 1998, 93, 123). The polymerization reaction was then carried out by homocoupling this bifunctionalized monomer in a palladium-catalyzed Suzuki reaction using 1 mol % palladium acetate and 1.5 equiv of potassium carbonate as the base. Poly-(3-octylthiophene), containing around 96% head-to-tail couplings (determined from NMR experiments) and with an average molecular weight of 27 000 g/mol, was obtained in a 55% yield after the removal of short-length oligomers.

Similar Suzuki oligo- and polymerizations have been accomplished, for example, by Yamaguchi, S.; Goto, T.; Tamao, K. *Angew. Chem., Int. Ed.* 2000, 39, 1695; Galda, P.; Rehahn, M. *Synthesis* 1996, 614; Frahn, J.; Karaya, B.; Schäfer, A.; Schlüter, A.-D. *Tetrahedron* 1997, 53, 15459; Sakai, N.; Brennan, K. C.; Weiss, L.; A.; Matile, S. *J. Am. Chem. Soc.* 1997, 119, 8726; Robert, F.; Winum, J.-Y.; Sakai, N.; Gerard, D.; Matile, S. *Org. Lett.* 2000, 2, 37; Wallow, T. I.; Novak, B. M. *J. Am. Chem. Soc.* 1991, 113, 7411; Kowitz, C.; Wegner, G. *Tetrahedron* 1997, 53, 15553; Tour, J. M.; Lamba, J. J. S. *J. Am. Chem. Soc.* 1993, 115, 4935; Goldfinger, M. B.; Swager, T. M. *J. Am. Chem. Soc.* 1994, 116, 7895; Hodge, P.;

Power, G. A.; Rabjohns, M. A. *J. Chem. Soc., Chem. Commun.* 1997, 73. See also, U.S. Pat. Nos. 6,169,163, 6,512,083, and 6,514,632. Generally, Suzuki coupling reactions are run under very mild conditions and allows for the recovery or reuse of catalysts without loss of either catalytic activity or enantioselectivity.

It will be clear to those skilled in the art that each reaction type requires specific monomers and has specific limitations. For example, the Suzuki reaction generally requires both halide and boron type monomers, either as an AA, BB pair of monomers, as an AB monomer or a mixture of these, and preferably the halide is selected from chloro, bromo and iodo, more preferably the halide is selected from bromo and iodo. For the Colon coupling only a single type of monomer is required, i.e. a dihalo monomer, and the halide order of preference is Cl>Br>I, and protic and nitro groups are not tolerated. The Yamamoto (stoichiometric) type coupling requires stoichiometric quantities of nickel (0) and does not use an additional reducing agent. The Yamamoto (catalytic) type coupling requires preparation of a Grignard reagent monomer, typically derived from a dibromo or dichloro pre-monomer. The term "Yamamoto" as used herein shall include both Yamamoto (stoichiometric) and Yamamoto (catalytic) coupling reactions. The Stille coupling requires a halo monomer and an aryl tin monomer, either as an AA BB pair, an AB monomer, or mixture of these. Other method of aryl-aryl couplings are known in the art, any of which may be used in the practice of the present invention.

Polymerizations and oligomerizations detailed in the Examples take advantage of the Suzuki coupling reaction. Specifically, 2,4-di-tert-butyl-6-(4,7-dibromo-benzotriazol-2-yl)-phenol was copolymerized with 2,5-bis-hexyloxy-1,4-benzenebisboronic ethylene glycol ester and 1,4-dibromo-2,5-bis-hexyloxy-benzene in the presence of tetrakis(triphenylphosphine) palladium and potassium carbonate in toluene/water containing a phase transfer catalyst. (Example 14) Similarly, 2,4-di-tert-butyl-6-(4,7-dibromo-benzotriazol-2-yl)-phenol, 2,5-Dihexyloxy-1,4-benzenediboronic ethyleneglycol ester, and 4,4'-dibromotriphenylamine were copolymerized in the presence of tetrakis(triphenylphosphine) palladium and potassium carbonate in DMF. (Example 15)

These and other aspects of the present invention will be further appreciated upon consideration of the following Examples, which are intended to illustrate certain particular embodiments of the invention but are not intended to limit its scope, as defined by the claims.

The weight-average molecular weights, $M_W$, were estimated by gel permeation chromatography (GPC) employing monodisperse polystyrene calibration standards and THF as eluent. The GPC columns used were filled with crosslinked polystyrene gel (Styragel HT4; Waters Corp.).

All publications and patent applications mentioned in this specification are indicative of the level of skill of those skilled in the art to which this invention pertains. All publications and patent applications mentioned in this specification are herein incorporated by reference to the same extent as if each individual publication or patent application mentioned in this specification was specifically and individually indicated to be incorporated by reference.

EXAMPLES

Example 1

2,4-Di-tert-butyl-6-(4,7-dibromo-benzotriazol-2-yl)-phenol (Monomer T1)

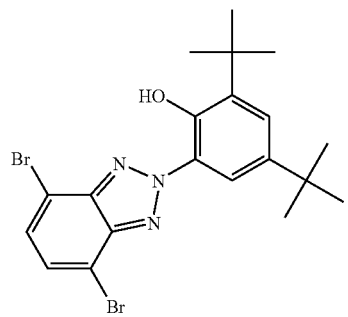

Benzotriazol-2-yl-4,6-di-tert-butyl-phenol (48.6 g, 0.15 mol) was placed in a 3-neck 1-L flask equipped with a stir bar, an addition funnel, a reflux condenser, and a flow control adapter. Through a three-way connecting tube the nitrogen flow was diverted to the flask via the condenser and to an oil bubbler. The bubbler was connected to a filtration flask containing aqueous sodium hydroxide. Hydrobromic acid (45% in acetic acid, 300 mL) was added. The system was purged with nitrogen for 15 min. The slurry was heated to 110° C. for 0.5 h and bromine (23.2 mL, 0.45 mol, 3 equivalent) was added dropwise. The addition was completed in 1 h and the mixture was stirred for an additional 1 h. Three more portions of bromine (3×23.2 mL, 3×0.45 mol) were added and stirring continued for one more hour. The flask was cooled to room temperature. Water (200 mL) was added and the mixture was filtered. The solid was collected and dissolved in dichloroethane (0.5 L). The solution was neutralized first with NaOH (aq) and then with $NaHCO_3$ (aq). The organic layer was dried over magnesium sulfate. The drying agent was filtered off. The solvent of the filtrate was removed by rotary evaporation resulting in a viscous oil. Upon addition of acetone (200 mL) yellow crystalline solid was produced. The product was purified by recrystallization from acetone. Purity: 99+%. Yield: 5.1%. Melting point 244-246° C.

Example 2

2-(3,5-di-tert-butyl-2-methoxyphenyl)-4,7-dibromo-2H-benzotriazole (Monomer T2)

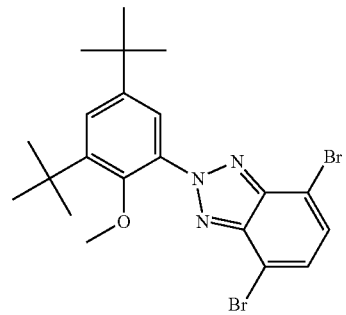

2,4-Di-tert-butyl-6-(4,7-dibromo-benzotriazol-2-yl)-phenol (Monomer T1) (1.0 g, 2.08 mmol) and potassium carbonate (0.431 g, 96% GC purity, 3.12 mmol) were mixed in anhydrous DMF (20 mL) in a round-bottomed 100-mL flask. The flask was capped with a rubber septum and purged with nitrogen for 0.5 h. The mixture was heated to 65° C. and iodomethane (0.591 g, 4.16 mmol) was added. The mixture was stirred at 60-65° C. for 1 h. The flask was cooled to room temperature. DCM (20 mL) and water (20 mL) were added and the organic phase was separated and the aqueous phase extracted with DCM (20 mL). All the organic phases were combined and washed with water (3×20 mL) and brine (20 mL). The solution was dried over magnesium sulfate and filtered. The filtrate was evaporated to dryness with a rotary evaporator. The product was crystallized from DCM/hexanes and filtered. Purity: 99% (GC). Yield: 34%.

Example 3

4,7-Dibromo-2-hexyl-2H-benzotriazole

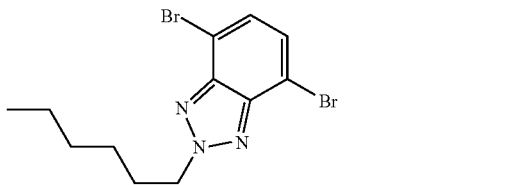

(Monomer T3)

1H-benzo[d][1,2,3]triazole (11.9 g, 0.10 mmol) and potassium carbonate (27.6 g, 0.20 mmol) were placed in a 250-mL round-bottom flask and purged with nitrogen. DMF (100 mL) was added and the flask was heated at 70° C. for 2 h. 1-Bromohexane (15.4 mL, 0.11 mol) was added and the suspension was stirred at 70° C. for 2 h. The solution was cooled to room temperature and DCM (200 mL) and water (200 mL) were added. The organic phase was separated and washed with water and brine. The solution was dried over magnesium sulfate and filtered. The solvent of the filtrate was removed under reduced pressure. The excess bromohexane was distilled off under high vacuum. GC/MS indicated the formation of two isomers with a ratio of ca 1:1. The mixture of the two isomers was placed in a 250-mL round-bottomed flask. Diethyl ether (50 mL) and HCl (2M in ether, 50 mL, 100 mmol) were added and the solution stirred for 15 min. The supernatant was transferred to another flask and neutralized with aqueous sodium bicarbonate and then washed with water (50 mL). The solution was dried over magnesium sulfate and filtered. The solvent was removed under reduced pressure and the product dried under high vacuum for 2 h. The product consisted of isomer 1 (77%) and II (23%).

The product was placed in a 3-neck flask equipped with a stir bar, an addition funnel, a Friedrich condenser, and a rubber septum and DMF (25 mL) was added. The flask was purged with nitrogen for 15 min. Bromine (5.36 mL, 104 mmol) was added dropwise to the solution. The flask was heated at 110° C. for 4 h and a second batch of bromine (5.36 mL, 104 mmol) was added and the flask heated for an additional 1 h at 110° C. The mixture was cooled to room temperature and then poured into an ice slurry (100 g). DCM (100 mL) and NaOH (aqueous, 2M, 125 mL) were added and the organic layer was separated and washed with water and brine. The solution was dried over magnesium sulfate and filtered. The solvent was removed with a rotary evaporator. The crude material was purified with a silica gel column (8 cm×22 cm, D×L) using DCM as eluent. Removal of solvent resulted in an oily product which was crystallized from hexanes. The product was further purified by recrystallization. Purity: 98%. Yield: 25%.

Example 4

1,4-Dihexyloxybenzene

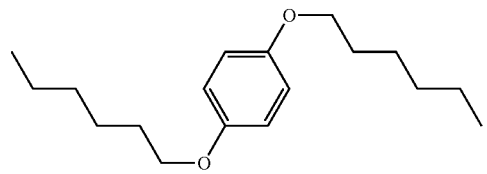

To a 3-L, oven-dried, round-bottom flask flushed with nitrogen and equipped with a stir bar was added ethanol (1000 mL), 1,4-dihydroquinone (110 g) and potassium hydroxide (154 g) at room temperature. After 30 min of stirring, 1-bromohexane (495 g) was added dropwise. Subsequently the reaction mixture was heated in an oil bath at 65° C. for 4 hours. After cooling to room temperature, the clear ethanol solution was separated from the inorganic solids and concentrated by a rotary evaporator. The inorganic solid was first washed with hexane (2×250 mL) followed by dissolution in 1 L water and extraction with hexane (2×250 mL). The hexane extracts and the main product in ethanol were combined and washed with water (2×250 mL). After removal of the solvent, the crude product was recrystallized with methanol. Colorless crystals of product were collected. Purity: 99+%. Yield: 76%.

Example 5

2,5-Dihexyloxy-1,4-dibromobenzene

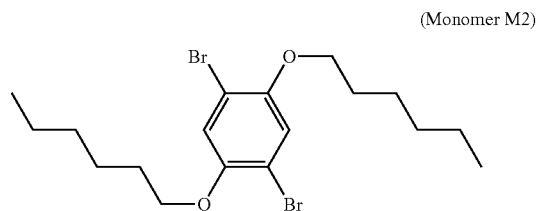

(Monomer M2)

To a 1-L round-bottom flask equipped with a magnetic stirrer was added 1,4-dihexyloxybenzene (200 g) and carbon tetrachloride (220 mL). When the crystals were completely dissolved, bromine (90 mL) in carbon tetrachloride (140 mL) was added over a period of 4 hour. The generated HBr was absorbed by a sodium hydroxide solution. After the addition was complete, the reaction mixture was continuously stirred overnight at room temperature. The excess bromine was quenched with aqueous sodium hydroxide. The organic layer was separated and washed with dilute aqueous NaOH and water separately. After removal of the solvent, the crude product was recrystallized twice with 1 L ethanol. Purity: 99+%. Yield: 84%.

Example 6

2,5-Dihexyloxy-1,4-benzenediboronic acid

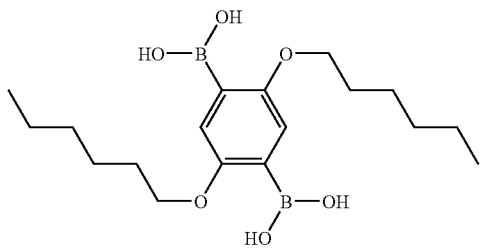

An oven-dried, 1 L three-necked round-bottom flask was equipped with a stir bar, rubber septum and an addition funnel. The flask was charged with 43.6 g of 2,5-dihexyloxy-1,4-dibromobenzene (M2) and flushed with $N_2$. THF (500 mL) was added and the solution cooled to −80° C. in a liquid nitrogen/hexane bath. BuLi (10M, 33 mL) was added dropwise and the mixture was stirred at −80° C. for one hour before it was allowed to warm to room temperature. The reaction mixture was cooled to −80° C. again, while 100 mL of $B(OMe)_3$ was added. This mixture was again allowed to warm to room temperature and stirred overnight. The mixture was hydrolyzed by addition of 300 mL of 2M HCl. The white precipitate was filtered and washed with deionized water. The crude product was recrystallized from ethanol and dried under vacuum overnight.

Example 7

2,5-Dihexyloxy-1,4-benzenediboronic ethyleneglycol ester (Monomer B2)

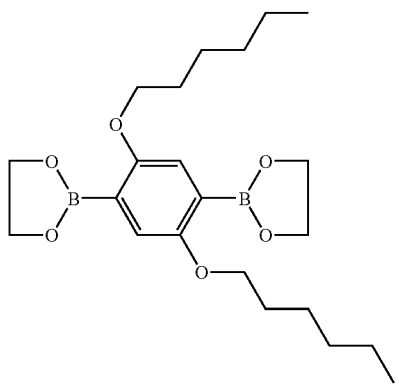

In a 250 mL flask, 2,5-Dihexyloxy-1,4-benzenediboronic acid (25 g) prepared above was heated with ethylene glycol (50 mL) at 130° C. in an oil bath for 1.5 hours. Subsequently 60 mL of toluene was added and refluxed using a Dean-Stark trap for an additional 1.5 hours. After removal of toluene and cooling down to room temperature, the expected product was separated by filtration and washed with methanol. The product was further purified by recrystallization with a dichloromethane-hexane (1:4) mixture. Purity: 99+%. Yield: 16%.

Example 8

2,5-Dihexyl-1,4-benzenediboronic ethyleneglycol ester (Monomer B1)

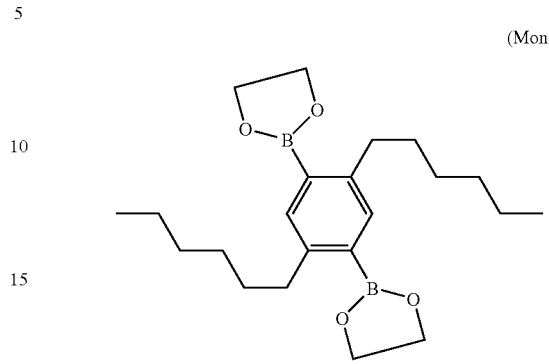

2,5-Dihexyl-1,4-dibromobenzene was purchased from Frontier Chemical Company. Its boronic acid was prepared according to Rehahn et al., Makromol. Chem. 191, 1991-2003 (1990). Esterification of the boronic acid was performed according to procedure described above.

Example 9

4,4'-dibromodiphenylamine

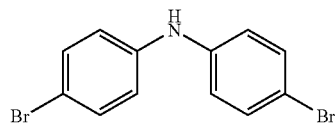

Diphenylamine (39.8 g, 0.235 mol) was charged into a flask containing DMSO (200 mL) and allowed to dissolve. HBr (48% aqueous, 150.0 mL, 1.33 mol) was added dropwise resulting in a cloudy white mixture, which was stirred overnight whereby a white solid precipitated. The solid was collected by vacuum filtration and washed with DI water (3×50 mL) followed by recrystallization from hexanes to yield white crystalline needles, Purity: 99+% (GC).

Example 10

4,4'-dibromotriphenylamine (Monomer M5)

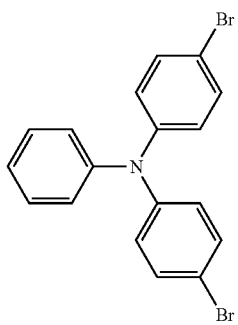

In an oxygen-free glovebox, a 250 mL flask was charged with 4,4'-dibromodiphenylamine (15.0 g, 45.8 mmol), iodobenzene (18.7 g, 91.7 mmol), 1,10-phenanthroline (0.827 g, 4.59 mmol), CuCl (0.454 g, 4.59 mmol), KOH (15.4 g, 275 mmol), and toluene (125 mL). The flask was sealed and removed from the glovebox and heated to 130° C. and stirred for 24 hr. The flask was then removed from the oil bath and allowed to cool to room temperature. The solids were filtered off and the solvent was removed to yield a bluish oily substance, which was passed through silica gel column using toluene as the eluant. The fractions were collected and the solvent was removed followed by vacuum distillation at 160° C. for 30 min to remove the remaining iodobenzene to afford a blue solid. This solid was further purified by a second silica plug column using hexanes as the eluant. The colorless clear fractions were combined and the solvent removed to yield the desired product. Purity: 99+%.

Example 11

3,6-Dibromo-9-phenylcarbazole (Monomer M6)

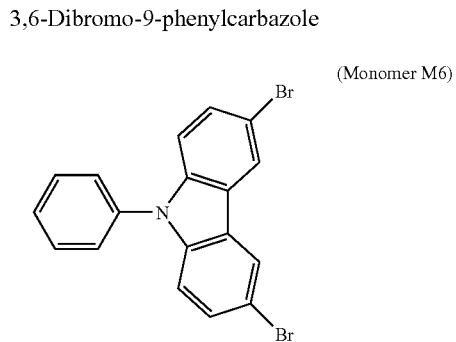

9-Phenylcarbazole (2.000 g, 8.220 mmol) was suspended in 15 mL glacial acetic acid in a 125 ml 3-neck round bottom flask equipped with an addition funnel and a condenser. The reaction was under $N_2$ blanket. Bromine (0.880 ml, 17.262 mmol) mixed with 15 mL glacial acetic acid was added dropwise and stirred at 0° C. Upon completion of the addition the reaction was allowed to warm to room temperature and stirred for about 5 hours. Dichloromethane (100 mL) was added, and stirred vigorously until all the solids dissolved. Two phases were separated in the separation funnel. The acid layer was extracted twice with 50 mL dichloromethane. The organic layers were combined and washed with brine until the pH=7. The organic layers were dried over $MgSO_4$ and filtered. Solvent was removed under vacuum. The crude product was then recrystallized from dichloromethane. Yield: 56.9%. M.P.: 162.7-163.6° C.

Example 12

2,4-di-tert-butyl-6-(4,7-di(thiophen-2-yl)-2H-benzotriazol-2-yl)phenol

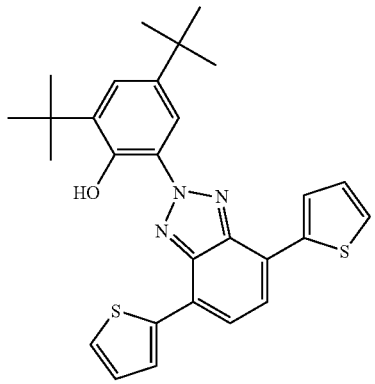

2,4-Di-tert-butyl-6-(4,7-dibromo-benzotriazol-2-yl)-phenol (1.0 mmol) and dichlorobis(triphenylphosphine)palladium (0.02 mmol) were placed in a 100-mL round-bottomed flask. The flask was capped with a rubber septum and purged with nitrogen for 5 min. THF (10 mL, anhydrous) and tributyl (thiophen-2-yl) stannate (2.2 mmol) were then added in that order. The flask was heated at 80° C. and stirred for 6 hrs. The reaction mixture was cooled to room temperature and solvent was removed with a rotary evaporator. The residue was crystallized from DCM/hexanes. A yellow product was obtained. Yield: 70%. Fluorimetry of a dilute solution of the product in toluene showed strong emission with a peak at 499 nm, FIG. 3.

Example 13

2-(4,7-bis(5-bromothiophen-2-yl)-2H-benzotriazol-2-yl)-4,6-di-tert-butylphenol

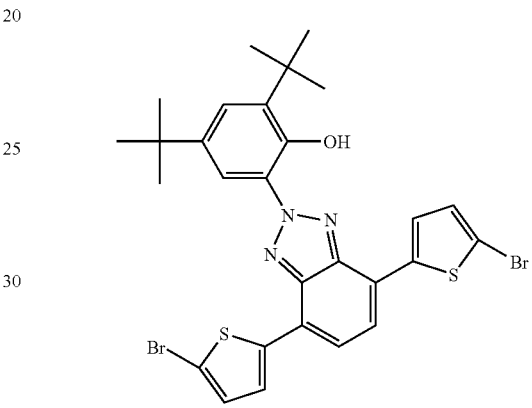

2,4-di-tert-butyl-6-(4,7-di(thiophen-2-yl)-2H-benzotriazol-2-yl)phenol (0.70 mmol) and N-bromosuccinimide (1.40 mmol) were placed in a 100-mL round-bottom flask. Chloroform (20 mL) and AcOH (10 mL) were added. The flask was purged with nitrogen for 5 min. and the yellow suspension was stirred under nitrogen at room temperature for 16 hrs. A light yellow suspension formed. A yellow solid was collected by filtration and washed with methanol (20 mL). The solid was dissolved in dichloromethane (200 mL) and washed with water (2×100 mL) and brine (100 mL) and dried over $MgSO_4$. Solvent was removed under reduced pressure and the product was further dried in a vacuum oven at 100° C. for 2 hrs. Yield: 71%.

Example 14

Copolymerization of 1,4-dibromo-2,5-bis-hexyloxy-benzene, 1,4-dibromo-2,5-bis-hexyloxy-benzene, and 2,4-di-tert-butyl-6-(4,7-dibromo-benzotriazol-2-yl)-phenol (Preparation of Copolymer 1)

To a 40 mL glass vial, was added 2,5-bis-hexyloxy-1,4-benzenebisboronic ethylene glycol ester (B2) (0.2374 g, 0.568 mmol), 1,4-dibromo-2,5-bis-hexyloxy-benzene (M2) (0.1134 g, 0.260 mmol), and 2,4-di-tert-butyl-6-(4,7-di-bromo-benzotriazol-2-yl)-phenol (T1) (0.1251 g, 0.260 mmol). The vial was transferred to a glove box, toluene (0.65 mL), phase transfer catalyst (Aliquat 336®, 60% in toluene, 0.35 mL) and tetrakis(triphenylphosphine) palladium in toluene (0.0104 M, 1.0 ml) were added to the vial. The vial was sealed and transferred out of the glove box. Subsequently, 0.8 mL of 2M degassed aqueous potassium carbonate was added and the vial heated on an orbital shaker at 95° C. for 20 hours. After cooling down to room temperature, the organic layer was separated, toluene (7 mL) was added, the polymer solution was filtered, and then poured slowly into an agitated mixture of methanol-water (200 mL, 9:1 v/v). The precipitated polymer was collected by filtration, redissolved in 5 mL of toluene, and poured into a stirred mixture of methanol-acetone (2×190 mL, 3:1 v/v). The polymer was finally dried in a vacuum oven at 65° C. over night. Further characterization of the polymer by gel permeation chromatography (GPC) relative to polystyrene and photoluminescence spectrometry was carried out and the data are given in Table 1.

Example 15

Copolymerization of 2,5-Dihexyloxy-1,4-benzenediboronic ethyleneglycol ester, 4,4'-dibromotriphenylamine, and 2,4-di-tert-butyl-6-(4,7-dibromo-benzotriazol-2-yl)-phenol To a 40 mL glass vial, is added 2,5-bis-hexyloxy-1,4-benzenebisboronic ethylene glycol ester (0.2174 g, 0.520 mmol), 4,4'-dibromotriphenylamine (0.1134 g, 0.260 mmol), and 2,4-di-tert-butyl-6-(4,7-dibromo-benzotriazol-2-yl)-phenol (0.1251 g, 0.260 mmol). DMF (3 mL), tetrakis(triphenylphosphine) palladium (0.012 g), and potassium carbonate (0.221 g) were added to the vial. The vial is heated on an orbital shaker at 95° C. for 20 hours. After cooling down to room temperature, DMF (3 mL) is added, the polymer solution is filtered, and then poured slowly into an agitated mixture of methanol-water (200 mL, 9:1 v/v). The precipitated polymer is collected by filtration, redissolved in 5 mL of toluene, and poured into a stirred mixture of methanol-acetone (2×190 mL, 3:1 v/v). The polymer is finally dried in a vacuum oven at 65° C. over night.

Example 16

Copolymerization of 2,5-Dihexyloxy-1,4-dibromobenzene and 2-(3,5-di-tert-butyl-2-methoxyphenyl)-4,7-dibromo-2H-benzotriazole To a 40 mL glass vial, is added 2,5-bis-hexyloxy-1,4-dibromobenzene (0.45 g, 1.03 mmol), 2-(3,5-di-tert-butyl-2-methoxyphenyl)-4,7-dibromo-2H-benzotriazole (0.17 g, 0.343 mmol), Ni(cod)$_2$ (0.45 g, 1.63 mmol), 1,5-cyclooctadiene (0.3 mL), 2,2'-bipyridine (0.258 g, 1.64 mmol), and DMF (30 mL). The vial is heated on an orbital shaker at 70° C. for 40 hours. After cooling down to room temperature a precipitate is collected by filtration, washed with aqueous ammonia, a warm aqueous solution of ethylenediamine tetraaceticacid (EDTA, PH3), a warm aqueous solution of ethylenediaminetetraacetic acid (EDTA, PH9), and distilled water. The precipitated polymer is redissolved in 20 mL of toluene, and poured into a stirred mixture of methanol-acetone (2×190 mL, 3:1 v/v). The polymer is then dried in a vacuum oven at 60° C. overnight.

Example 17

2-(4,7-bis(4-(dimethylamino)phenyl)-2H-benzotriazol-2-yl)-4,6-di-tert-butylphenol

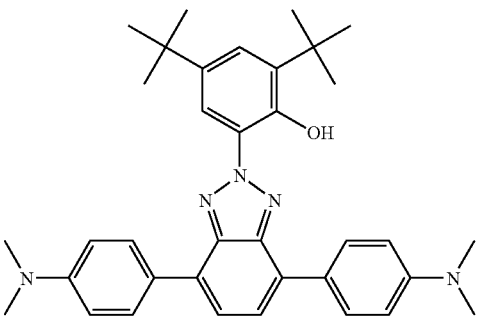

To a 40 mL glass vial, was added 4-(dimethylamino)phenylboronic acid (0.0858 g, 0.520 mmol), 2,4-di-tert-butyl-6-(4,7-dibromo-benzotriazol-2-yl)-phenol (0.1251 g, 0.260 mmol), toluene (0.65 mL), phase transfer catalyst (Aliquat 366®, 60% in toluene, 0.35 mL), tetrakis (triphenylphosphine) palladium in toluene (0.0104 M, 1.0 ml), and 0.8 mL of 2M degassed aqueous potassium carbonate. The vial was heated on an orbital shaker at 95° C. for 20 hours. After cooling to room temperature, methanol was added to the reaction mixture. Yellow crystals of product were collected after filtration and washed with DI water. Photoluminescence spectrometry of a dilute solution of the product in dichloromethane showed strong emission centered at 569 nm.

Example 18

2,4-di-tert-butyl-6-(4,7-diphenyl-2H-benzotriazol-2-yl)phenol

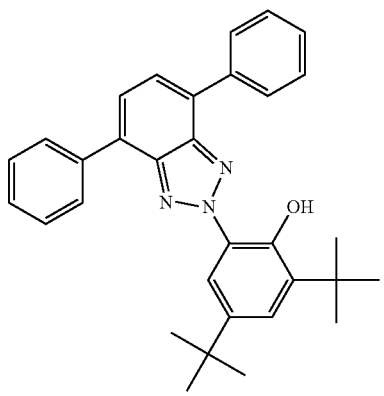

To a 40 mL glass vial, was added 4-phenylboronic acid (0.127 g, 1.04 mmol), 2,4-di-tert-butyl-6-(4,7-dibromo-benzotriazol-2-yl)-phenol (0.25 g, 0.52 mmol), toluene (0.65 mL), phase transfer catalyst (Aliquat 366®, 60% in toluene, 0.35 mL), tetrakis (triphenylphosphine) palladium in toluene (0.0104 M, 1.0 ml), and 0.8 mL of 2M degassed aqueous potassium carbonate. The vial was heated on an orbital shaker at 95° C. for 20 hours. After cooling to room temperature, methanol was added to the reaction mixture. Pale yellow crystals of product were collected after filtration and washed with DI water. Photoluminescence spectrometry of a dilute solution of the product in dichloromethane showed no visible emission.

Example 19

LED Containing Copolymer1

ITO-coated glass was coated with 100 nm PEDOT/PSS (Baytron-P from Bayer A. G. and polystyrenesulfonic acid) conducting polymer. The conducting polymer film was dried at 200° C. and then coated with a film of copolymer 1 by spin-coating a solution in THF. The copolymer 1 film was dried under Argon at 100° C. A thin layer of LiF (~5 nm) followed by a layer of Aluminum (~50-100 nm) were vapor deposited and the device was encapsulated with a glass cover using UV curable sealant. Luminance is expressed in units of $cd/m^2$, and power efficiency as lumens/watt (1 m/W).

Example 20

2-(4,7-bis(chloromethyl)-2H-benzotriazol-2-yl)-4,6-di-tert-butylphenol 2,4-Di-tert-butyl-6-(4,7-dibromo-benzotriazol-2-yl)-phenol (5 g, 15.4 mmol) is placed in a 250-mL round-bottomed flask. The flask is capped with a rubber septum and purged with nitrogen for 5 min. Cyclohexane (100 mL) is added followed by addition of bis(chloromethyl)ether (1.91 g, 16.6 mmol). The flask is heated to 65° C. and a solution of $SnCl_4$ in cyclohexane (3 g in 60 mL) is added and stirring is continued for 3 hrs. The reaction mixture is cooled to room temperature and solvent is removed with a rotary evaporator. The residue is crystallized from DCM/hexanes. Yield: 68%.

Example 21

Copolymerization of 2-(3,5-di-tert-butyl-2-methoxyphenyl)-4,7-bis(chloromethyl)-2H-benzotriazole with 1,4-bis(chloromethyl)-2,5-dimethoxybenzene To a 40 mL glass vial, is added a solution of 2-(4,7-bis (chloromethyl)-2H-benzotriazol-2-yl)-4,6-di-tert-butylphenol (0.52 g, 1.19 mmol) and 1,4-bis(chloromethyl)-2,5-dimethoxybenzene (0.28 g, 1.19 mmol) in 5 mL dry and oxygen free 1,4-dioxane. Subsequently a solution of potassium tert-butoxide (0.67 g, 6 mmol) in 6 mL of dry 1,4-dioxane is added. After 10 minutes, a solution of potassium tert-butoxide (0.53 g, 4.7 mmol) in 5 mL 1,4-dioxane is again added. The vial is heated on an orbital shaker at 95° C. for 3 hours. After cooling down to room temperature the reaction mixture is diluted with 2 mL dioxane and 1 mL acetic acid. The polymer solution is then filtered, and poured slowly into an agitated mixture of methanol-water (200 mL, 9:1 v/v). The precipitated polymer is collected by filtration, redissolved in 5 mL of toluene, and poured into a stirred mixture of methanol-acetone (2×190 mL, 3:1 v/v). The polymer is finally dried in a vacuum oven at 65° C. over night.

TABLE 1

| Co-polymer | Copolymer Composition (mol %) | Mw(×10³) (GPC) | Solution PL Peak (nm) | PL Color |
|---|---|---|---|---|
| 1 | B2(50) M2(25) T1(25) | 34 | 495 | Green |
| 2 | B2(50) T1(50) | 22 | 511 | Green |
| 3 | B2(50) M2(10) T1(40) | 53 | 499 | Green |

TABLE 1-continued

| Co-polymer | Copolymer Composition (mol %) | Mw(×10³) (GPC) | Solution PL Peak (nm) | PL Color |
|---|---|---|---|---|
| 4 | B1(50) M1(25) T1(25) | 37 | No PL | |
| 5 | B1(50) M2(25) T1(25) | 37 | No PL | |
| 6 | B1(25) B2(25) M2(25) T1(25) | 39 | 501 | Green |
| 7 | B2(50) M1(25) T1(25) | 31 | 500 | Green |
| 8 | B2(50) M2(30) T1(20) | 25 | 495 | Green |
| 9 | B2(50) M2(35) T1(15) | 32 | 493 | Green |
| 10 | B2(50) M2(40) T1(10) | 82 | 490 | Green |
| 11 | B2(50) M3(25) T1(25) | 40 | | |
| 12 | B2(50) M5(25) T1(25) | 34 | 500 | Green |
| 13 | B2(50) M5(10) T1(40) | 36 | 502 | Green |
| 14 | B1(50) M5(25) T1(25) | 38 | No PL | |
| 15 | B2(50) M6(10) T1(40) | 21 | | Green |
| 16 | B2(50) M6(25) T1(25) | 21 | | Green |
| 17 | B2(50) M5(45) T1(5) | 27 | | Green |
| 18 | B2(50) M5(40) T1(10) | 31 | | Green |
| 19 | B2(50) M5(35) T1(15) | 31 | | Green |
| 20 | B2(50) M5(30) T1(20) | 24 | | Green |
| 21 | B2(50) M5(20) T1(30) | 21 | | Green |
| 22 | B3(50) T1(50) | 70 | | Green |
| 23 | B3(50) M7(25) T1(25) | 82 | | Green |
| 24 | B2(50) M4(35) M5(10) M8(5) | 41 | 574 | Yellow |
| 25 | B2(50) M2(25) T2(25) | 16 | 497 | Green |
| 26 | B1(50) M1(25) T2(25) | 33 | 420 | Blue |
| 27 | B3(50) M5(25) T2(25) | 64 | | Green |
| 28 | B3(50) M7(25) T2(25) | 102 | | Green |
| 29 | B2(50) M2(25) T3(25) | 58 | 474 | Blue |
| 30 | B1(50) M2(25) T3(25) | 25 | 404 | Blue |
| 31 | B2(50) M5(10) T3(40) | 17 | | Blue |

The following monomer designations are used in Table 1:
B1=2-(4-(1,3,2-dioxaborolan-2-yl)-2,5-dihexylphenyl)-1,3,2-dioxaborolane;
B2=2-(4-(1,3,2-dioxaborolan-2-yl)-2,5-bis(hexyloxy)phenyl)-1,3,2-dioxaborolane;
B3=4,4,5,5-tetramethyl-2-(2-(4,4,5,5-tetramethyl-1,3,2-dioxaborolan-2-yl)-9,9-dioctyl-9H-fluoren-7-yl)-1,3,2-dioxaborolane;
M1=1,4-dibromo-2,5-dihexylbenzene;
M2=1,4-dibromo-2,5-bis(hexyloxy)benzene;
M3=2,6-dibromonaphthalene;
M4=2,5-bis(4-bromophenyl)-1,3,4-oxadiazole;
M5=4-bromo-N-(4-bromophenyl)-N-phenylbenzenamine;
M6=3,6-dibromo-9-phenyl-9H-carbazole;
M7=2,7-dibromo-9,9-dioctyl-9H-fluorene;
M8=2-(4,7-bis(5-bromothiophen-2-yl)-2H-benzo[d][1,2,3]triazol-2-yl)-4,6-di-tert-butylphenol;
T1=2,4-di-tert-butyl-6-(4,7-dibromo-2H-benzo[d][1,2,3]triazol-2-yl)phenol;
T2=2-(3 ,5-di-tert-butyl-2-methoxyphenyl)-4,7-dibromo-2H-benzo[d][1,2,3]triazole;
T3=4,7-dibromo-2-hexyl-2H-benzo[d][1,2,3]triazole.

TABLE 2

| | | LEDs | | |
| | | 1000 cd/m² | | |
| Copolymer | Von | V | lm/W | Color |
|---|---|---|---|---|
| 1 | 3.5 | 7 | 2.7 | Green |
| 28 | 3 | 4 | 4.4 | Green |
| 24 | 3 | 10* | 0.2* | Orange |

*value measured @ 100 cd/m²

Example 22

Substituted Benzotriazoles as Chemical Sensor Materials

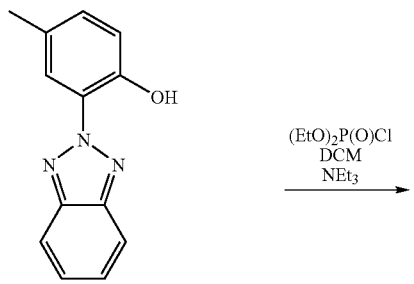

Non-emissive when excited at 365 nm (EtO)₂P(O)Cl
DCM
NEt₃
→

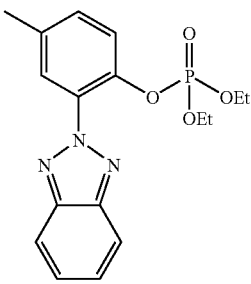

Strong blue emission when excited at 365 nm 2-benzotriazol-2-yl-4-methyl-phenol (Tinuvin-P, Ciba) (2 mmol), dichloromethane (10 mL), diethyl phosphochloridate (4 mmol), and triethylamine (4.4 mmol) were added, in that order, to a single-neck 100-mL round bottomed flask. The solution was stirred under nitrogen at room temperature for 16 h. The solvent was reduced under vacuum and the concentrated solution was chilled in a freezer at −19° C. for 2 h. White solid (Et₃NHCl) was filtered off. Exposing the filtrate to UV irradiation (365 nm) resulted in a faint blue luminescence. The filtrate was chromatographed with silica gel column (3×20 cm², D×L) using dichloromethane and then dichloromethane/methanol (95/5, v/v) as eluent. The luminescent fractions were collected and combined. The solvent was removed with a rotary evaporator. GC/MS showed molecular ion peaks associated with the product.

Example 22

4,7-dibromo-2-phenyl-2H-benzotriazole

Method 1

Synthesis of 2-phenylazoaniline

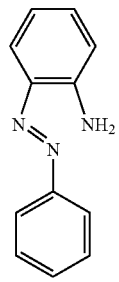

1,2-phenylenediamine (5.0 g, 46 mmol), nitrobenzene (4.73 mL, 46 mmol), and sodium hydroxide (1.84 g, 46 mmol) were mixed in an 100-mL 1-neck round bottomed flask. The mixture was heated in an oil bath at 120° C. for 1.5 h while being constantly triturated with a glass rod. The flask was cooled to room temperature and the product was extracted with dichloromethane. The extracted solution was concentrated under reduced pressure and purified with silica gel column using dichloromethane as eluent. The fractions containing the desired product were combined and the solvent was removed using a rotary evaporator. The product was dried under high vacuum for 16 h. Yield: 34%.

Synthesis of 2-phenyl-2H-benzotriazole

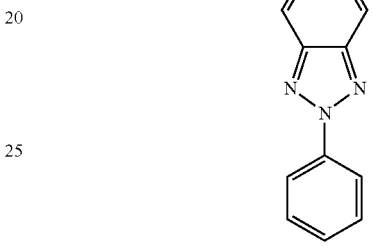

2-phenylazoaniline (3.47 g, 17.6 mmol) prepared above was placed in a 100-mL 1-neck round bottomed flask. Acetic acid (20 mL) and iodobenzene diacetate (6.23 g, 19.4 mmol) were added, in that order, resulting in an exotherm. The reaction was allowed to proceed for 1 hour during which time the mixture cooled to room temperature. Dichloromethane and water were added to the reaction mixture. The organic layer was separated and dried over MgSO4. The solution was filtered and concentrated using a rotary evaporator. The residue was purified on a silica gel column using dichloromethane as eluent. The fractions containing the desired product were combined and solvent removed. The solid was dried in a vacuum oven for 2 h. Yield: 34%.

Synthesis of 4,7-Dibromo-2-phenyl-2H-benzotriazole

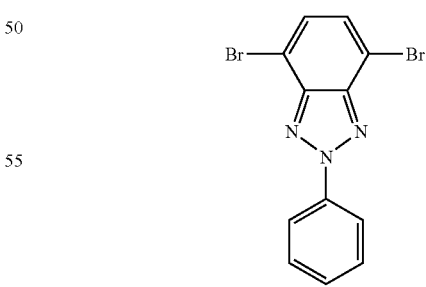

2-phenyl-2H-benzotriazole (1.10 g, 5.1 mmol) was placed in a 1-neck 250-mL round bottomed flask. HBr/acetic acid (45% w/v, 20 mL) and bromine (0.79 mL, 15.3 mmol) were added. The flask was connected to a condenser and a scrubber. The mixture was heated in an oil bath at 150° C. for 0.5 hr. The solution was cooled to room temperature. Bromine (0.79 mL, 15.3 mmol) was again added to the reaction mixture and it was again heated to 150° C. for 1 hr. This step was repeated three more times. Water (200 mL) and dichloromethane (200 mL) were added to the reaction mixture followed by aqueous sodium hydroxide (1.5 M) solution to neutralize the acid. The organic layer was separated and dried with MgSO4. The solution was filtered and the solvent concentrated using a rotary evaporator. The solid was further dried under high vacuum at 60° C. for 2 hr. Yield: 78%.

Method 2

Synthesis of 3,6-dibromo-1,2-phenylenediamine

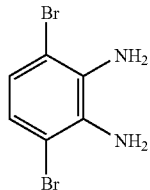

4,7-dibromobenzo[1,2,5]thiadiazole (6.0 g, 20.3 mmol), prepared according to WO 00/55927 PCT/GB00/00911 by bromination of benzo[1,2,5]thiadiazole, was placed in a 200-mL flask under a nitrogen atmosphere. Zinc dust (13.2 g, 203 mmol) and a mixture of acetic acid/water (35 mL/35 mL) were added. The flask was loosely capped with an inverted 1-neck flask. The reaction mixture was heated to 70° C. for 1 hr at which time reaction was complete as determined by TLC. The mixture was then cooled to room temperature and filtered. The solid was extracted with diethylether (3×100 mL). The extract was washed with saturated aqueous sodium bicarbonate and dried over MgSO4. The solution was filtered and evaporated to dryness using a rotary evaporator. The solid was purified by chromatography on a silica gel column, using dichloromethane as eluent. The appropriate fractions were combined and the solvent was removed under reducing pressure. A light yellow product was obtained. Yield: 70%.

Synthesis of 3,6-dibromo-2-phenylazo-phenylamine

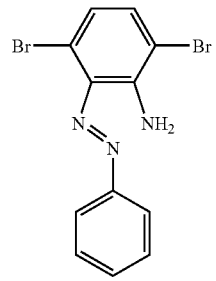

3,6-dibromo-1,2-phenylenediamine (1.33 g, 5.0 mmol), nitrobenzene (2.06 mL, 20 mmol), and sodium hydroxide (0.20 g, 5 mmol) were mixed in an 1-neck 100-mL round bottomed flask. The flask was heated in an oil bath at 160° C. for 3 h. The mixture was cooled to room temperature and dichloromethane was added to extract the product. The extract was filtered and the solution concentrated using a rotary evaporator. The solution was chromatographed on a silica gel column using dichloromethane as eluent. The fractions were combined and solvent removed under reduced pressure. The solid was further dried under high vacuum for 1 h. Yield: 3.5%.

Synthesis of 4,7-Dibromo-2-phenyl-2H-benzotriazole

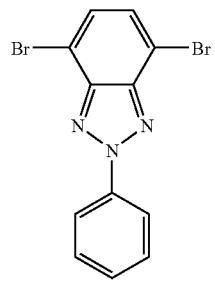

The 3,6-dibromo-2-phenylazo-phenylamine (120 mg, 0.34 mmol), iodobenzene diacetate (109 mg, 0.34 mmol), and acetic acid (5 mL) were added to a 1-neck 100-mL round bottom flask. The solution was stirred for 1 h at room temperature. The solvent was reduced with a rotary evaporator and the flask was stored at −19° C. for 16 h resulting in the formation of a solid cake. Water was added to the solid cake to dissolve the acid. A crystalline solid was collected by filtration and washed with water. GC/MS confirmed the solid as the desired product. Yield: 50%.

We claim:

1. A polymer or oligomer comprising:
    (a) at least one type of a constitutional repeating unit of the general formula selected from the group consisting of Formula I and Formula II, represented below, said constitutional repeating unit having a benzotriazole type group, either as part of the main chain or as a side chain

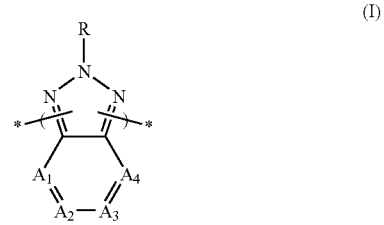

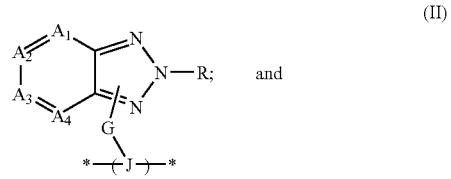

b) at least one type of a constitutional repeating unit of the general formula represented below by Formula III in the amount of 75 mol % or less:

wherein
R is H, D, alkyl, alkaryl, heteroalkyl, aryl, aralkyl, heteroaryl, alkyl ketone, aryl ketone, alkylester, arylester, amide, carboxylic acid, phenol, 2-hydroxyphenyl, 2-alkoxyphenyl, 2-aryloxyphenyl, substituted 2-hydroxyphenyl, substituted 2-alkoxyphenyl, substituted 2-aryloxyphenyl, fluoroalkyl, or fluoroaryl;

$A_1$ is C, when said benzotriazole type group is linked at $A_1$, or $A_1$ is CH, $CR_1$, or N, when said benzotriazole type group is not linked at $A_1$;

$A_2$ is C, when said benzotriazole type group is linked at $A_2$, or $A_2$ is CH, $CR_2$, or N, when said benzotriazole type group is not linked at $A_2$;

$A_3$ is C, when said benzotriazole type group is linked at $A_3$, or $A_3$ is CH, $CR_3$, or N, when said benzotriazole type group is not linked at $A_3$;

$A_4$ is CH, $CR_4$, or N, when said benzotriazole type group is not linked at $A_4$, or $A_4$ is C, when said benzotriazole type group is linked at $A_4$;

J is a trivalent moiety selected from the group consisting of 1,2,4-phenylenetriyl and $>CR_6CR_7R_8$—;

G is nil or is selected from the group consisting of —Ar—, —O—, —S—, —$NR_1$—, $CR_2R_3$—, —$CR_1R_2CR_3R_4$—, N=$CR_1$—, $CR_1$=$CR_2$—, —N=N—, —(CO)—, $C_3$ to $C_{30}$ alkyldiyl, and $C_3$ to $C_{30}$ heteroalkyldiyl;

Q is selected from the group consisting of —Ar—, —O—, —S—, —$NR_1$—, —$OCR_1R_2$—, —$CR_1R_2$—, —$OCR_1R_2CR_3R_4$—, —$CR_1R_2CR_3R_4$—, —N=$CR_1$—, —$CR_1$=N—, —$CR_1$=$CR_2$—, —N=N—, and —(CO)—, —$BR_1$—, $SiR_1R_2$—, —(CO)—O—, —O—(CO)—, —$NR_1$—(CO)—, and —(CO)—$NR_1$—, $C_3$ to $C_{30}$ alkyldiyl, and $C_3$ to $C_{30}$ heteroalkyldiyl;

$R_1$, $R_2$, $R_3$, $R_4$ are each independently selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and any two of adjacent $R_1$, $R_2$, $R_3$ or $R_4$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran;

$R_6$, $R_7$, and $R_8$ are each independently substituted or unsubstituted alkyl or aryl; and any two of adjacent $R_6$, $R_7$, $R_8$, are optionally bridging; and Ar is unsubstituted or substituted, single or multiple ring, fused or non-fused aromatic or heteroaromatic.

2. The polymer or oligomer of claim 1 comprising at least one type of a constitutional repeating unit of Formula IV, Formula V or Formula VI represented below:

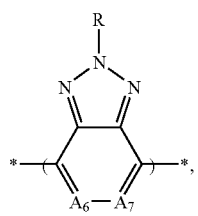

(IV)

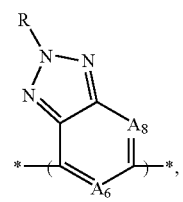

(V)

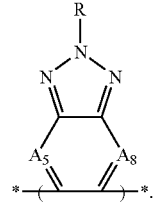

(VI)

wherein
R is H, D, alkyl, alkaryl, heteroalkyl, aryl, aralkyl, heteroaryl, alkyl ketone, aryl ketone, alkylester, arylester, amide, carboxylic acid, phenol, 2-hydroxyphenyl, 2-alkoxyphenyl, 2-aryloxyphenyl, substituted 2-hydroxyphenyl, substituted 2-alkoxyphenyl, substituted 2-aryloxyphenyl, fluoroalkyl, or fluoroaryl;

$A_5$ is CH, $CR_1$, or N;
$A_6$ is CH, $CR_2$, or N;
$A_7$ is CH, $CR_3$, or N;
$A_8$ is CH, $CR_4$, or N;

$R_1$, $R_2$, $R_3$, $R_4$ are each independently selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and any two of adjacent $R_1$, $R_2$, $R_3$ or $R_4$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; and $R_6$ and $R_7$ are each independently substituted or unsubstituted alkyl or aryl and are optionally bridging.

3. The polymer or oligomer of claim 2 comprising at least one type of a constitutional repeating unit of Formula VII represented below:

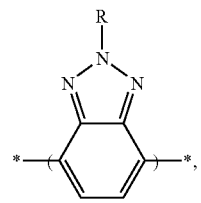

(VII)

wherein
R is H, D, alkyl, aryl, alkaryl, heteroalkyl, aryl, aralkyl, heteroaryl, alkyl ketone, aryl ketone, alkylester, arylester, amide, carboxylic acid, phenol, 2-hydroxyphenyl, 2-alkoxyphenyl, 2-aryloxyphenyl, substituted 2-hydroxyphenyl, substituted 2-alkoxyphenyl, substituted 2-aryloxyphenyl, fluoroalkyl, or fluoroaryl.

4. The polymer or oligomer of claim 3, wherein R is

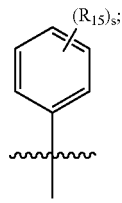

s is 0-5;

$R_{15}$ is selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and when s is 2-5, any two of adjacent $R_{15}$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; and $R_6$ and $R_7$ are each independently substituted or unsubstituted alkyl or aryl and are optionally bridging.

5. The polymer or oligomer of claim 4, wherein R is selected from the group consisting of:

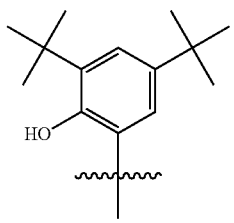 and 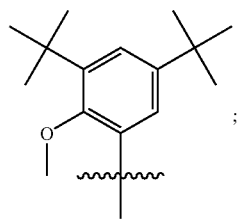

$R_{50}$ and $R_{51}$ are each independently selected from the group consisting of H, D, F, alkyl, alkaryl, heteroalkyl, aryl, aralkyl, heteroaryl, fluoroalkyl, fluoroaryl, amide, and ester; and $R_{52}$ is selected from the group consisting of alkyl, aryl, heteroaryl, fluoroalkyl, and fluoroaryl.

6. The polymer or oligomer of claim 5, wherein R is selected from the group consisting of:

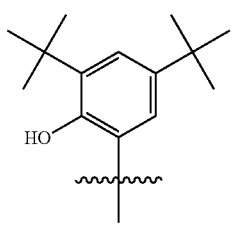 and 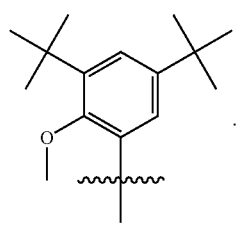

7. The polymer or oligomer of claim 3, wherein R is alkyl.

8. The polymer or oligomer of claim 7, wherein R is n-hexyl.

9. The polymer or oligomer of claim 1, containing at least one type of a constitutional repeating unit of the general formula represented below by Formula III:

wherein

Q is selected from the group consisting of:

(a)
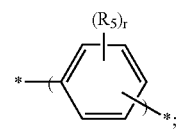

(b)
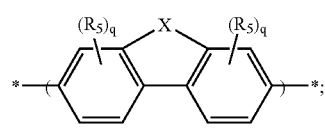

(c)
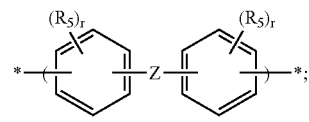

(d)
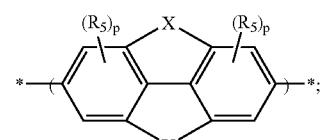

(e)
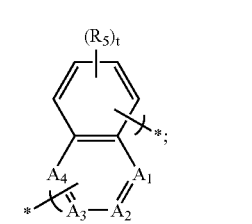

(f)
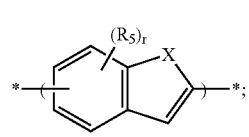

(g)
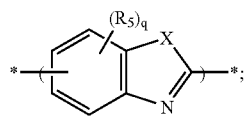

(h)
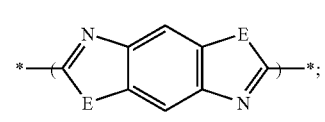

(i)
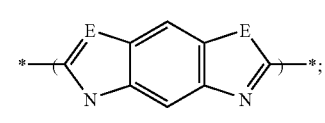

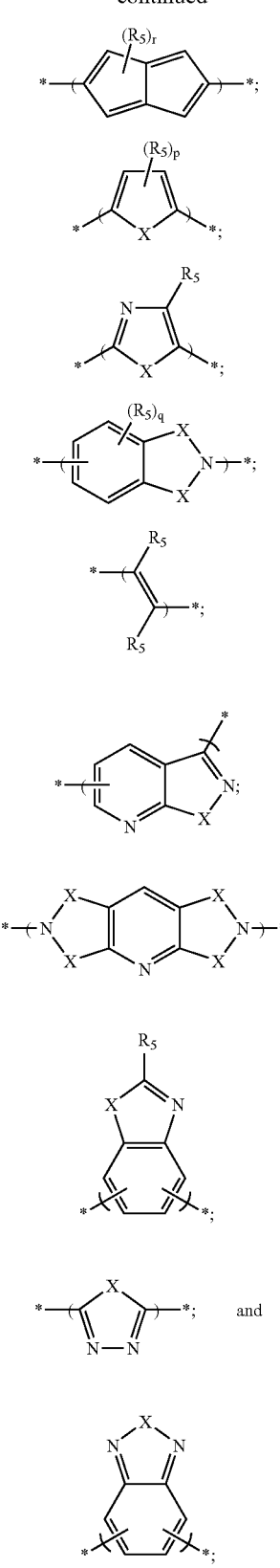

aralkyl, heteroaryl, aryl, alkyl ketone, aryl ketone, alkylester, arylester, amide, carboxylic acid, fluoroalkyl, fluoroaryl, polyalkalene oxy, linear, dendrimeric or hyperbranched polymeric, and any two of adjacent $R_5$ groups are optionally bridging;

p is 0-2;
q is 0-3;
r is 0-4;
s is 0-5;
t is 0-6;

X and Y are each independently selected from the group consisting of —O—, —S—, —$NR_6$—, and —$CR_6R_7$—, —$CR_6R_7CR_8R_9$—, —N=$CR_6$—, —$CR_6$=$CR_7$—, —N=N—, and —(CO)—;

Z is selected from the group consisting of —O—, —S—, —$NR_6$—, aryl, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, oxazole, oxadiazole, thiazole, thiadiazole, substituted triazole, tetrazole, tetrazine, triazine, substituted triazine, linear, dendrimeric or hyperbranched polymeric, and —$CR_6R_7$—, —$CR_6R_7CR_8R_9$—, N=$CR_6$—, $CR_6$=$CR_7$—, —N=N—, and —(CO)—;

$R_6$, $R_7$, $R_8$, and $R_9$ are independently selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic, and any two of adjacent $R_6$, $R_7$, $R_8$, and $R_9$ are optionally bridging;

E is selected from the group consisting of O, NH, and S;
$A_1$ is C, when group is linked at $A_1$, or $A_1$ is CH, $CR_1$, or N, when group is not linked at $A_1$;
$A_2$ is C, when group is linked at $A_2$, or $A_2$ is CH, $CR_2$, or N, when group is not linked at $A_2$;
$A_3$ is C, when group is linked at $A_3$, or $A_3$ is CH, $CR_3$, or N, when group is not linked at $A_3$; and
$A_4$ is C, when group is linked at $A_4$, or $A_4$ is CH, $CR_4$, or N, when group is not linked at $A_4$.

10. The polymer or oligomer of claim 1, wherein Q is selected from the group consisting of —O—, —S—, —C(O)—, —OC(O)—, —C(O)O—, —C(O)NH—, —$CH_2$—$CH_2$—, —$CH_2CH_2O$—, $CH2CH_2CH_2CH_2O$—, $CH_2CHCONH_2$—, —$CH_2CH(CN)$—, —$CH_2CH$=$CHCH_2$—, —CONHCO—, —$CH_2CH(OOCCH_3)$—, —$CH_2CHCl$—, —$CH_2CHOH$—, —CH($OCH_2CH_3$)$CH_2$—, —CH($OCH_2CH(CH_3)_2$)$CH_2$—, —$CH_2C(CH_3)(C(O)OCH_3)$—, —CH2C(CH3)(C(O)OH—, —NHC(O)NH—, —OC(O)NH—, —C(S)—, —$CH_2$—, —$CH_2CH_2$—, —$CH_2CH_2CH_2$—, —$CH_2CH_2CH_2CH_2$—, —$OCH_2$—, —$CH_2O$—, —$OCH_2CH_2$—, —$CH_2OCH_2$—, —$CH_2CH_2O$—, —$OCH_2CH_2CH_2$—, —$CH_2OCH_2CH_2$—, —$CH_2CH_2OCH_2$—, —$CH_2CH_2CH_2O$—, —$OCH_2CH_2CH_2CH_2$—, —$CH_2OCH_2CH_2CH_2$—, —$CH_2CH_2OCH_2CH_2$—, —$CH_2CH_2CH_2OCH_2$—, —$CH_2CH_2CH_2CH_2O$—, —C(O)NHCH_2—, —C(O)NHCH_2CH_2—, —$CH_2C(O)NHCH_2$—, —$CH_2CH_2C(O)NH$—, —C(O)NHCH_2CH_2CH_2—, —$CH_2C(O)NHCH_2CH_2$—, —$CH_2CH_2C(O)NHCH_2$—, —$CH_2CH_2CH_2C(O)NH$—, —C(O)NHCH_2CH_2CH_2CH_2—, —$CH_2C(O)NHCH_2CH_2CH_2$—, —$CH_2CH_2C(O)NHCH_2CH_2$—, —$CH_2CH_2CH_2C(O)NHCH_2$—, —$CH_2CH_2CH_2CH_2C(O)NH$—, —C(O)OCH_2—, —$CH_2C(O)OCH_2$—, —$CH_2CH_2C(O)OCH_2$—, —C(O)OCH_2CH_2—, —NHC(O)CH_2—, —$CH_2NHC(O)CH_2$—, —$CH_2CH_2NHC(O)CH_2$—, —NHC(O)CH_2CH_2—, $R_5$ is independently selected from the group consisting of H, D, F, alkoxy, aryloxy, alkyl, alkaryl, heteroalkyl, aryl, —CH₂NHC(O)CH₂CH₂—, —CH₂CH₂NHC(O)CH₂CH₂—, —C(O)NHCH₂—, —C(O)NHCH₂CH₂—, —OC(O)NHCH₂—, —OC(O)NHCH₂CH₂—, —OC(O)NHCH₂CH₂CH₂—, —NHCH₂—, —NHCH₂CH₂—, —CH₂NHCH₂—, —CH₂CH₂NHCH₂—, —C(O)CH₂—, —C(O)CH₂—CH₂—, —CH₂C(O)CH₂—, —CH₂CH₂C(O)CH₂—, —CH₂CH₂C(O)CH₂CH₂—, —CH₂CH₂C(O)—, —CH₂CH₂CH₂C(O)NHCH₂CH₂NH—, —CH₂CH₂CH₂C(O)NHCH₂CH₂NHC(O)—, —CH₂CH₂CH₂C(O)NHCH₂CH₂NHC(O)CH₂—, —CH₂CH₂CH₂C(O)NHCH₂CH₂NHC(O)CH₂CH₂—, —OC(O)NH(CH₂)₀₋₆(OCH2CH2)₀₋₂-, —C(O)NH(CH₂)₁₋₆NHC(O)—, —NHC(O)NH(CH₂)₁₋₆—NH—C(O)—, —OC(O)CH₂—, —O—C(O)CH₂CH₂—, and —OC(O)CH₂CH₂CH₂—.

11. The polymer or oligomer of claim 9, wherein Q is

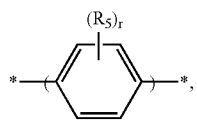

wherein
R₅ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent R₅ groups are optionally bridging; and
r is 0-4.

12. The polymer or oligomer of claim 11, wherein Q is

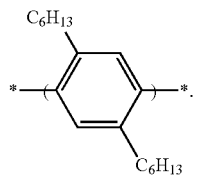

13. The polymer or oligomer of claim 6 or 8, comprising at least one type of a constitutional repeating unit of the general formula represented below by Formula III:

 (III)

wherein Q is

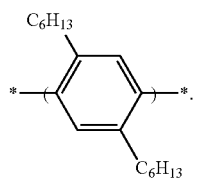

14. The polymer or oligomer of claim 11, wherein Q is

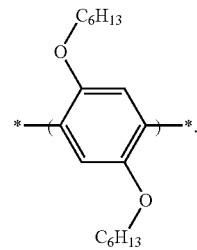

15. The polymer or oligomer of claim 6 or 8 comprising at least one constitutional repeating unit of the general formula represented below Formula III:

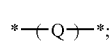 (III)

wherein Q is

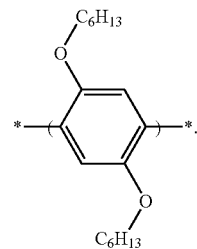

16. The polymer or oligomer of claim 6 or 8, comprising at least two different types of constitutional repeating units of the general formula represented below by Formula III:

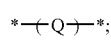 (III)

wherein at least one of the two different types of constitutional repeating units is selected from the group consisting of

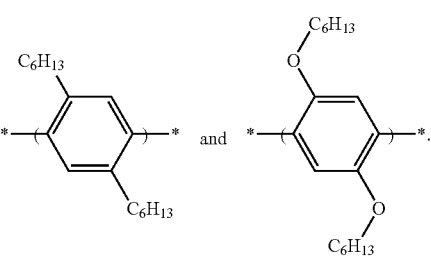

17. The polymer or oligomer of claim 9, wherein Q is

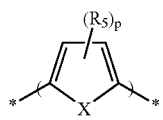

wherein $R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent $R_5$ groups are optionally bridging;

p is 0-2;

X is selected from the group consisting of —O—, —S—, —NR$_6$—, and CR$_6$R$_7$—, —CR$_6$R$_7$CR$_8$R$_9$—, —N═CR$_6$—, —CR$_6$═CR$_7$—, —N═N—, and —(CO)—; and $R_6$, $R_7$, $R_8$, and $R_9$ are independently selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic, and any two of adjacent $R_6$, $R_7$, $R_8$, and $R_9$ are optionally bridging.

18. The polymer or oligomer of claim 17, wherein Q is

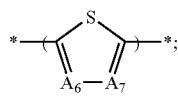

$A_6$ is CH, $CR_2$, or N;

$A_7$ is CU, $CR_3$, or N;

$R_2$ and $R_3$ are each independently selected from the group consisting of H, D, —NR$_6$R$_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and $R_2$ and $R_3$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; and $R_6$ and $R_7$ are each independently substituted or unsubstituted alkyl or aryl and are optionally bridging.

19. The polymer or oligomer of claim 18, wherein Q is

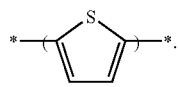

20. The polymer or oligomer of claim 6 or 8, comprising at least one type of a constitutional repeating unit of the general formula represented below by Formula III:

 (III)

wherein

Q is

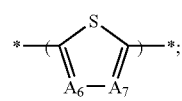

$A_6$ is CH, $CR_2$, or N;

$A_7$ is CH, $CR_3$, or N;

$R_2$ and $R_3$ are each independently selected from the group consisting of H, D, —NR$_6$R$_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and $R_2$ and $R_3$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; and $R_6$ and $R_7$ are each independently substituted or unsubstituted alkyl or aryl and are optionally bridging.

21. The polymer or oligomer of claim 6 or 8, comprising at least one type of a constitutional repeating unit of the general formula represented below by Formula III:

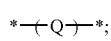 (III)

wherein Q is

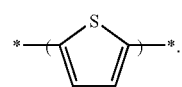

22. The polymer or oligomer of claim 21, comprising further at least three different types of constitutional repeating units of the general formula represented below Formula III:

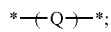 (III)

wherein at least one of the three different types of constitutional repeating units is selected from the group consisting of

23. The polymer or oligomer of claim 9, wherein Q is

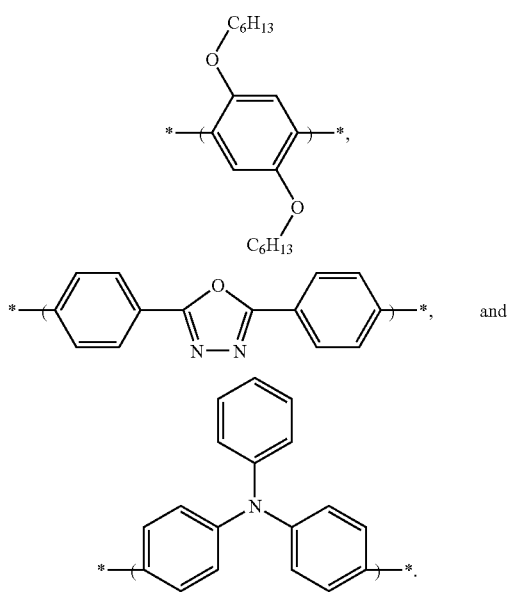

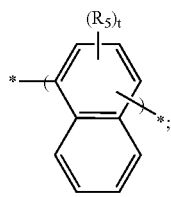

R$_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, and any two of adjacent R$_5$ groups are optionally bridging; and t is 0-6.

24. The polymer or oligomer of claim 23, wherein Q is

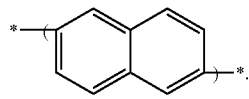

25. The polymer or oligomer of claim 6 or 8, comprising at least one constitutional repeating unit of the general formula represented below by Formula III:

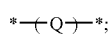  (III)

wherein Q is

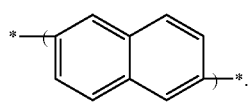

26. The polymer or oligomer of claim 9, wherein Q is

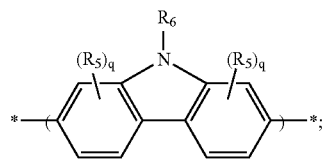

R$_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, and any two of adjacent R$_5$ groups are optionally bridging;

R$_6$ is selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic; and q is 0-3.

27. The polymer or oligomer of claim 26, wherein Q is

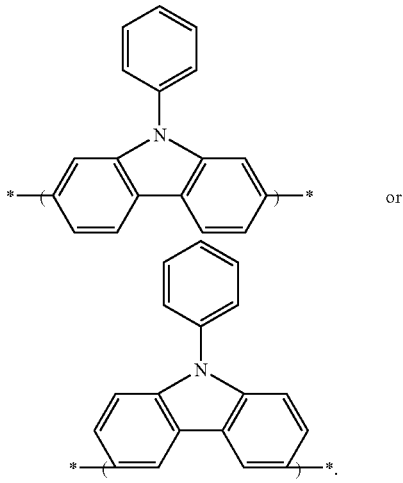

or

28. The polymer or oligomer of claim 6 or 8, wherein Q is or

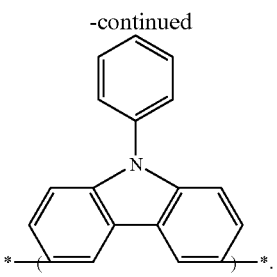

29. The polymer or oligomer of claim 6 or 8, comprising at least two different types of constitutional repeating units of the general formula represented below by Formula III:

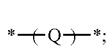 (III)

wherein at least one Q is selected from the group consisting of

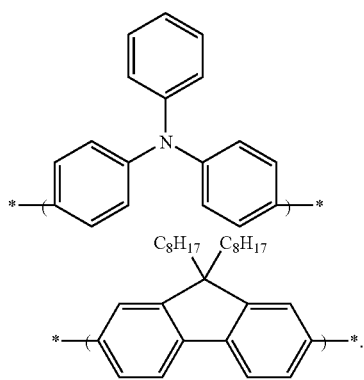 and

30. The polymer or oligomer of claim 9, wherein Q is

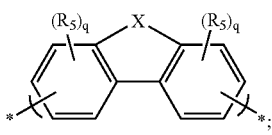

$R_5$ is each independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, and any two of adjacent $R_5$ groups are optionally bridging;

q is 0-3;

X is selected from the group consisting of —O—, —S—, —$NR_6$—, and —$CR_6R_7$—, —$CR_6R_7CR_8R_9$—, —N=$CR_6$—, $CR_6$=$CR_7$—, —N=N—, and —(CO)—; and $R_6$, $R_7$, $R_8$, and $R_9$ are each independently selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic, and any two of adjacent $R_6$, $R_7$, $R_8$, and $R_9$ are optionally bridging.

31. The polymer or oligomer of claim 30, wherein Q is

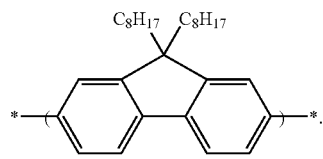

32. The polymer or oligomer of claim 6 or 8, wherein Q is

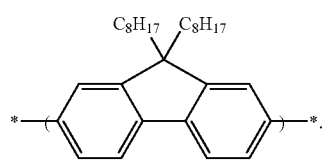

33. The polymer or oligomer of claim 9, wherein Q is

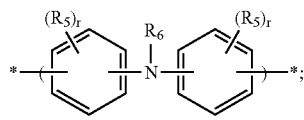

$R_5$ is each independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent $R_5$ groups are optionally bridging, $R_6$ is selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic; and r is 0-4.

34. The polymer or oligomer of claim 33, wherein Q is

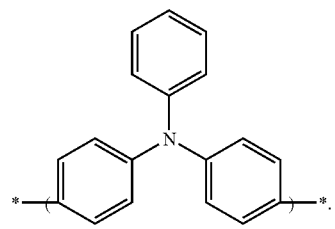

35. The polymer or oligomer of claim 6 or 8, comprising at least two constitutional repeating units of the general formula represented below by Formula III:

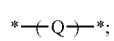 (III)

wherein at least one Q is selected from the group consisting of

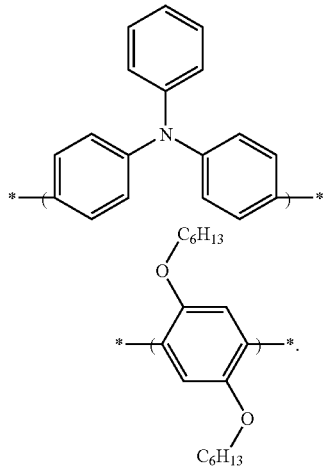

and

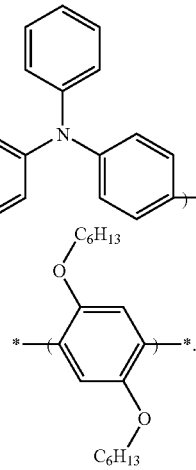

36. The polymer or oligomer of claim 6 or 8, comprising at least two types of constitutional repeating units of the general formula represented below by Formula III:

$$*\!-\!(\!Q\!)\!-\!*;\qquad\text{(III)}$$

wherein at least one Q is selected from the group consisting of

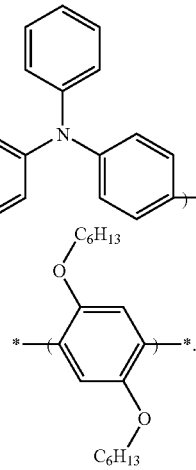

and

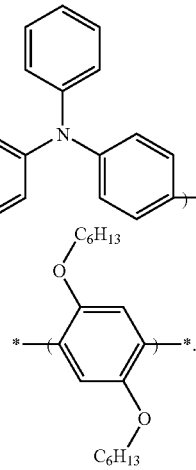

37. The polymer or oligomer of claim 6 or 8, comprising at least one type of a constitutional repeating unit of the general formula represented below by Formula III:

$$*\!-\!(\!Q\!)\!-\!*;\qquad\text{(III)}$$

wherein Q is

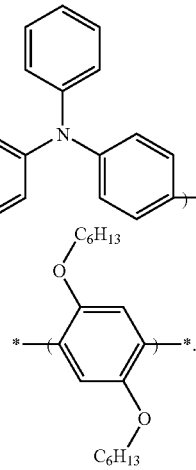

38. The polymer or oligomer of claim 6 or 8, comprising at least two constitutional repeating units of the general formula represented below by Formula III:

$$*\!-\!(\!Q\!)\!-\!*;\qquad\text{(III)}$$

wherein at least one Q is selected from the group consisting of

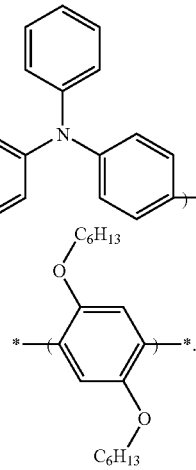

and

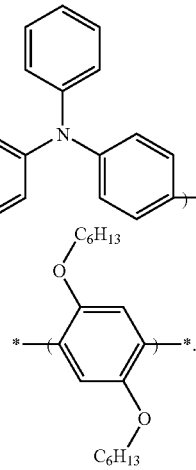

39. The polymer or oligomer of claim 9, wherein Q is

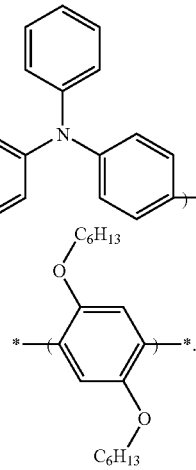

$R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent $R_5$ groups are optionally bridging; and r is 0-4;

X is selected from the group consisting of —O—, —S—, —NR_6—, and —CR_6R_7—, —CR_6R_7CR_8R_9—, —N=CR_6—, CR_6=CR_7—, —N=N—, and —(CO)—;

$R_6, R_7, R_8,$ and $R_9$ are each independently selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic, and any two adjacent $R_6, R_7, R_8,$ and $R_9$ are optionally bridging.

40. The polymer or oligomer of claim 6 or 8, wherein Q is

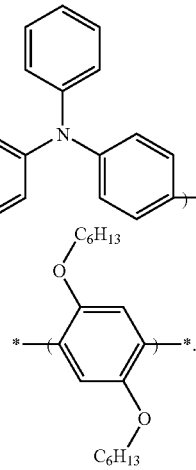

$R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent $R_5$ groups are optionally bridging; and r is 0-4;

X is selected from the group consisting of —O—, —S—, —NR$_6$—, and —CR$_6$R$_7$—, —CR$_6$R$_7$CR$_8$R$_9$—, —N=CR$_6$—, CR$_6$=CR$_7$—, —N=N—, and —(CO)—;

$R_6$, $R_7$, $R_8$, and $R_9$ are each independently selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic, and any two adjacent $R_6$, $R_7$, $R_8$, and $R_9$ are optionally bridging.

41. The polymer or oligomer of claim 1 wherein said polymer or oligomer comprises a constitutional repeating unit selected from the group consisting of

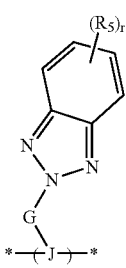 and 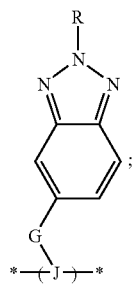;

wherein $R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent (geminal, vicinal, or ortho) $R_5$ groups are optionally bridging;

J is a trivalent moiety selected from the group consisting of 1,2,4-phenylenetriyl and >CR$_6$CR$_7$R$_8$—;

G is nil or is selected from the group consisting of —Ar—, —O—, —S—, —NR$_1$—, CR$_2$R$_3$—, —CR$_1$R$_2$CR$_3$R$_4$—, N=CR$_1$, CR$_1$=CR$_2$—, —N=N—, —(CO)—, $C_3$ to $C_{30}$ alkyldiyl, and $C_3$ to $C_{30}$ heteroalkyldiyl;

$R_1$, $R_2$, $R_3$, $R_4$ are each independently selected from the group consisting of H, D, —NR$_6$R$_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and any two of adjacent (geminal, vicinal, or ortho) $R_1$, $R_2$, $R_3$ or $R_4$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran;

$R_6$, $R_7$, and $R_8$ are each independently substituted or unsubstituted alkyl or aryl; and any two of adjacent $R_6$, $R_7$, $R_8$, are optionally bridging;

Ar is unsubstituted or substituted, single or multiple ring, fused or non-fused aromatic or heteroaromatic; and r is 0-4.

42. The polymer or oligomer of claim 41, wherein J is >CHCH$_2$—.

43. The polymer or oligomer of claim 1 wherein said polymer is comprised of a constitutional repeating unit selected from the group consisting of

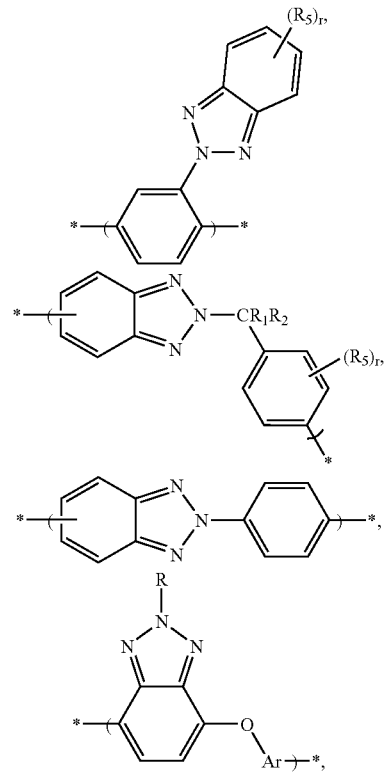

wherein

R is H, D, alkyl, alkaryl, heteroalkyl, aryl, aralkyl, heteroaryl, alkyl ketone, aryl ketone, alkylester, arylester, amide, carboxylic acid, phenol, 2-hydroxyphenyl, 2-alkoxyphenyl, 2-aryloxyphenyl, substituted 2-hydroxyphenyl, substituted 2-alkoxyphenyl, substituted 2-aryloxyphenyl, fluoroalkyl, or fluoroaryl;

$R_1$ and $R_2$ are each independently selected from the group consisting of H, D, —NR$_6$R$_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic;

$R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent $R_5$ groups are optionally bridging;

$R_6$ and $R_7$ are each independently substituted or unsubstituted alkyl or aryl, and are optionally bridging;

Ar is unsubstituted or substituted, single or multiple ring, fused or non-fused aromatic or heteroaromatic; and r is 0-4.

44. The polymer or oligomer of claim 1 wherein said polymer is comprised of a constitutional repeating unit represented below

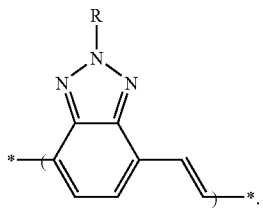

45. The polymer or oligomer of claim 1 comprising:
(a) about 25 mol % of at least one constitutional repeating unit of the general formula selected from the group consisting of Formula I and Formula II; and
(b) about 75 mol % of at least one constitutional repeating unit of the general formula represented by Formula III.

46. The polymer or oligomer of claim 1 comprising:
(a) about 40 mol % of at least one constitutional repeating unit of the general formula selected from the group consisting of Formula I and Formula II; and
(b) about 60 mol % of at least one constitutional repeating unit of the general formula represented by Formula III.

47. The polymer or oligomer of claim 1 comprising:
(a) about 50 mol % of at least one constitutional repeating unit of the general formula selected from the group consisting of Formula I and Formula II; and
(b) about 50 mol % of at least one constitutional repeating unit of the general formula represented by Formula III.

48. The polymer of claim 1 wherein the polymer has an average molecular weight $M_w$ of at least about 15,000 Daltons.

49. The polymer of claim 1 wherein the polymer has a weight average molecular weight of at least about 20,000 Daltons.

50. The polymer of claim 1 wherein the polymer has a weight average molecular weight $M_w$ of at least about 40,000 Daltons.

51. The polymer of claim 1 wherein the polymer has a weight average molecular weight $M_w$ of at least about 60,000 Daltons.

52. The polymer of claim 1 wherein the polymer has a weight average molecular weight $M_w$ of at least about 80,000 Daltons.

53. The polymer of claim 1 wherein the polymer has a weight average molecular weight $M_w$ of at least about 100,000 Daltons.

54. The oligomer of claim 1 having a weight average molecular weight $M_w$ of from about 200 to about 15000 Daltons.

55. The polymer of claim 1 wherein the polymer is a copolymer.

56. The polymer of claim 55 wherein the polymer is a block co-polymer.

57. The polymer of claim 55 wherein the polymer is a random co-polymer.

58. The polymer of claim 1 wherein the polymer is a crosslinked polymer.

59. The polymer of claim 1 wherein the polymer is a hyperbranched polymer.

60. The polymer of claim 1 wherein the polymer is a star polymer.

61. The polymer of claim 1 wherein the polymer is a photoluminescent polymer and/or an electroluminescent polymer.

62. The photoluminescent polymer of claim 61, wherein the photoluminescent polymer is suitable for excitation in the UV, visible, or infrared region.

63. The photoluminescent polymer of claim 61, wherein the photoluminescent polymer is capable of emitting light having a wavelength in the range 350-750 nanometers.

64. The photoluminescent polymer of claim 61, wherein the photoluminescent polymer is capable of emitting light having a wavelength in the range 450-700 nanometers.

65. The photoluminescent polymer of claim 61, wherein the photoluminescent polymer is capable of emitting light having a wavelength in the range 500-650 nanometers.

66. A process of preparing a polymer or oligomer comprising:
(a) admixing
(i) at least one compound selected from the group consisting of Formula VIII, Formula IX, and Formula X, represented below

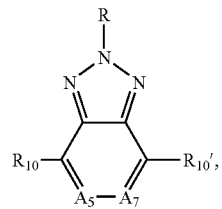
(VIII)

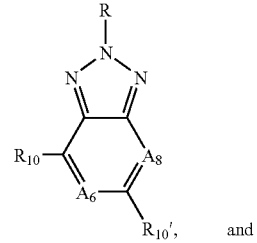
(IX)

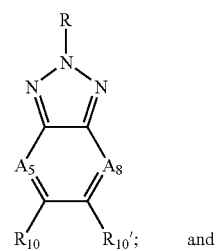
(X)

and (ii) optionally, at least one compound of the general formula represented below by Formula XI:

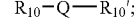
(XI)

wherein
R is H, D, alkyl, alkaryl, heteroalkyl, aryl, aralkyl, heteroaryl, alkyl ketone, aryl ketone, alkylester, arylester, amide, carboxylic acid, phenol, 2-hydroxyphenyl, 2-alkoxyphenyl, 2-aryloxyphenyl, substituted 2-hydroxyphenyl, substituted 2-alkoxyphenyl, substituted 2-aryloxyphenyl, fluoroalkyl, or fluoroaryl;
$A_5$ is CH, $CR_1$, or N;
$A_6$ is CH, $CR_2$, or N;
$A_7$ is CH, $CR_3$, or N;

$A_8$ is CH, $CR_4$, or N;

$R_1$, $R_2$, $R_3$, $R_4$ are each independently selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and any two of adjacent $R_1$, $R_2$, $R_3$ or $R_4$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran;

Q is selected from the group consisting of —Ar—, —O—, —S—, —$NR_1$—, —$OCR_1R_2$—, —$CR_1R_2$—, —$OCR_1R_2CR_3R_4$—, —$CR_1R_2CR_3R_4$—, —N=$CR_1$—, —$CR_1$=N—, —$CR_1$=$CR_2$—, —N=N—, and —(CO)—, —$BR_1$—, $SiR_1R_2$—, —(CO)—O—, —O—(CO)—, —$NR_1$—(CO)—, and —(CO)—$NR_1$—, $C_3$ to $C_{30}$ alkyldiyl, and $C_3$ to $C_{30}$ heteroalkyldiyl;

$R_6$ and $R_7$ are each independently substituted or unsubstituted alkyl or aryl; and $R_6$ and $R_7$ are optionally bridging;

Ar is unsubstituted or substituted, single or multiple ring, fused or non-fused aromatic or heteroaromatic; and $R_{10}$ and $R_{10}'$ are each independently a group or groups capable of participating in aryl to aryl and/or aryl to alkyl coupling reaction; and (b) adding a polymerization catalyst and optional co-reactants into the mixture to cause:

(i) polymerization to form a carbon to carbon bond linking at least one compound selected from the group consisting of Formula VIII, Formula IX, and Formula X with at least one other compound selected from the group consisting of Formula VIII, Formula IX, and Formula X; and/or (ii) polymerization to form a carbon to carbon bond linking at least one compound selected from the group consisting of Formula VIII, Formula IX, and Formula X with at least one compound of Formula XI.

67. The process of claim 66, wherein $R_{10}$ and $R_{10}'$ are each independently a group or groups selected from the group consisting of H, D, halide, —Si($R_{11}$), —Sn($R_{11}$)$_3$, —Cu, —Cu(CN)Li, —Li, —MgBr, —ZnCl, —ZnBr, —ZnI, —MnBr, —MnCl, —MnI, —HgCl, —OTf, —SH, —$SO_3CH_3$, —B(O$R_{12}$)$_2$;

$R_{11}$ is each independently selected from the group consisting of halide, hydroxyl, alkyl, and alkyloxy; and $R_{12}$ is each independently selected from the group consisting of H, D, alkyl, and aryl or the two $R_{12}$ taken together with the oxygen atoms to which they are connected form cyclic boronic acid esters.

68. The process of claim 66, wherein said aryl to aryl coupling reaction is selected from the group consisting of Suzuki, Colon, Stille, and Yamamoto.

69. The process of claim 66, comprising admixing (i) at least one compound of Formula XII represented below:

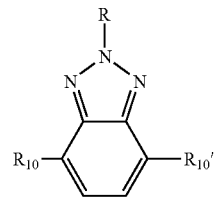

(XII)

wherein

R is H, D, alkyl, alkaryl, heteroalkyl, aryl, aralkyl, heteroaryl, alkyl ketone, aryl ketone, alkylester, arylester, amide, carboxylic acid, phenol, 2-hydroxyphenyl, 2-alkoxyphenyl, 2-aryloxyphenyl, substituted 2-hydroxyphenyl, substituted 2-alkoxyphenyl, substituted 2-aryloxyphenyl, fluoroalkyl, or fluoroaryl;

$R_{10}$ and $R_{10}'$ are each independently a group or groups capable of participating in aryl to aryl and/or aryl to alkyl coupling reaction; and (ii) at least one compound of the general formula represented below by Formula XI:

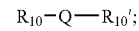

$R_{10}$—Q—$R_{10}'$;    (XI)

wherein

Q is selected from the group consisting of —Ar—, —O—, —S—, —$NR_1$—, —$OCR_1R_2$—, —$CR_1R_2$—, —$OCR_1R_2CR_3R_4$—, —$CR_1R_2CR_3R_4$—, —N=$CR_1$—, —$CR_1$=N—, —$CR_1$=$CR_2$—, —N=N—, and —(CO)—, —$BR_1$—, $SiR_1R_2$—, —(CO)—O—, —O—(CO)—, —$NR_1$—(CO)—, and —(CO)—$NR_1$—, $C_3$ to $C_{30}$ alkyldiyl, and $C_3$ to $C_{30}$ heteroalkyldiyl;

$R_1$, $R_2$, $R_3$, $R_4$ are each independently selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and any two of adjacent $R_1$, $R_2$, $R_3$ or $R_4$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; and Ar is unsubstituted or substituted, single or multiple ring, fused or non-fused aromatic or hetero aromatic.

70. The process of claim 69, wherein

R is

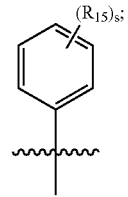

s is 0-5;

$R_{15}$ is selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and when s is 25, any two of adjacent $R_{15}$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; and $R_6$ and $R_7$ are each independently substituted or unsubstituted alkyl or aryl and are optionally bridging.

71. The process of claim 70, wherein R is selected from the group consisting of:

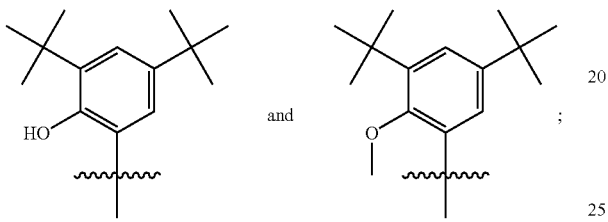

$R_{50}$ and $R_{51}$ are each independently selected from the group consisting of H, D, F, alkyl, alkaryl, heteroalkyl, aryl, aralkyl, heteroaryl, fluoroalkyl, fluoroaryl, amide, and ester; and $R_{52}$ is selected from the group consisting of alkyl, aryl, heteroaryl, fluoroalkyl, and fluoroaryl.

72. The process of claim 71, wherein R is selected from the group consisting of:

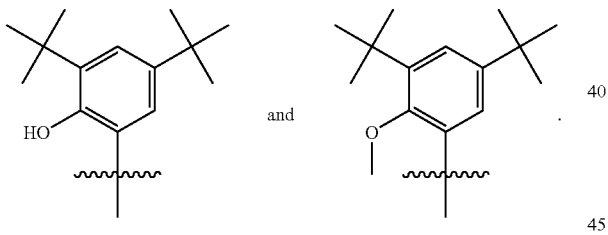

73. The process of claim 69, wherein R is alkyl.
74. The process of claim 73, wherein R is n-hexyl.
75. The process of any of claims 69-74, wherein $R_{10}$ and $R_{10}'$ in Formula X are each independently a halide.
76. The process of claim 75, wherein $R_{10}$ and $R_{10}'$ in Formula X are each a bromide.
77. The process of any of claims 69-74, wherein $R_{10}$ and $R_{10}'$ in formula X are each independently

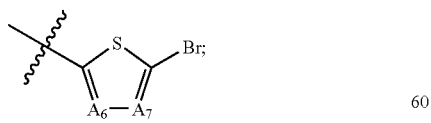

$A_6$ is CH, $CR_2$, or N;
$A_7$ is CH, $CR_3$, or N;
$R_2$ and $R_3$ are each independently selected from the group consisting of H, D, —$NR_6R_7$, halide, alkoxy, aryloxy, alkyl, alkaryl, heteroalkyl, aryl, aralkyl, heteroaryl, alkyl ketone, aryl ketone, alkylester, arylester, amide, carboxylic acid, phenol, alkylphenol, fluoroalkyl, fluoroaryl, alkyleneoxy, polyalkylene oxy, polyalkylene, linear or dendritic; and $R_2$ and $R_3$ are optionally bridging, or taken together with the two carbons to which each is respectively attached may form an aromatic ring selected from the group consisting of unsubstituted or substituted benzene, naphthalene, anthracene, thiophene, pyridine, bipyridine, pyrazine, pyrimidine, oxadiazole, thiadiazole, and benzofuran; and $R_6$ and $R_7$ are each independently substituted or unsubstituted alkyl or aryl and are optionally bridging.

78. The process of claim 77, wherein $R_{10}$ and $R_{10}'$ in formula X are each

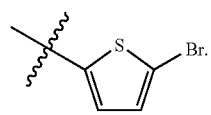

79. The process of claim 60 or 66, comprising admixing
(i) at least one compound of Formula XI wherein
Q in Formula XI is

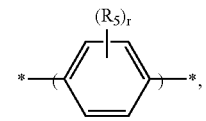

wherein $R_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent $R_5$ groups are optionally bridging;

r is 0-4;

$R_{10}$ and $R_{10}'$ in formula XI are each independently —$B(OR_{12})_2$;

$R_{12}$ is each independently selected from the group consisting of H, D, alkyl, and aryl, or the two $R_{12}$ taken together with the oxygen atoms to which they are connected form cyclic boronic acid esters; and/or (ii) at least one other compound of Formula XI wherein
Q in Formula XI is selected from the group consisting of (a)

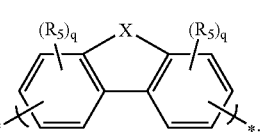

(b)

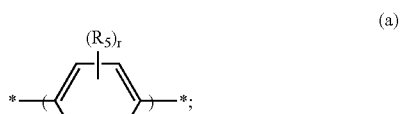

-continued (c)

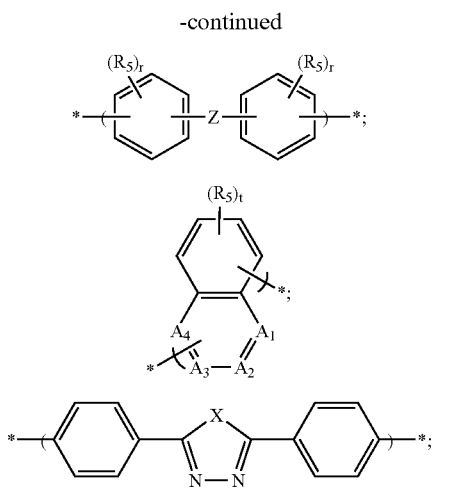

(d)

(e)

R$_5$ is independently selected from the group consisting of H, D, F, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, linear, dendrimeric or hyperbranched polymeric, any two of adjacent R$_5$ groups are optionally bridging;

q is 0-3;
r is 0-4;
t is 0-6;

X is selected from the group consisting of —O—, —S—, —NR$_6$—, and —CR$_6$R$_7$—, —CR$_6$R$_7$CR$_8$R$_9$—, —N═CR$_6$—, —CR$_6$═CR$_7$—, —N═N—, and —(CO)—;

Z is selected from the group consisting of —O—, —S—, —NR$_6$—, aryl, alkoxy, aryloxy, alkyl, alkaryl, heteroalkyl, aryl, aralkyl, heteroaryl, alkyl ketone, aryl ketone, alkylester, arylester, amide, carboxylic acid, fluoroalkyl, fluoroaryl, polyalkalene oxy, oxazole, oxadiazole, thiazole, thiadiazole, substituted triazole, tetrazole, tetrazine, triazine, substituted triazine, linear, dendrimeric or hyperbranched polymeric, and —CR$_6$R$_7$—, —CR$_6$R$_7$CR$_8$R$_9$—, N═CR$_6$—, CR$_6$═CR$_7$—, —N═N—, and —(CO)—;

R$_6$, R$_7$, R$_8$, and R$_9$ are independently selected from the group consisting of H, D, F, alkyl, alkaryl, heteroalkyl, aryl, aralkyl, heteroaryl, alkyleneoxy, polyalkylene oxy, alkoxy, aryloxy, fluoroalkyl, fluoroaryl, and linear or dendritic, and any two of adjacent R$_6$, R$_7$, R$_8$, and R$_9$ are optionally bridging; and R$_{10}$ and R$_{10}$' in Formula XI are each independently a halide.

80. The process of claim 79, wherein
in (i)
Q in Formula XI is selected from the group consisting of

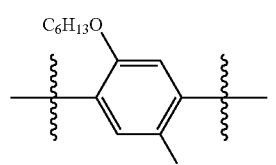 and

-continued

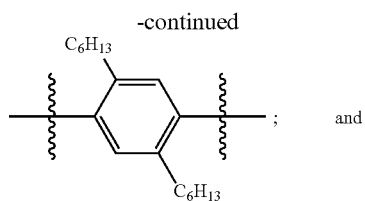 and

R$_{10}$ and R$_{10}$' in Formula XI are each independently —B(OR$_{12}$)$_2$;

R$_{12}$ is each independently selected from the group consisting of H, D, alkyl, and aryl, or the two R$_{12}$ taken together with the oxygen atoms to which they are connected form cyclic boronic acid esters; and in (ii)
Q in Formula IX is selected from the group consisting of (a)

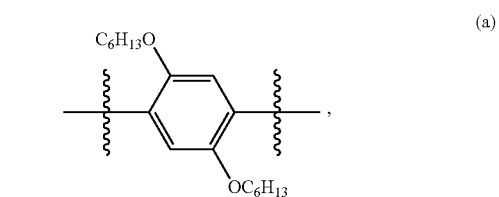

(b)

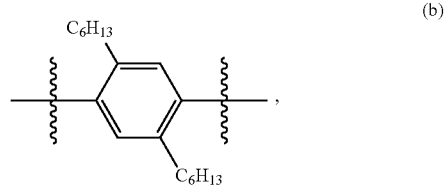

(c)

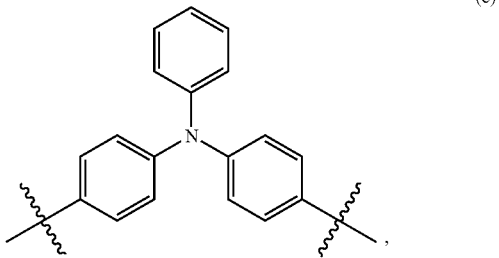

(d)

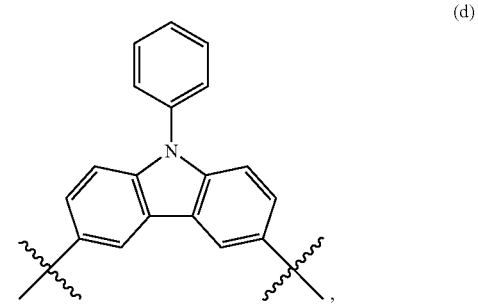

(e)

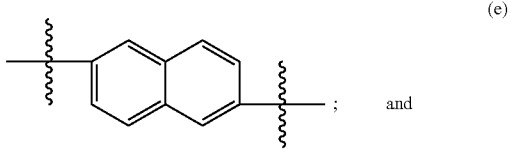 and

R$_{10}$ and R$_{10}$' in Formula XI are each independently a bromide.

81. The process of claim 79, comprising admixing
(i) at least one said compound of Formula XI wherein Q in Formula XI is

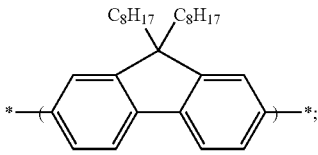

$R_{10}$ and $R_{10}'$ in Formula XI are each independently —$B(OR_{12})_2$; and $R_{12}$ is each independently selected from the group consisting of H, D, alkyl, and aryl, or the two $R_{12}$ taken together with the oxygen atoms to which they are connected form cyclic boronic acid esters.

82. The process of claim 81, comprising further admixing
(i) at least one said compound of Formula XI wherein Q in Formula XI is

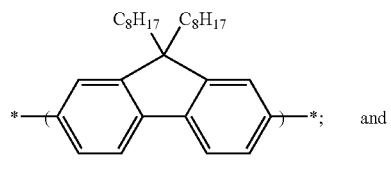

$R_{10}$ and $R_{10}'$ are each a bromide.

83. The process of claim 66, wherein said polymerization initiator is a palladium catalyst selected from the group consisting of $Pd(PPh_3)_4$, $Pd(OAc)_2$, $PdCl_2(dppb)$, and $Pd(dba)_2/PPh_3$, in combination with a base.

84. The process of claim 83, wherein said base is selected from the group consisting of $Na_2CO_3$, $K_2CO_3$, $NaHCO_3$, $KHCO_3$, $CsOH$, $CsHCO_3$, $Cs_2CO_3$, $Ba(OH)_2$, $KOH$, and $NaOH$.

* * * * *